US007595345B2

United States Patent
Bunel et al.

(10) Patent No.: US 7,595,345 B2
(45) Date of Patent: Sep. 29, 2009

(54) VITAMIN D RECEPTOR MODULATORS

(75) Inventors: Emilio Enrique Bunel, Thousand Oaks, CA (US); Robert Peter Gajewski, Indianapolis, IN (US); Charles David Jones, Indianapolis, IN (US); Jianliang Lu, Fishers, IN (US); Sunil Nagpal, Carmel, IN (US); Tianwei Ma, Carmel, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 409 days.

(21) Appl. No.: 10/579,562

(22) PCT Filed: Nov. 16, 2004

(86) PCT No.: PCT/US2004/037182

§ 371 (c)(1), (2), (4) Date: May 12, 2006

(87) PCT Pub. No.: WO2005/051893

PCT Pub. Date: Jun. 9, 2005

(65) Prior Publication Data

US 2008/0200552 A1    Aug. 21, 2008

Related U.S. Application Data

(60) Provisional application No. 60/523,301, filed on Nov. 20, 2003.

(51) Int. Cl.
A61K 31/166    (2006.01)
C07C 233/64    (2006.01)
(52) U.S. Cl. ...................... 514/622; 564/181
(58) Field of Classification Search ................ 514/622; 564/181
See application file for complete search history.

(56) References Cited

U.S. PATENT DOCUMENTS

| 6,218,430 | B1 | 4/2001 | Allegretto et al. |
| 2006/0094778 | A1 | 5/2006 | Nagpal et al. |
| 2006/0135484 | A1 | 6/2006 | Nagpal et al. |
| 2006/0287536 | A1 | 12/2006 | Dahnke et al. |
| 2006/0293385 | A1 | 12/2006 | Gajewski et al. |
| 2007/0105951 | A1 | 5/2007 | Gajewski et al. |
| 2007/0106095 | A1 | 5/2007 | Lu et al. |
| 2007/0149810 | A1 | 6/2007 | Lu et al. |

FOREIGN PATENT DOCUMENTS

| WO | WO 03/101978 | 12/2003 |
| WO | WO 2004/048309 A | 6/2004 |
| WO | WO 2004/063345 A | 7/2004 |
| WO | WO 2005/051898 | 6/2005 |
| WO | WO 2005/051936 | 6/2005 |
| WO | WO 2005/051938 | 6/2005 |
| WO | WO 2005/051940 | 6/2005 |
| WO | WO 2006/069153 | 6/2006 |
| WO | WO 2006/069154 | 6/2006 |

OTHER PUBLICATIONS

Masahiko Inouye, Toshiyuki Miyake, Masaru Furusyo, Hiroyuki Nakazumi: "Molecular recognition of beta-Ribofuranosides by synthetic polypyridine_macrocyclic receptors" J.Am. Chem. Soc. vol. 117, 1995, pp. 12416-12425, XP001206518.
Ping Huang, John Ramphal, James Wei, Congxin Liang, Bahija Jallal, Gerald McMahon and Cho Tang: "Structure-based design and discovery of novel inhibitors of protein tyrosine phosphatases" Bioorganic & Medicinal Chemistry, vol. 11, 2003, pp. 1835-1849, XP001206517.
Boehm, M., "Novel Nonsecosteroidal Vitamin D Mimics Exert VDR-modulating Activities" Chemistry & Biology, 1999, 265-275, vol. 6(5).
Nagpal, S. et al. "Vitamin D Analogs: Mechanism of Action of Therapeutic Applications", Curr. Med. Chem. 2001, 1661-1679, vol. 8.
Bouillon R., et al. Endocrine Rev. 1995, 200-257, vol. 16.
Swann et al. "Rational Design of Vitamin D3 Analogues Which Selectively Restore Activity to a Vitamin D Receptor Mutant Associated with Rickets" Org. Lett. 2002, p1863-3866 vol. 4.
Swann et al. "Structure-Based Design of Selective Agonists for a Rickets-Associated Mutant of the Vitamin D Receptor" J. Am. Chem. Soc. 2002 13795-13805, vol. 124.

Primary Examiner—Sharmila Gollamudi Landau
Assistant Examiner—Kortney L Klinkel
(74) Attorney, Agent, or Firm—James B. Myers

(57) ABSTRACT

The present invention relates to novel, non-secosteroidal, hydroxyl substituted, carbon-linked diaryl compounds with vitamin D receptor (VDR) modulating activity that are less hypercalcemic than 1?,25 dihydroxy vitamin D3. These compounds are useful for treating bone disease and psoriasis.

14 Claims, No Drawings

VITAMIN D RECEPTOR MODULATORS

This application is submitted as a United States national phase entry, pursuant to 35 U.S.C. 371, of PCT/US2004/037182, filed on 16 Nov. 2004, which claims the benefit of U.S. provisional patent application Ser. No. 60/523,301, filed 20 Nov. 2003, which is incorporated by reference herein.

BACKGROUND OF THE INVENTION

Vitamin $D_3$ Receptor (VDR) is a ligand dependent transcription factor that belongs to the superfamily of nuclear hormone receptors. The VDR protein is 427 amino acids, with a molecular weight of ~50 kDa. The VDR ligand, $1\alpha,25$-dihydroxyvitamin D3 (the hormonally active form of Vitamin D) has its action mediated by its interaction with the nuclear receptor known as Vitamin D receptor ("VDR"). The VDR ligand, $1\alpha,25$-dihydroxyvitamin D3 ($1\alpha,25(OH)_2D_3$) acts upon a wide variety of tissues and cells both related to and unrelated to calcium and phosphate homeostasis.

The activity $1\alpha,25$-dihydroxyvitamin D3 in various systems suggests wide clinical applications. However, use of conventional VDR ligands is hampered by their associated toxicity, namely hypercalcemia (elevated serum calcium). Currently, $1\alpha,25(OH)_2D_3$, marketed as Rocaltrol® pharmaceutical agent (product of Hoffmann-La Roche), is administered to kidney failure patients undergoing chronic kidney dialysis to treat hypocalcemia and the resultant metabolic bone disease. Other therapeutic agents, such as Calcipotriol® (synthetic analog of $1\alpha,25(OH)_2D_3$) show increased separation of binding affinity on VDR from hypercalcemic activity.

Chemical modifications of $1\alpha,25(OH)_2D_3$ have yielded analogs with attenuated calcium mobilization effects (R. Bouillon et. al., Endocrine Rev. 1995, 16, 200-257). One such analog, Dovonex® pharmaceutical agent (product of Bristol-Meyers Squibb Co.), is currently used in Europe and the United States as a topical treatment for mild to moderate psoriasis (K. Kragballe et. al., Br. J. Dermatol. 1988, 119, 223-230).

Other Vitamin $D_3$ mimics have been described in the publication, *Vitamin D Analogs: Mechanism of Action of Therapeutic Applications*, by Nagpal, S.; Lu, J.; Boehm, M. F., Curr. Med. Chem. 2001, 8, 1661-1679.

Although some degree of separation between the beneficial action and calcium raising (calcemic) effects has been achieved with these VDR ligands, to date the separation has been insufficient to allow for oral administration to treat conditions such as osteoporosis, cancers, leukemias, and severe psoriasis.

One example of a major class of disorder that could benefit from VDR mediated biological efficacy in the absence of hypercalcemia is osteoporosis. Osteoporosis is a systemic disorder characterized by decreased bone mass and microarchitectural deterioration of bone tissue leading to bone fragility and increased susceptibility to fractures of the hip, spine, and wrist (World Health Organization WHO 1994). Osteoporosis affects an estimated 75 million people in the United States, Europe, and Japan.

Within the past few years, several antiresorptive therapies have been introduced. These include bisphosphonates, hormone replacement therapy (HRT), a selective estrogen receptor modulator (SERM), and calcitonins. These treatments reduce bone resorption, bone formation, and increase bone density. However, none of these treatments increase true bone volume nor can they restore lost bone architecture.

Another major disorder that could benefits from VDR mediated biological activity is psoriasis. Psoriasis is one of the most common dermatologic diseases and is a chronic inflammatory skin condition characterized by erythematous, sharply demarcated papules and rounded plaques, covered by silvery micaceous scale.

Synthetic VDR ligands with reduced calcemic potential have been synthesized. For example, a class of bis-phenyl compounds stated to mimic $1\alpha,25$-dihydroxyvitamin $D_3$ is described in U.S. Pat. No. 6,218,430 and the article, "Novel nonsecosteroidal vitamin D mimics exert VDR-modulating activities with less calcium mobilization than $1\alpha,25$-Dihydroxyvitamin $D_3$" by Marcus F. Boehm, et. al., *Chemistry & Biology* 1999, Vol 6, No. 5, pgs. 265-275.

Synthetic VDR ligands having an aryl-thiophene nucleus are described in U.S. provisional patent application Ser. No. 60/384,151, filed 29 May 2002.

There remains a need for improved treatments using alternative or improved pharmaceutical agents that mimic $1\alpha,25$-dihydroxyvitamin $D_3$ to stimulate bone formation, restore bone quality, and treat other diseases without the attendant disadvantage of hypercalcemia.

SUMMARY OF THE INVENTION

Novel compounds having a nucleus of formula "(A)" have been found effective as Vitamin D Receptor (VDR) modulators:

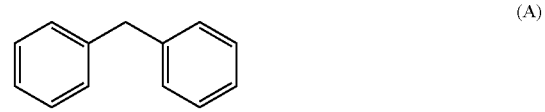

(A)

The compounds of the invention with VDR modulating activities are represented by formula (I)

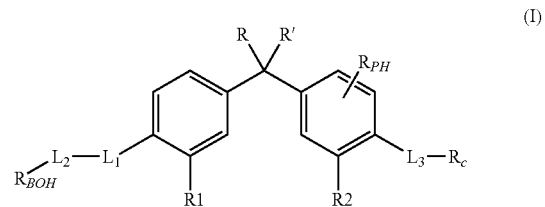

(I)

wherein the variables R, R', $R_{PH}$, R1, R2, $L_1$, $L_2$, $L_3$, $R_{BOH}$, and $R_C$ are as hereinafter defined. It is a discovery of this invention that compounds described herein display the desirable cell differentiation and antiproliferative effects of 1,25 $(OH)_2D_3$ with reduced calcium mobilization (calcemic) effects if substituent $R_{BOH}$ bears a hydroxyl group and substituent $R_C$ possesses a carbon atom linked group directly bonded (i.e., with no intervening non-carbon atom) to the aryl nucleus.

In another aspect, the present invention is directed towards pharmaceutical compositions containing pharmaceutically effective amounts of compounds of formulae (I) or a pharmaceutically acceptable salt or prodrug thereof, either singly or in combination, together with pharmaceutically acceptable carriers and/or auxiliary agents.

Another aspect of the invention is a pharmaceutical formulation for treatment or prevention of osteoporosis containing pharmaceutically effective amounts of the vitamin D receptor modulator compound of formula (I) alone or together with pharmaceutically effective amounts of co-agents conventionally used for the treatment of osteoporosis.

Another aspect of the invention is a pharmaceutical formulation for treatment or prevention of psoriasis containing pharmaceutically effective amounts of the vitamin D receptor modulator compound of formula (I) alone or together with pharmaceutically effective amounts of co-agents conventionally used for the treatment of psoriasis.

Another aspect of the invention is a pharmaceutical formulation for treatment or prevention of prostate cancer containing pharmaceutically effective amounts of the vitamin D receptor modulator compound of formula (I) alone or together with pharmaceutically effective amounts of co-agents conventionally used for the treatment of prostate cancer.

Another aspect of the invention is to use the compounds of the invention to treat disease states responsive to Vitamin D receptor ligands.

Another aspect of the invention is the prevention and treatment of acne, actinic keratosis, alopecia, Alzheimer's disease, autoimmune induced diabetes, bone fracture healing, breast cancer, Crohn's disease, prostate cancer, benign prostatic hyperplasia, bladder cancer, colon cancer, Type I diabetes, host-graft rejection, hypercalcemia, Type II diabetes, leukemia, multiple sclerosis, insufficient sebum secretion, osteomalacia, osteoporosis, insufficient dermal firmness, insufficient dermal hydration, myelodysplastic syndrome, psoriatic arthritis, psoriasis, renal osteodystrophy, rheumatoid arthritis, scleroderma, seborrheic dermatitis, skin cancer, systemic lupus erythematosis, skin cell protection from Mustard vesicants, ulcerative colitis, and wrinkles; by administering to a mammal in need thereof a pharmaceutically effective amount of a compound of Formula I.

DETAILED DESCRIPTION OF THE INVENTION

Definitions:

The term, "abscess" refers to adverse complications often associated with surgery, trama, or diseases that predispose the host to abscess formation from encapsulated bacteria lymphocytes, macrophages, and etc.

The term, "adhesion" refers to the adverse and abnormal union of surfaces normally separate by the formation of new fibrous tissue resulting from an inflammatory process.

The term, "compound of the invention" refers to a compound represented by any of (i) formulae I, II, III and its preferred embodiments, (ii) the product of any example set out herein, or (iii) a compound identified in the species coded AA-1 to AA-33, BB-1 to BB-33, CC-1 to CC-44, or a salt or prodrug derivative of (i), (ii), or (iii).

The term, "Active Ingredient" means a compound of the invention.

The term, "Mustard" is inclusive of both sulfur mustards and nitrogen mustards, either alone or in any combination. Exemplary of such compounds are the vesicants; bis(2-chloroethyl) sulfide (Chemical Agent Symbol HD), Cl(CH$_2$)$_2$S(CH$_2$)$_2$Cl 1,2-bis(2-chloroethylthio)ethane (Chemical Agent Symbol Q), Cl(CH$_2$)$_2$S(CH$_2$)$_2$S(CH$_2$)$_2$Cl; bis(2-chloroethylthioethyl)ether, Cl(CH$_2$)$_2$S(CH$_2$)$_2$O(CH$_2$)$_2$S(CH$_2$)$_2$Cl (Chemical Agent Symbol T); tris(2-chloroethyl) amine (Chemical Agent Symbol HN3) N(CH$_2$CH$_2$Cl)$_3$; N-methyl-2,2'-dichlorodiethylamine (Chemical Agent Symbol NH2); and 2,2'-dichlorotriethylamine, CH$_3$CH$_2$N(CH$_2$CH$_2$Cl)$_2$ (Chemical Agent Symbol NH1).

The term, "(Acidic Group)" means an organic group that acts as a proton donor capable of hydrogen bonding. Illustrative of an (Acidic Group) is a group selected from the following:

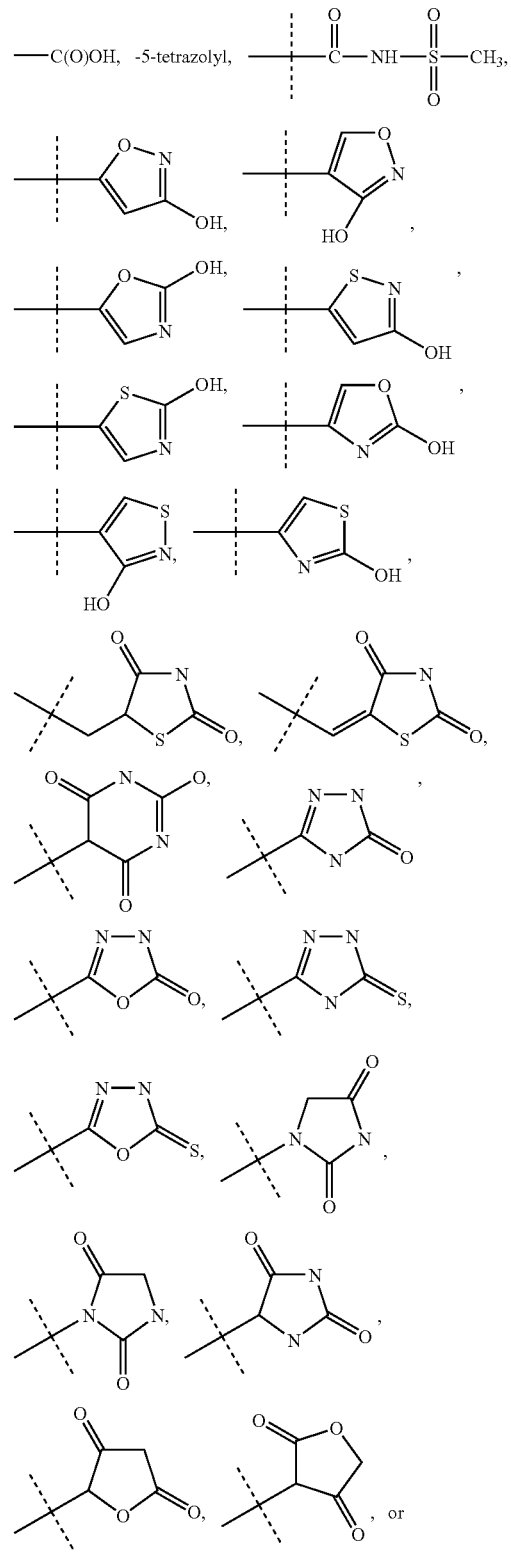

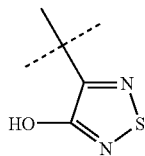

The term, "carbon atom linked group" is used to identify the chemical substituent R_C in the Formula I definition of compounds of the invention. Its defining characteristic is a carbon atom as the first atom and point of attachment to the aryl ring to which it is attached. For example in the structural formula (C):

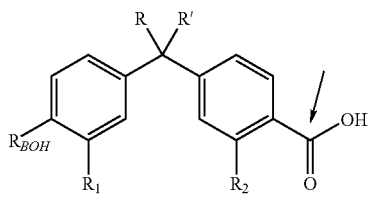

(C)

the arrow identifies the carbon atom linked directly to the aryl nucleus of formula (I). All compounds of the invention contain a carbon atom linked group as the $R_C$ substituent.

The term "alkenyl" refers to aliphatic groups wherein the point of attachment is a carbon-carbon double bond, for example vinyl, 1-propenyl, and 1-cyclohexenyl. Alkenyl groups may be straight-chain, branched-chain, cyclic, or combinations thereof, and may be optionally substituted. Suitable alkenyl groups have from 2 to about 20 carbon atoms.

The term "$C_1$-$C_5$ alkyl" refers to saturated aliphatic groups including straight-chain, branched-chain, and cyclic groups and any combinations thereof. Examples of $C_1$-$C_5$ alkyl groups are methyl; ethyl; n-propyl; 1-methylethyl; n-butyl; 1-methylpropyl; 2-methylpropyl; n-amyl; 1,1-dimethylpropyl; 1,2-dimethylpropyl; and 2,2-dimethylpropyl.

The term "cycloalkyl" includes organic radicals such as cyclopropyl, cyclobutyl, cyclopentyl and cyclohexyl.

The term, "cycloalkenyl" includes organic radicals such as cyclopropenyl, cyclobutenyl, cyclopentenyl and cyclohexenyl.

The term, "$C_1$-$C_5$ fluoroalkyl" is an alkyl group containing fluorine and includes organic radicals such as —$CF_3$, —$CHF_2$, —$CH_2F$, —$CF_2CF_3$, —$CHFCF_3$, —$CH_2CF_3$, —$CH_2CHF_2$, and —$CH_2CH_2F$, with —$CF_3$ being preferred.

The term, "-1,3-thiazolidine-2,4-dione-5-methylidene", refers to the radical represented by the structural formula:

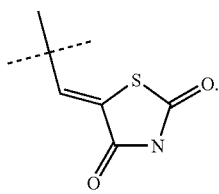

The term, "—$CH_2$—C(O)—N-pyrrolidine" refers to the radical represented by the structural formula:

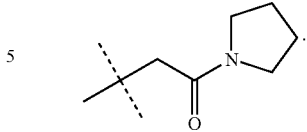

The term, "—$CH_2$—N-pyrrolidin-2-one" refers to the radical represented by the structural formula:

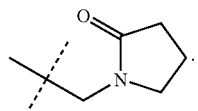

The term, "—$CH_2$-(1-methylpyrrolidin-2-one-3-yl)" refers to the organic radical represented by the structural formula:

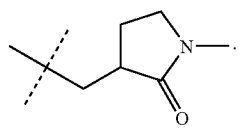

The term, "1,3,4-oxadiazolin-2-one-5-yl" refers to the organic radical represented by the structural formula:

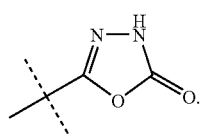

The term, "1,3,4-oxadiazolin-2-thione-5-yl" refers to the organic radical represented by the structural formula:

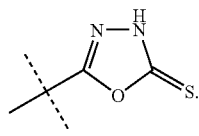

The term, "imidazolidine-2,4-dione-5-yl" refers to the organic radical represented by the structural formula:

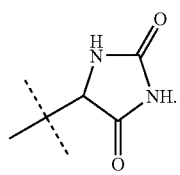

The term, "isoxazol-3-ol-5-yl" refers to the organic radical represented by the structural formula:

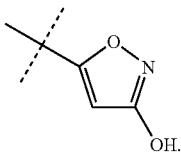

The dotted line symbol crossing a solid line representing a bond

The univalent symbol "—O" in any structural formula is a hydroxyl group (—OH). means that the bond so marked is the bond of attachment, for example, the group;

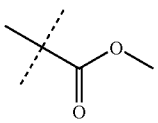

is attached to a phenyl ring of the parent diaryl nucleus to provide a compound of the invention as shown;

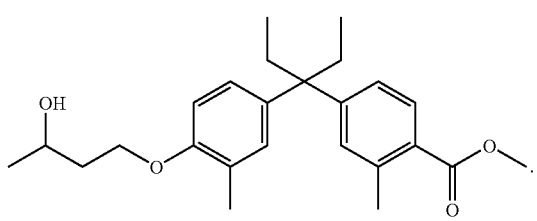

The term, "mammal" includes humans.
The term "halo" refer to fluorine, chlorine, bromine, and iodine.
The term, "terminal hydroxyalkyl" is a group selected from
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
1-hydroxycycloalkenyl; and
1-hydroxycycloalkyl.
The term, "3-methyl-3-hydroxypentyl" refers to the radical having the structural formula:

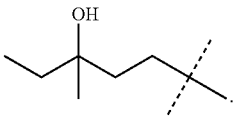

The term, "3-methyl-3-hydroxypentenyl" refers to the radical having the structural formula (both cis and trans isomers):

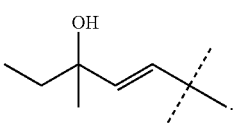

The term, "3-methyl-3-hydroxypentynyl" refers to the radical having the structural formula:

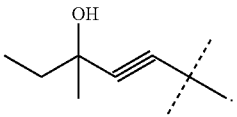

The term, "3-ethyl-3-hydroxypentyl" refers to the radical having the structural formula:

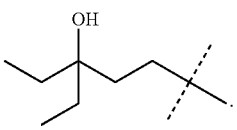

The term, "3-ethyl-3-hydroxypentenyl" refers to the radical having the structural formula (both cis and trans isomers):

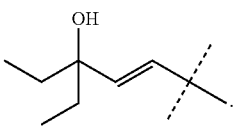

The term, "3-ethyl-3-hydroxypentynyl" refers to the radical having the structural formula:

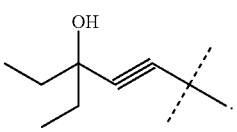

The term, "3-propyl-3-hydroxypentyl" refers to the radical having the structural formula:

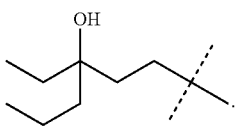

The term, "3-propyl-3-hydroxypentenyl" refers to the radical having the structural formula (both cis and trans isomers):

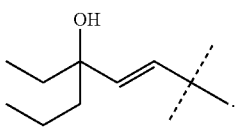

The term, "3-propyl-3-hydroxypentynyl" refers to the radical having the structural formula:

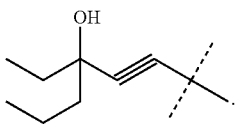

The term, "3-ethyl-3-hydroxy-4-methylpentyl" refers to the radical having the structural formula:

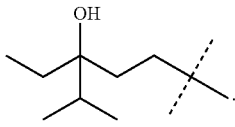

The term, "3-ethyl-3-hydroxy-4-methylpentenyl" refers to the radical having the structural formula (both cis and trans isomers):

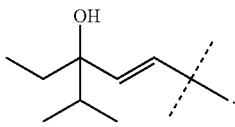

The term, "3-ethyl-3-hydroxy-4-methylpentynyl" refers to the radical having the structural formula:

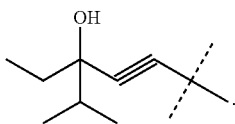

The term, "1-hydroxy-2-methyl-1-(methylethyl)propyl" refers to the radical having the structural formula:

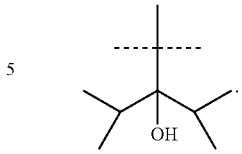

The term, "1-hydroxycycloalkenyl" refers to a radical selected from 1-hydroxycyclopentenyl, 1-hydroxycyclohexenyl, 1-hydroxycycloheptenyl, or 1-hydroxycyclooctenyl.

The term "hydroxycycloalkyl" refers to a radical having the general structural formula:

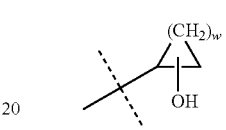

where w is an integer from 1 to 6 and the hydroxyl radical is substituted on any ring carbon atom.

The term "1-hydroxycycloalkyl" refers to a radical having the general structural formula:

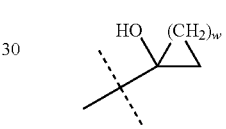

Examples of 1-hydroxycycloalkyl radicals are
1-hydroxycyclopropyl, 1-hydroxycyclobutyl, 1-hydroxycyclopentyl,
1-hydroxycyclohexyl, 1-hydroxycycloheptyl, and 1-hydroxycyclooctyl.

The abbreviation, "Me" means methyl.
The abbreviation, "Et" means ethyl.
The abbreviation, "iPr" means 1-methylethyl.
The abbreviation, "nPr" means n-propyl.
The abbreviation, "3Me3OH-Pentyl" means 3-methyl-3-hydroxypentyl.
The abbreviation, "3Me3OH-Pentenyl" means 3-methyl-3-hydroxypentenyl
The abbreviation, "3Me3OH-Pentynyl" means 3-methyl-3-hydroxypentynyl
The abbreviation, "3Et3OH-Pentyl" means 3-ethyl-3-hydroxypentyl.
The abbreviation, "3Et3OH-Pentenyl" means 3-ethyl-3-hydroxypentenyl
The abbreviation, "3Et3OH-Pentynyl" means 3-ethyl-3-hydroxypentynyl
The abbreviation, "3Pr3OH-Pentyl" means 3-propyl-3-hydroxypentyl.
The abbreviation, "3Pr3OH-Pentenyl" means 3-propyl-3-hydroxypentenyl.
The abbreviation, "3Pr3OH-Pentynyl" means 3-propyl-3-hydroxypentynyl.
The abbreviation, "3Et3OH4Me-Pentyl" means 3-ethyl-3-hydroxy-4-methylpentyl.
The abbreviation, "3Et3OH4Me-Pentenyl" means 3-ethyl-3-hydroxy-4-methylpentenyl, The abbreviation, "3Et3OH4Me-Pentynyl" means 3-ethyl-3-hydroxy-4-methylpentynyl.

The abbreviation, "1OH2Me1MeEt-Propyl" means 1-hydroxy-2-methyl-1-(methylethyl)propyl.

Compounds of the Invention:

The compounds of the invention with vitamin receptor modulating (VDRM) activities are represented by formula (I) or a pharmaceutically acceptable salt or a prodrug derivative thereof:

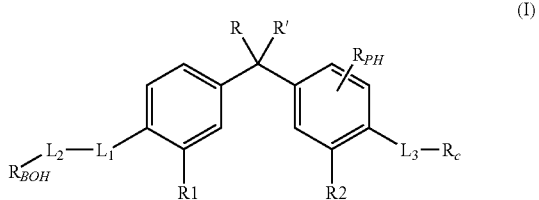

(I)

wherein;

R and R' are independently $C_1$-$C_5$ alkyl, $C_1$-$C_5$ fluoroalkyl, or together R and R' form a substituted or unsubstituted, saturated or unsaturated carbocyclic ring having from 3 to 8 carbon atoms;

$R_{PH}$ is hydrogen or methyl;

R1 and R2 are independently selected from the group consisting of hydrogen, halo, $C_1$-$C_5$ alkyl, $C_1$-$C_5$ fluoroalkyl, —O—$C_1$-$C_5$ alkyl, —S—$C_1$-$C_5$ alkyl, —O—$C_1$-$C_5$ fluoroalkyl, —CN, —$NO_2$, acetyl, —S—$C_1$-$C_5$ fluoroalkyl, $C_2$-$C_5$ alkenyl, $C_3$-$C_5$ cycloalkyl, and $C_3$-$C_5$ cycloalkenyl;

$L_1$ and $L_2$ and $L_3$ are independently divalent linking groups independently selected from the group consisting of a bond,

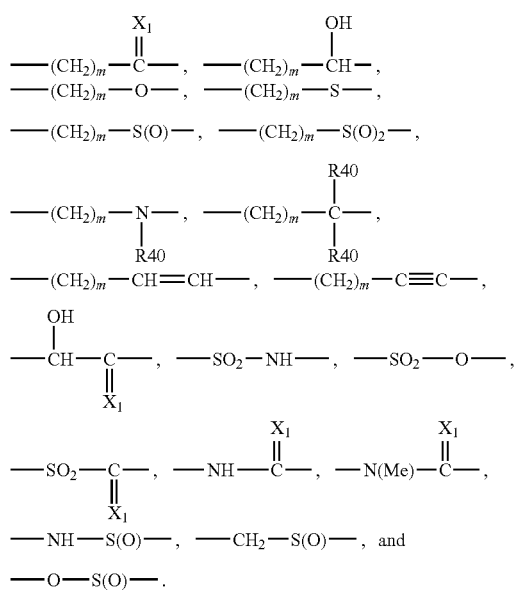

where m is 0, 1, or 2; $X_1$ is oxygen or sulfur, and each R40 is independently hydrogen, $C_1$-$C_5$ alkyl, or $C_1$-$C_5$ fluoroalkyl;

$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl
1-hydroxycyclopentenyl,
1-hydroxycyclohexenyl,
1-hydroxycycloheptenyl,
1-hydroxycyclooctenyl,
1-hydroxycyclopropyl,
1-hydroxycyclobutyl,
1-hydroxycyclopentyl,
1-hydroxycyclohexyl,
1-hydroxycycloheptyl, or
1-hydroxycyclooctyl;

provided that when
$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl, or
1-hydroxy-2-methyl-1-(methylethyl)propyl;

then $L_1$ and $L_2$ combine as a bond; and
$R_C$ is
—$CO_2$H,
—$CO_2$Me,
—$CO_2$Et,
—C(O)$CH_2$S(O)Me,
—C(O)$CH_2$S(O)Et,
—C(O)$CH_2$S(O)$_2$Me,
—C(O)$CH_2$S(O)$_2$Et,
—C(O)$CH_2CH_2$S(O)Me,
—C(O)$CH_2CH_2$S(O)Et,
—C(O)$CH_2CH_2$S(O)$_2$Me,
—C(O)$CH_2CH_2$S(O)$_2$Et,
—C(O)CHMe$CH_2CO_2$H
—C(O)C(O)OH,
—C(O)C(O)$NH_2$,
—C(O)C(O)NHMe,
—C(O)C(O)$NMe_2$,
—C(O)$NH_2$, C(O)$NMe_2$,
—C(O)NHS(O)Me,
—C(O)NHS$O_2$Me,
—C(O)—NH-5-tetrazolyl,
—C(O)NMe-5-tetrazolyl,
—C(O)NHS(O)Me,
—C(O)NHS(O)Et,
—C(O)NHS$O_2$Me,
—C(O)NHS$O_2$Et,
C(O)NHS(O)iPr,
—C(O)NHS$O_2$iPr,
—C(O)NHS(O)nPr, —C(O)NHSO₂nPr,
—C(O)NHCH₂S(O)Me,
—C(O)NHCH₂S(O)Et,
—C(O)NHCH₂SO₂Me,
—C(O)NHCH₂SO₂Et,
—C(O)NHCH₂CH₂S(O)Me,
—C(O)NHCH₂CH₂S(O)Et,
—C(O)NHCH₂CH₂SO₂Me,
—C(O)NHCH₂CH₂SO₂Et,
—C(O)NH₂,
—C(O)NMe₂,
—C(O)NH—CH₂—C(O)OH,
—C(O)NH—CH(Me)-C(O)OH,
—C(O)NH—CH(F)—C(O)OH,
—C(O)NH—CH(CF₃)—C(O)OH,
—C(O)NH—CH(OH)—C(O)OH,
—C(O)NH—CH(cyclopropyl)-C(O)OH,
—C(O)NH—C(Me)₂-C(O)OH,
—C(O)NH—C(Me)₂-C(O)OH,
—C(O)NH—CF(Me)-C(O)OH,
—C(O)NH—C(Me)(CF₃)—C(O)OH,
—C(O)NH—C(Me)(OH)—C(O)OH,
—C(O)NH—C(Me)(cyclopropyl-C(O)OH,
—C(O)NMe-C(O)OH,
—C(O)NMe-CH(Me)-C(O)OH,
—C(O)NMe-CH(F)—C(O)OH,
—C(O)NMe-CH(CF₃)—C(O)OH,
—C(O)NMe-CH(OH)—C(O)OH,
—C(O)NMe-CH(cyclopropyl)-C(O)OH,
—C(O)NMe-C(Me)₂-C(O)OH,
—C(O)NMe-CF(Me)-C(O)OH,
—C(O)NMe-C(Me)(CF₃)—C(O)OH,
—C(O)NMe-C(Me)(OH)—C(O)OH,
—C(O)NMe-C(Me)(cyclopropyl)-C(O)OH,
—CH₂—CO₂H,
—CH₂-5-tetrazolyl,
—CH₂CO₂Me,
—CH₂CO₂Et,
—CH₂NHS(O)Me,
—CH₂NHS(O)Et,
—CH₂NHSO₂Me,
—CH₂NHSO₂Et,
—CH₂NHS(O)iPr,
—CH₂NHSO₂iPr,
—CH₂NHS(O)nPr,
—CH₂NHSO₂nPr,
—CH₂NHCH₂CH₂SO₂CH₃,
—CH₂NH(CH₂CO₂H),
—CH₂N(C(O)Me)(CH₂CO₂H),
—CH₂—N-pyrrolidin-2-one,
—CH₂-(1-methylpyrrolidin-2-one-3-yl),
—CH₂S(O)Me,
—CH₂S(O)Et,
—CH₂S(O)₂Me,
—CH₂S(O)₂Et,
—CH₂S(O)iPr,
—CH₂S(O)₂iPr,
—CH₂S(O)nPr,
—CH₂S(O)₂nPr,
—CH₂CO₂H, CH₂C(O)NH₂,
—CH₂C(O)NMe₂,
—CH₂C(O)NHMe,
—CH₂C(O)—N-pyrrolidine,
—CH₂S(O)₂Me,
—CH₂S(O)Me,
—CH(OH)CO₂H,
—CH(OH)C(O)NH₂,
—CH(OH)C(O)NHMe,
—CH(OH)C(O)NMe₂,
—CH(OH)C(O)NEt₂,
—CH₂CH₂CO₂H,
—CH₂CH₂CO₂Me,
—CH₂CH₂CO₂Et,
—CH₂CH₂C(O)NH₂,
—CH₂CH₂C(O)NHMe,
—CH₂CH₂C(O)NMe₂,
—CH₂CH₂-5-tetrazolyl,
—CH₂CH₂S(O)₂Me,
—CH₂CH₂S(O)Me,
—CH₂CH₂S(O)₂Et,
—CH₂CH₂S(O)Et,
—CH₂CH₂S(O)iPr,
—CH₂CH₂S(O)₂iPr,
—CH₂CH₂S(O)nPr,
—CH₂CH₂S(O)₂nPr,
—CH₂CH₂S(O)NH₂,
—CH₂CH₂S(O)NHMe,
—CH₂CH₂S(O)NMe₂,
—CH₂CH₂S(O)₂NH₂,
—CH₂CH₂S(O)₂NHMe,
—CH₂CH₂S(O)₂NMe₂,
—CH₂CH₂CH₂S(O)Me,
—CH₂CH₂CH₂S(O)Et,
CH₂CH₂CH₂S(O)₂Me,
—CH₂CH₂CH₂S(O)₂Et,
—CH(Me)CH₂C(O)OH,
—C(Me)₂CH₂C(O)OH,
—SO₃H,
-5-tetrazolyl,

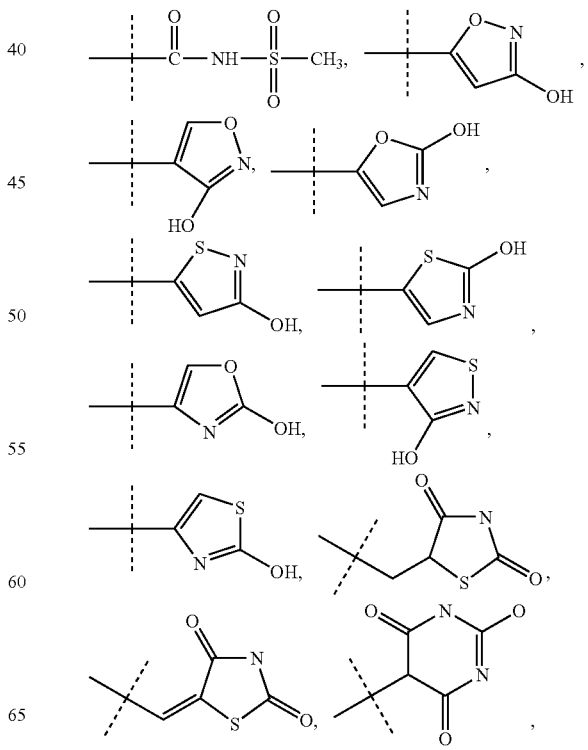

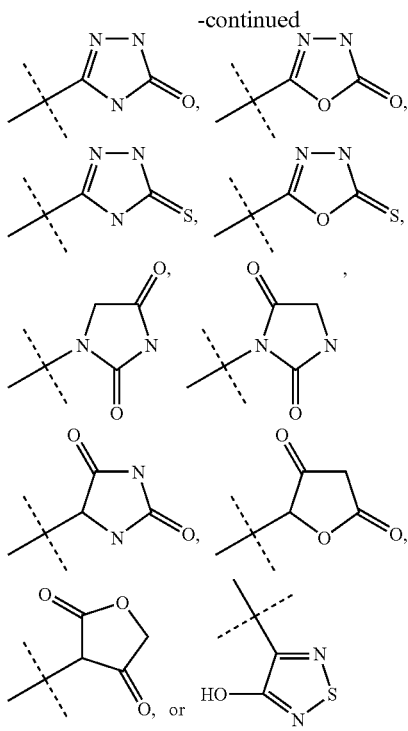

1,3,4-oxadiazolin-2-one-5-yl,
-imidazolidine-2,4-dione-5-yl,
-1,3-thiazolidine-2,4-dione-5-methylidene,
-isoxazol-3-ol-yl, or
-1,3,4-oxadiazolin-2-thione-5-yl.

The combination of $L_1$ and $L_2$ as a bond (divalent linking group) is understood to mean that group $R_{BOH}$, is attached directly to the phenyl nucleus, for example, as in the following structural formula:

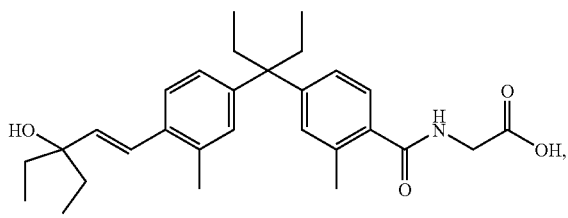

where $R_{BOH}$ is 3-ethyl-3-hydroxypentenyl.

Preferred compounds of the invention with VDR modulating activities are represented by formula (II) or a pharmaceutically acceptable salt or an ester prodrug derivative thereof:

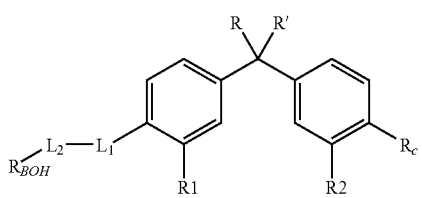

(II)

wherein;

R and R' are independently methyl or ethyl;

R1 and R2 are independently hydrogen, halo, —$CF_3$, methyl, ethyl, or cyclopropyl;

$L_1$ and $L_2$ are independently divalent linking groups independently selected from
a bond,

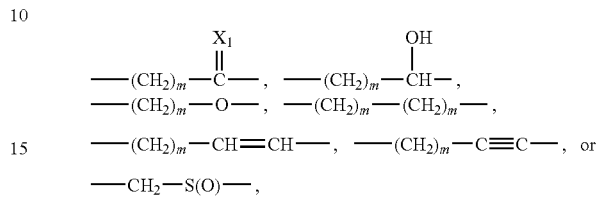

where m is 0 or 1;

$R_{BOH}$ is selected from
1-hydroxycycyclopentenyl,
1-hydroxycyclohexenyl,
1-hydroxycyclopentyl, or
1-hydroxycyclohexyl, and $Z_C$ is a group selected from
—$CO_2H$,
—$CO_2Me$,
—$CO_2Et$,
—C(O)$NH_2$,
—C(O)$NMe_2$,
—C(O)NH—$CH_2$—C(O)OH,
—C(O)NH—CH(Me)-C(O)OH,
—C(O)NH—CH(F)—C(O)OH,
—C(O)NH—CH($CF_3$)—C(O)OH,
—C(O)NH—CH(OH)—C(O)OH,
—C(O)NH—CH(cyclopropyl)-C(O)OH,
—C(O)NH—C(Me)$_2$-C(O)OH,
—C(O)NH—C(Me)$_2$-C(O)OH,
—C(O)NH—CF(Me)-C(O)OH,
—C(O)NH—C(Me)($CF_3$)—C(O)OH,
—C(O)NH—C(Me)(OH)—C(O)OH,
—C(O)NH—C(Me)(cyclopropyl-C(O)OH,
—C(O)NMe-$CH_2$—C(O)OH,
—C(O)NMe-CH(Me)-C(O)OH,
—C(O)NMe-CH(F)—C(O)OH,
—C(O)NMe-CH($CF_3$)—C(O)OH,
—C(O)NMe-CH(OH)—C(O)OH,
—C(O)NMe-CH(cyclopropyl)-C(O)OH,
—C(O)NMe-C(Me)$_2$-C(O)OH,
—C(O)NMe-CF(Me)-C(O)OH,
—C(O)NMe-C(Me)($CF_3$)—C(O)OH,
—C(O)NMe-C(Me)(OH)—C(O)OH,
—C(O)NMe-5-tetrazolyl,
—C(O)NMe-C(Me)(cyclopropyl)-C(O)OH, or
—C(O)—NH-5-tetrazolyl.

Preferred compounds of the invention with VDR modulating activities are represented by formula (III) or a pharmaceutically acceptable salt or an ester prodrug derivative thereof:

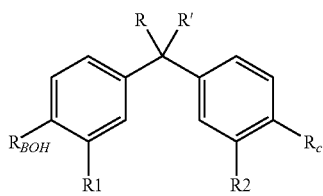

(III)

wherein;

R and R' are independently methyl or ethyl;

$R_1$ and $R_2$ are independently hydrogen, halo, —$CF_3$, methyl, ethyl, or cyclopropyl;

$R_{BOH}$ is selected from
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-propyl-3-hydroxypentyl,
3-propyl-3-hydroxypentynyl,
3-propyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl, or
1-hydroxy-2-methyl-1-(methylethyl)propyl; and $Z_C$ is a group selected from
—$CO_2H$,
—$CO_2Me$,
—$CO_2Et$,
—C(O)$NH_2$,
—C(O)$NMe_2$,
—C(O)NH—$CH_2$—C(O)OH,
—C(O)NH—CH(Me)-C(O)OH,
—C(O)NH—CH(F)—C(O)OH,
—C(O)NH—CH($CF_3$)—C(O)OH,
—C(O)NH—CH(OH)—C(O)OH,
—C(O)NH—CH(cyclopropyl)-C(O)OH,
—C(O)NH—C(Me)$_2$-C(O)OH,
—C(O)NH—C(Me)$_2$-C(O)OH,
—C(O)NH—CF(Me)-C(O)OH,
—C(O)NH—C(Me)($CF_3$)—C(O)OH,
—C(O)NH—C(Me)(OH)—C(O)OH,
—C(O)NH—C(Me)(cyclopropyl-C(O)OH,
—C(O)NMe-$CH_2$—C(O)OH,
—C(O)NMe-CH(Me)-C(O)OH,
—C(O)NMe-CH(F)—C(O)OH,
—C(O)NMe-CH($CF_3$)—C(O)OH,
—C(O)NMe-CH(OH)—C(O)OH,
—C(O)NMe-CH(cyclopropyl)-C(O)OH,
—C(O)NMe-C(Me)$_2$-C(O)OH,
—C(O)NMe-CF(Me)-C(O)OH,
—C(O)NMe-C(Me)($CF_3$)—C(O)OH,
—C(O)NMe-C(Me)(OH)—C(O)OH,
—C(O)NMe-5-tetrazolyl,
—C(O)NMe-C(Me)(cyclopropyl)-C(O)OH, or
—C(O)—NH-5-tetrazolyl.

Particularly preferred salts of the compounds Formulae I and III are sodium and potassium.

Particularly preferred ester prodrugs of the compounds of Formulae I and II and III are the methyl ester, ethyl ester, N,N-diethylglycolamido ester, and the morpholinylethyl ester.

Particularly preferred are compounds or a pharmaceutically acceptable salt or prodrug derivative thereof selected from (AA-1) to (AA-33) and mixtures thereof, as follows:

AA-1)
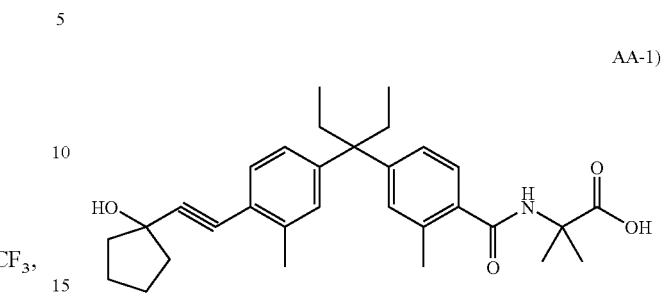

AA-2)
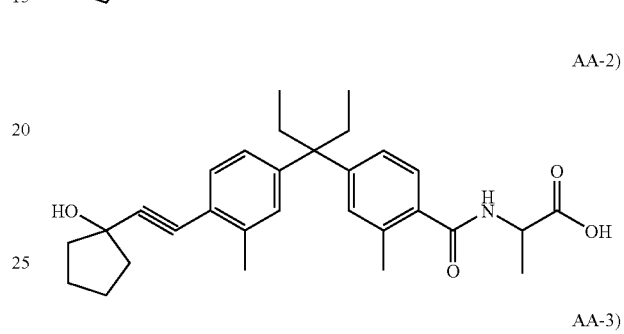

AA-3)
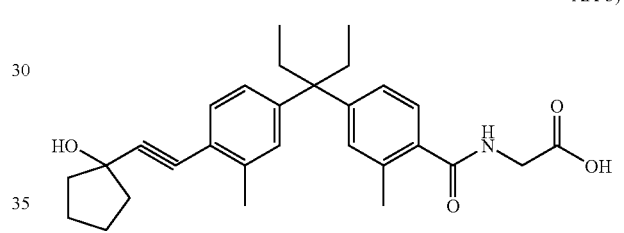

AA-4)
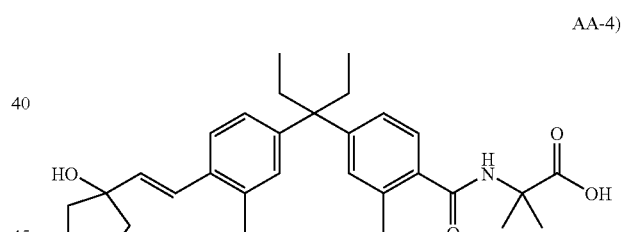

AA-5)
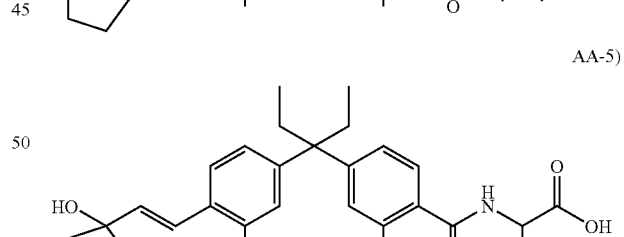

AA-6)
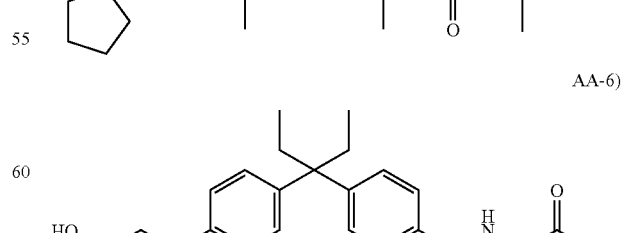

-continued

AA-7)
AA-8)
AA-9)
AA-10)
AA-11)
AA-12)

-continued

AA-13)
AA-14)
AA-15)
AA-16)
AA-17)
AA-18)

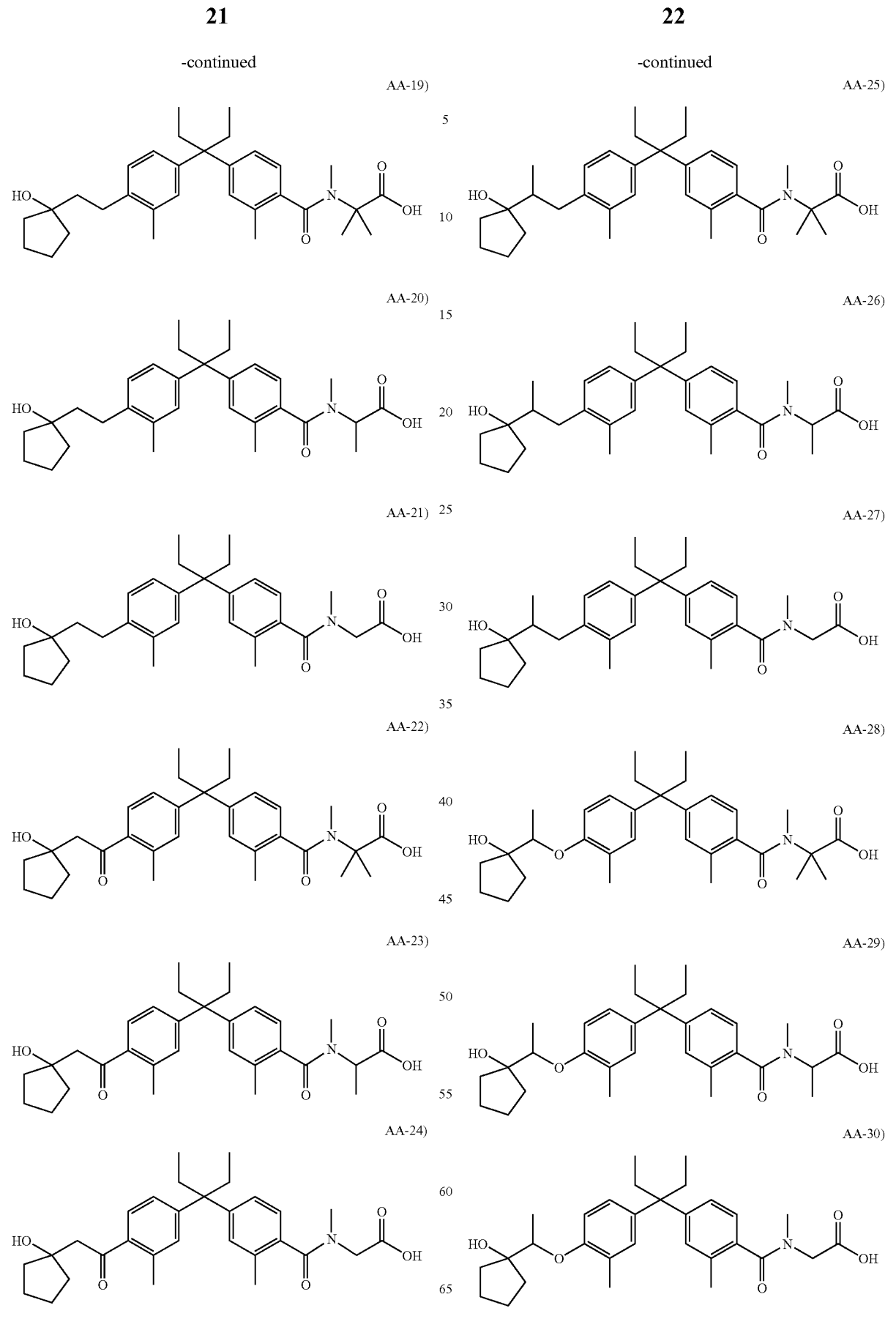

-continued

AA-19)
AA-20)
AA-21)
AA-22)
AA-23)
AA-24)

-continued

AA-25)
AA-26)
AA-27)
AA-28)
AA-29)
AA-30)

-continued
AA-31)
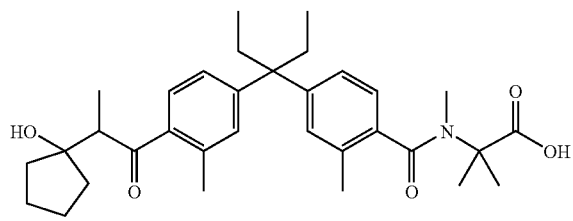
AA-32)
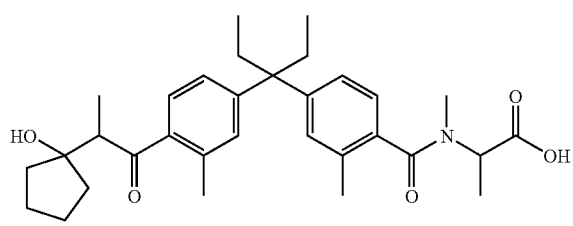
AA-33)
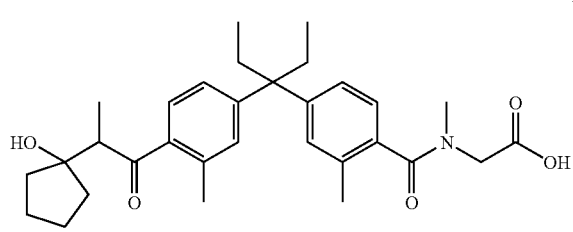
Additional particularly preferred are compounds or a pharmaceutically acceptable salt or prodrug derivative thereof selected from (BB-1) to (BB-33) and mixtures thereof, as follows:
BB-1)
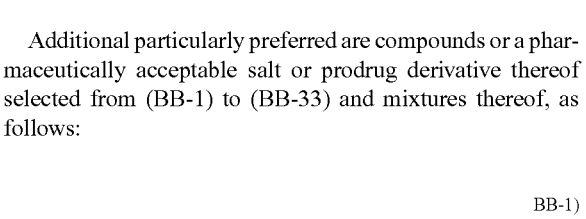
BB-2)
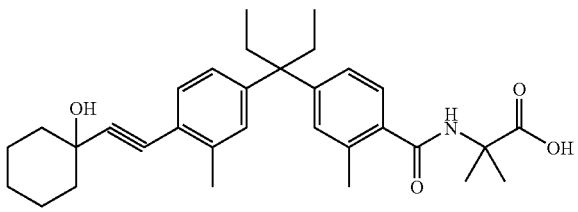
BB-3)
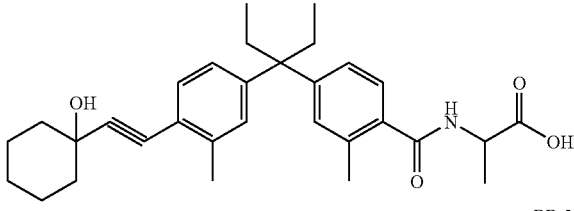
-continued
BB-4)
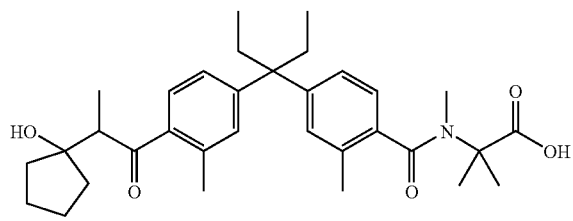
BB-5)
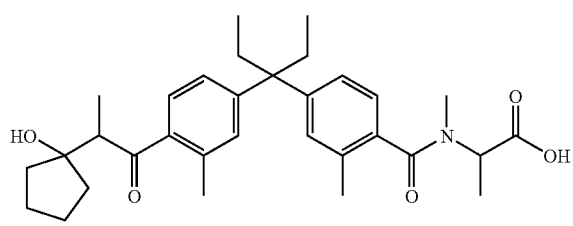
BB-6)
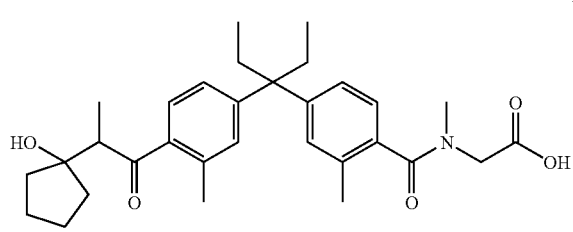
BB-7)
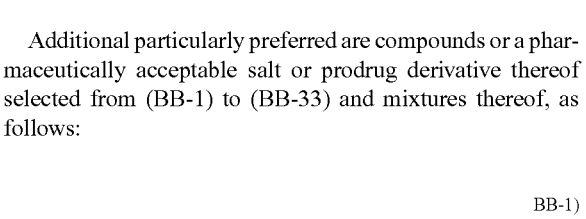
BB-8)
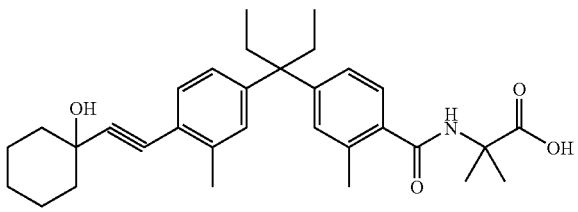
BB-9)
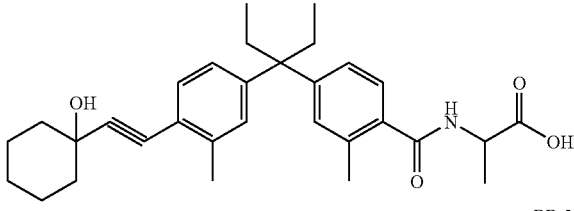
BB-10)
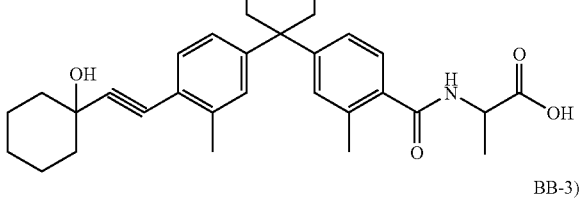

-continued

BB-11)
BB-12)
BB-13)
BB-14)
BB-15)
BB-16)
BB-17)

-continued

BB-18)
BB-19)
BB-20)
BB-21)
BB-22)
BB-23)
BB-24)

-continued
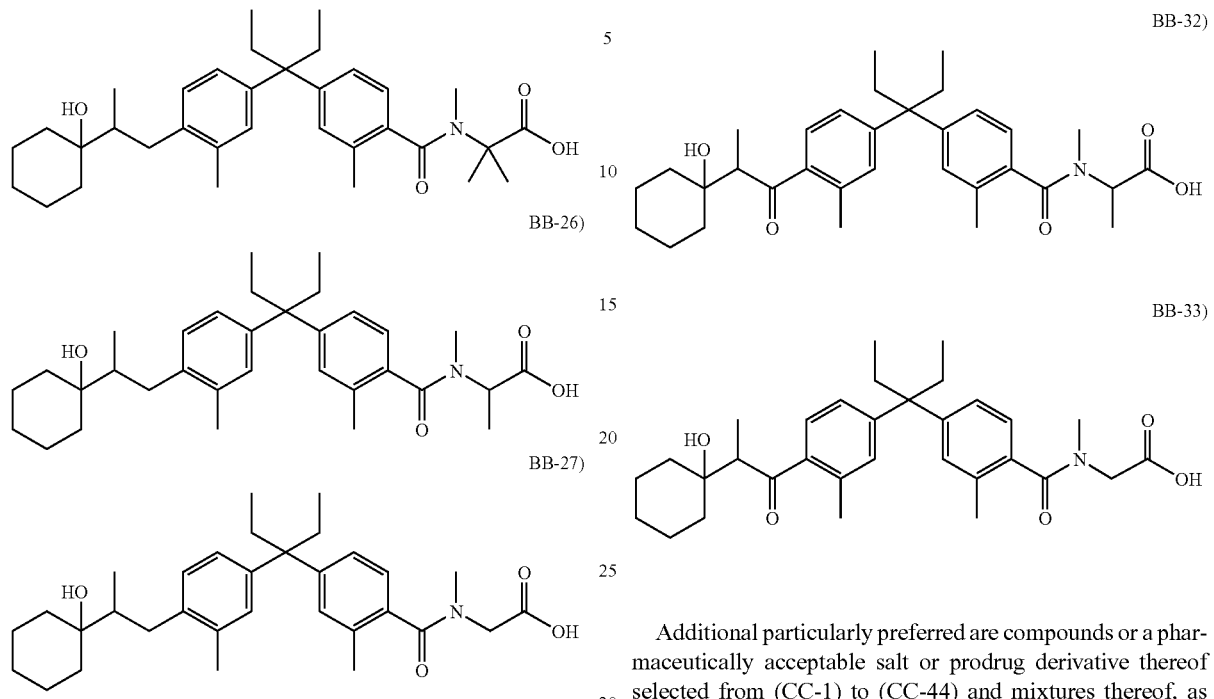
Additional particularly preferred are compounds or a pharmaceutically acceptable salt or prodrug derivative thereof selected from (CC-1) to (CC-44) and mixtures thereof, as follows:
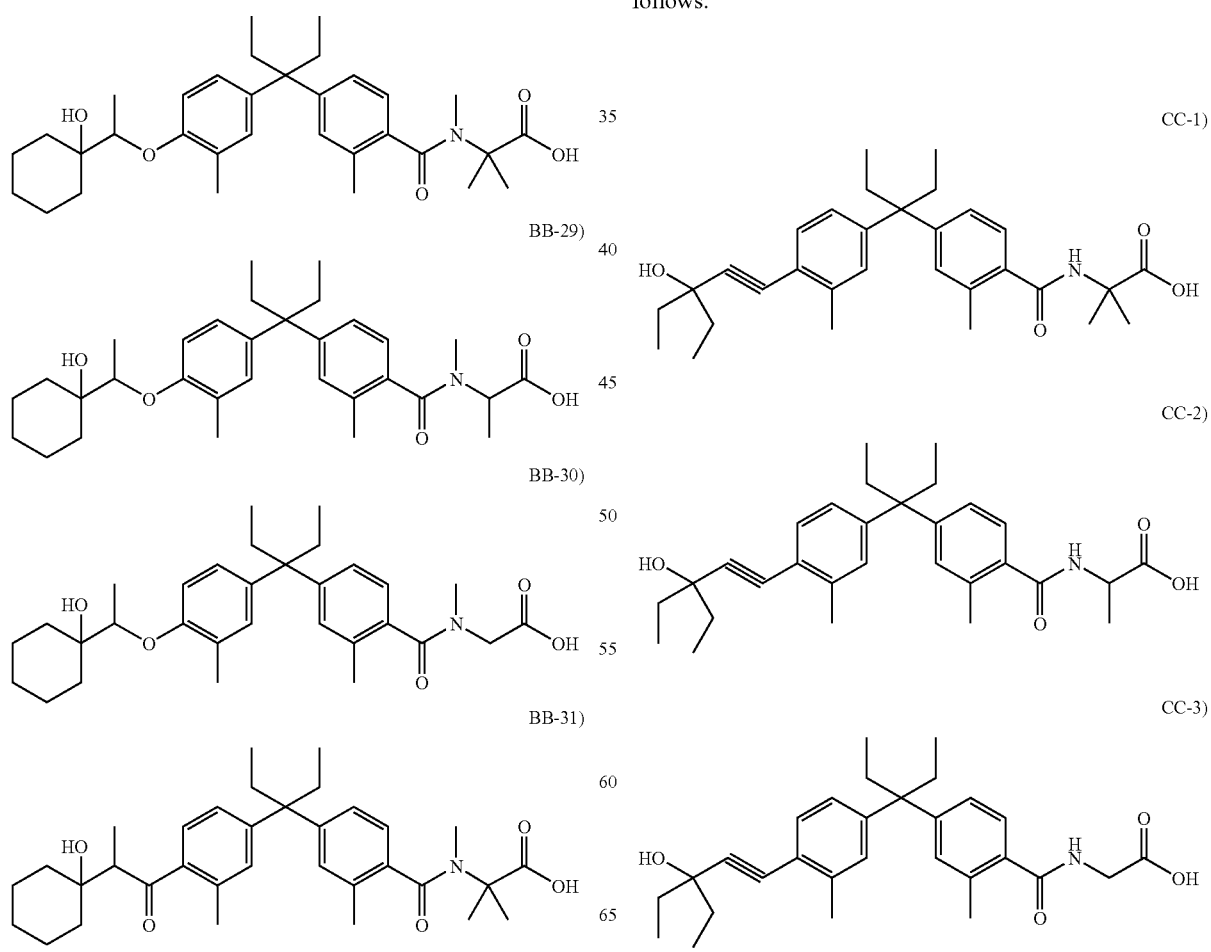

-continued
CC-4)
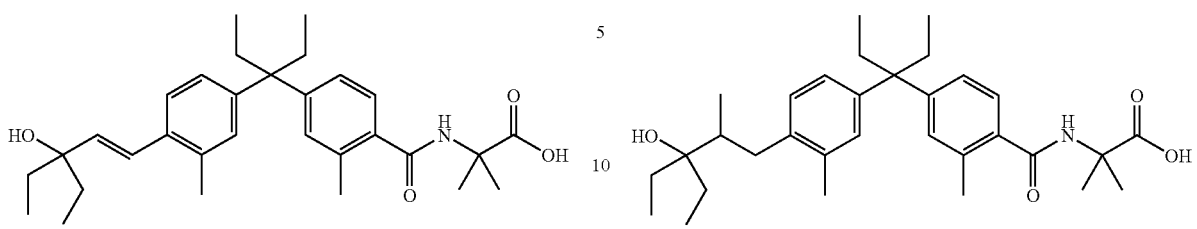
CC-5)
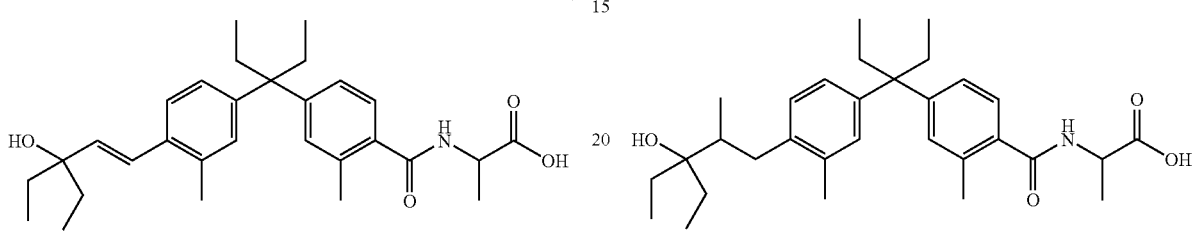
CC-6)
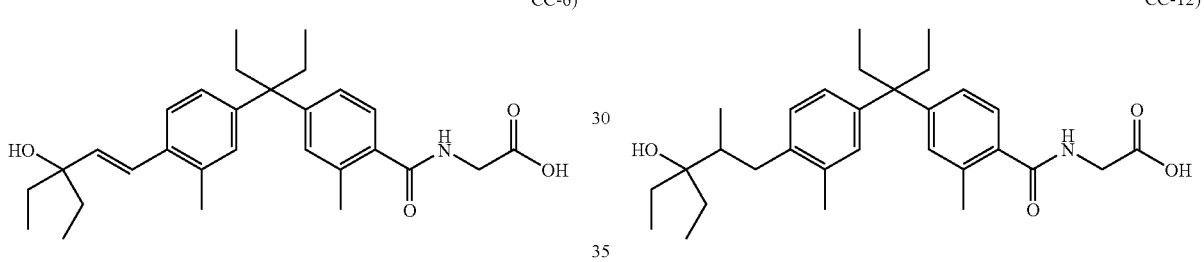
CC-7)
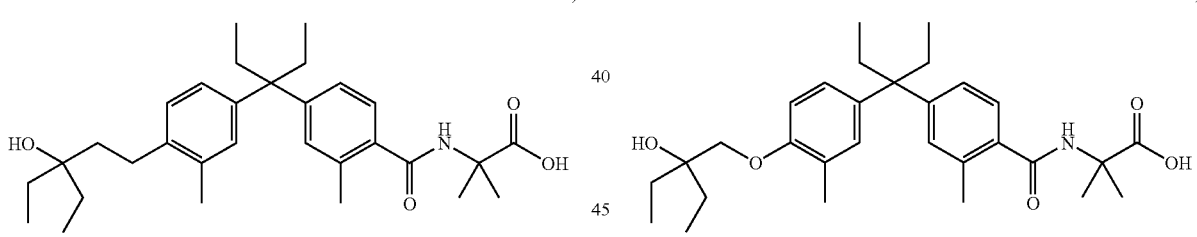
CC-8)
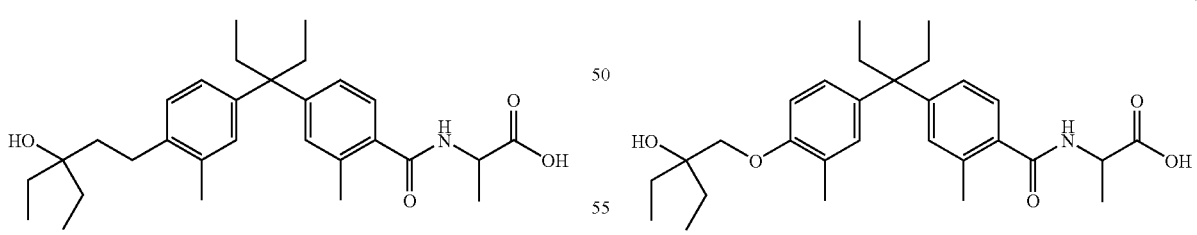
CC-9)
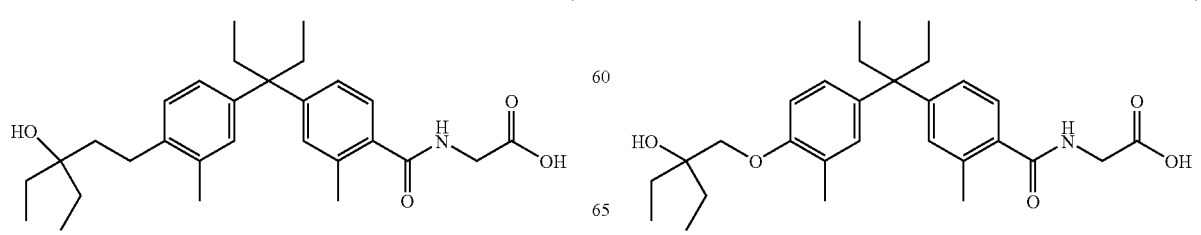
CC-10)
CC-11)
CC-12)
CC-13)
CC-14)
CC-15)

-continued
CC-16)
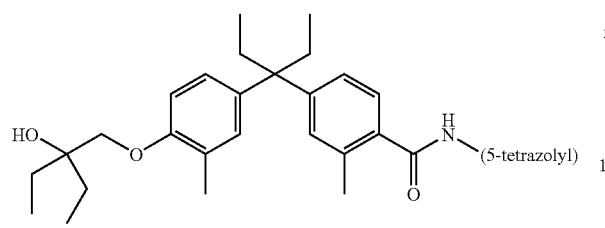
CC-22)
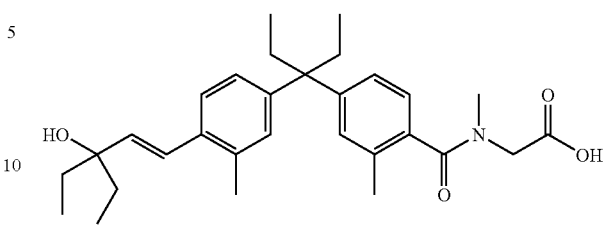
CC-17)
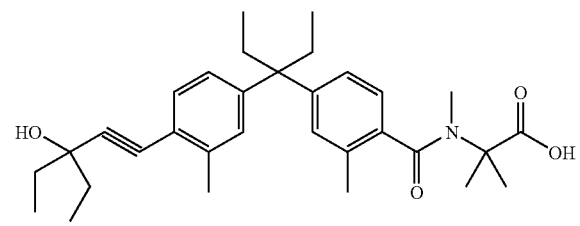
CC-23)
CC-18)
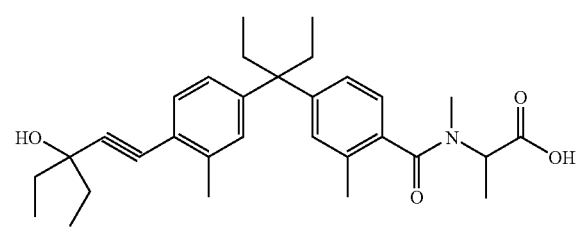
CC-24)
CC-19)
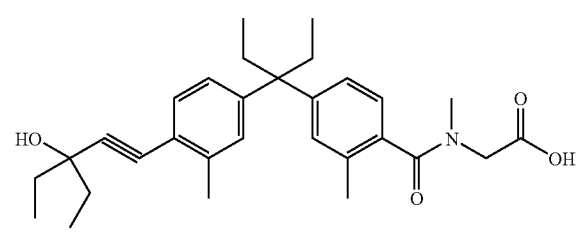
CC-25)
CC-20)
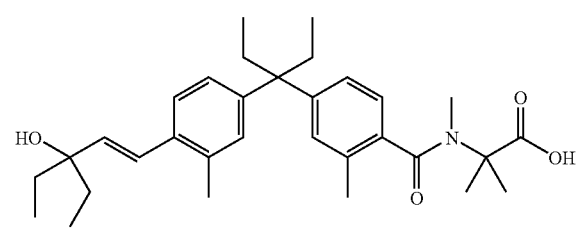
CC-26)
CC-21)
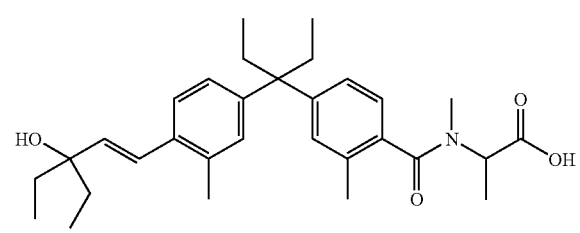
CC-27)
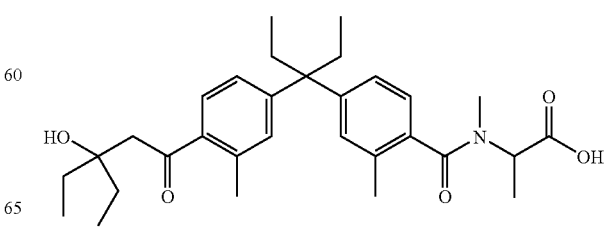

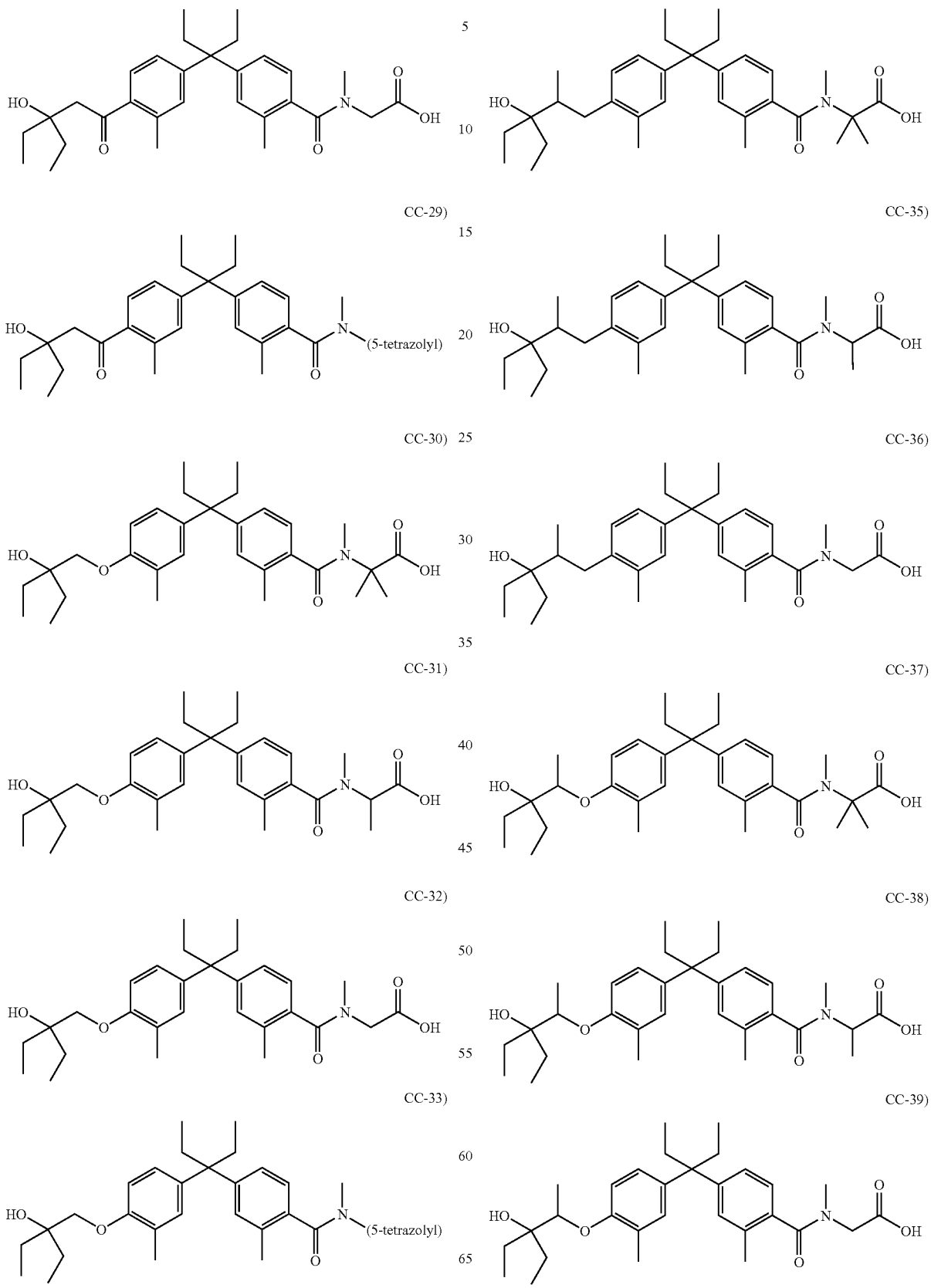

-continued
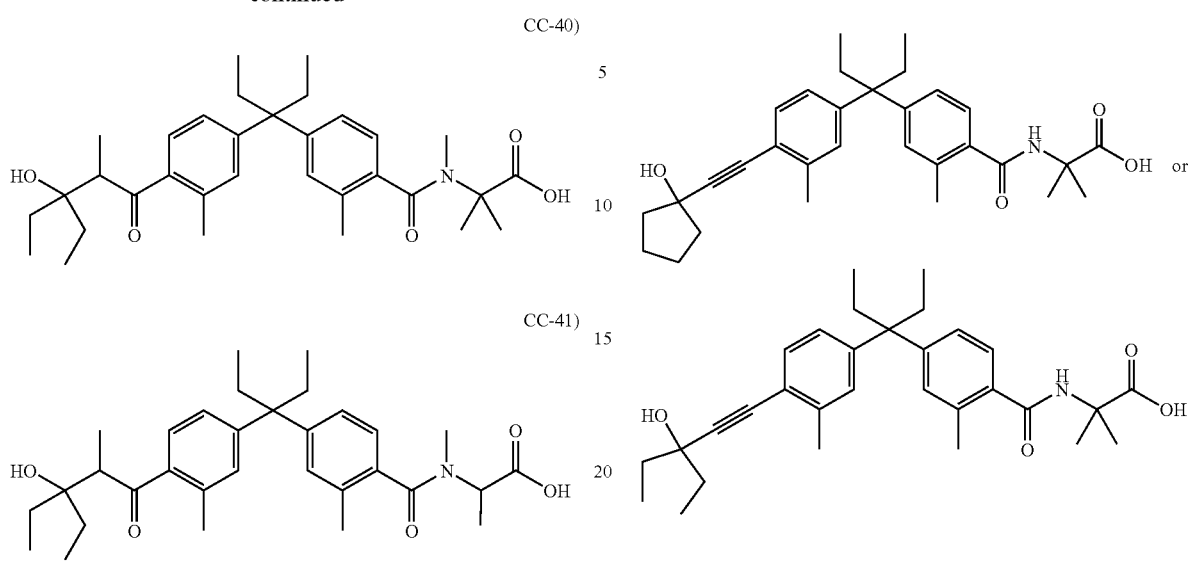
Particularly preferred compounds of the invention are
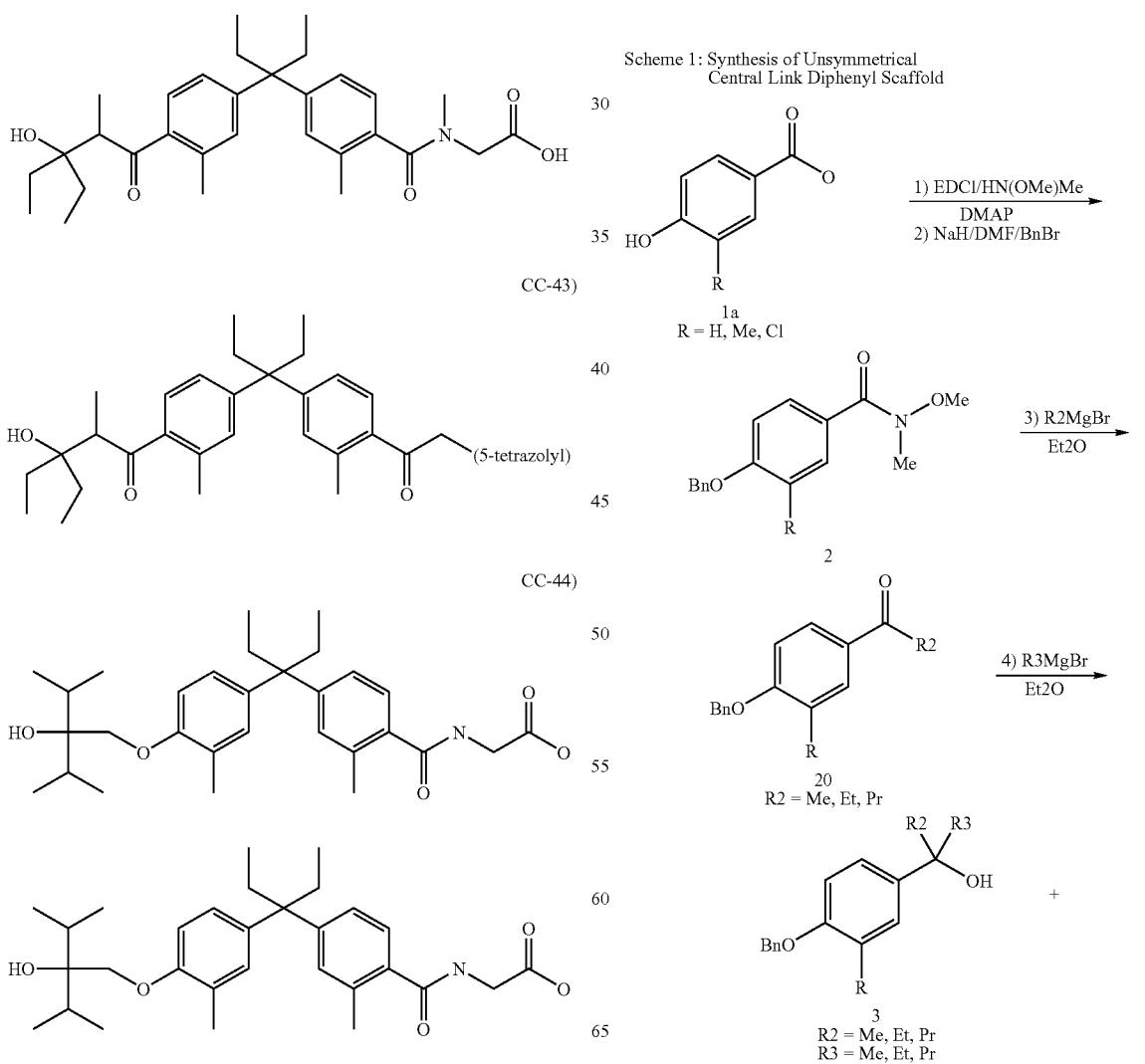
or pharmaceutically acceptable salts or prodrug derivatives thereof.

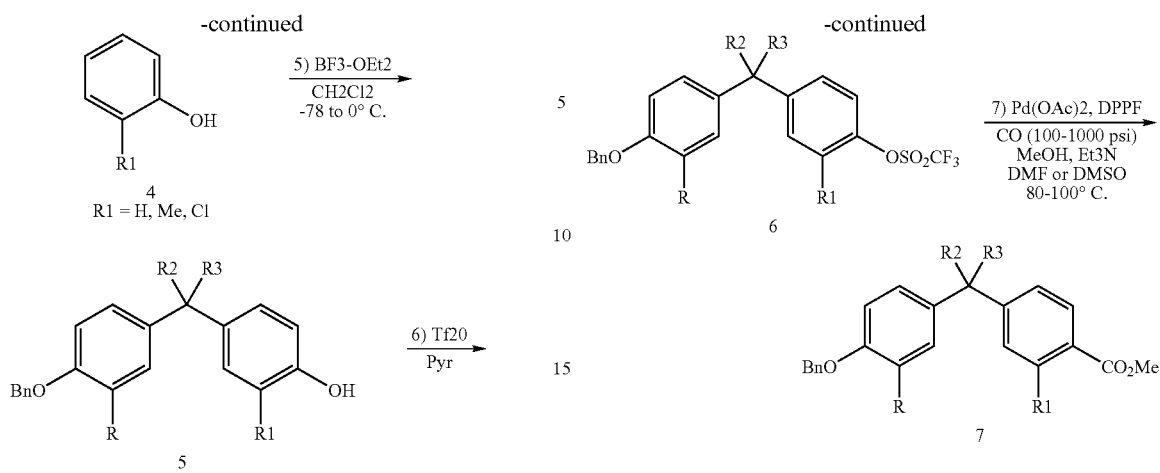
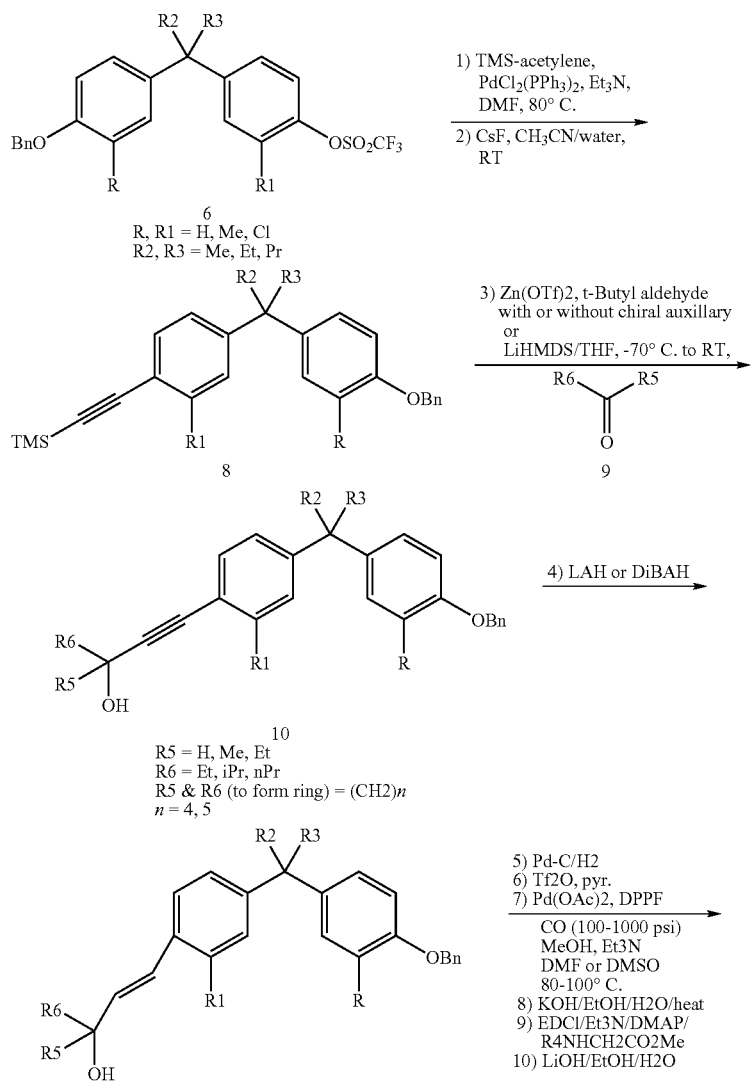
Scheme 2: Synthesis of Trans-Pentenol Phenyl Alkyl Phenyl Amide-Acids

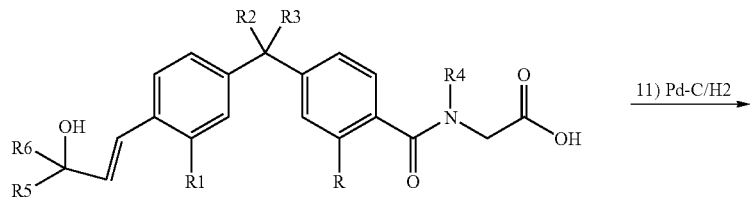
12
R, R1 = H, Me, Cl
R2, R3, = Me, Et, Pr
R4 = H, Me, Et
R5 = H, Me, Et
R6 = Et, iPr, nPr
R5 & R6 (to form ring) = (CH2)n
n = 4, 5
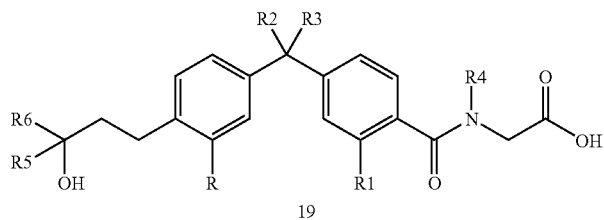
19
Scheme 3: Synthesis of Pentynol Phenyl Alkyl Phenyl Acids
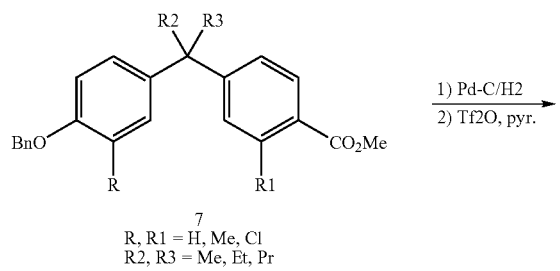
7
R, R1 = H, Me, Cl
R2, R3 = Me, Et, Pr
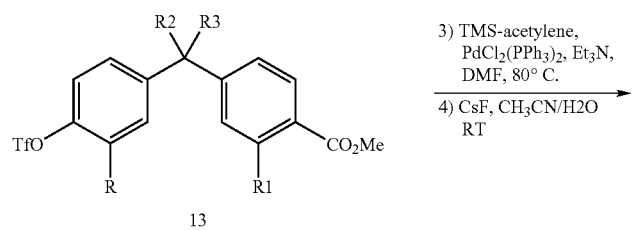
13
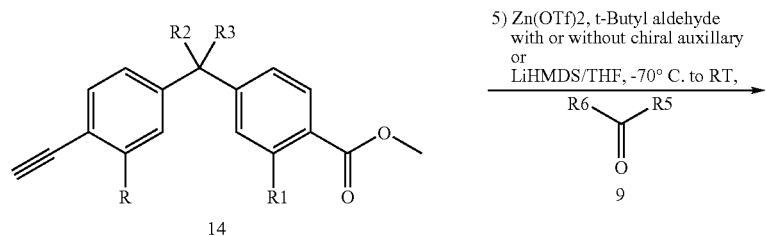
14

-continued

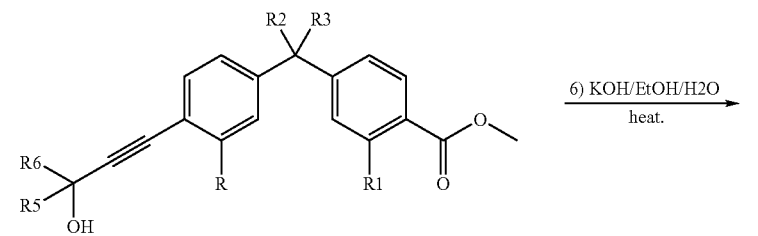

15
R5 = H, Me, Et
R6 = Et, iPr, nPr
R5 & R6 (to form ring) = (CH2)n
n = 4, 5

6) KOH/EtOH/H2O
heat.

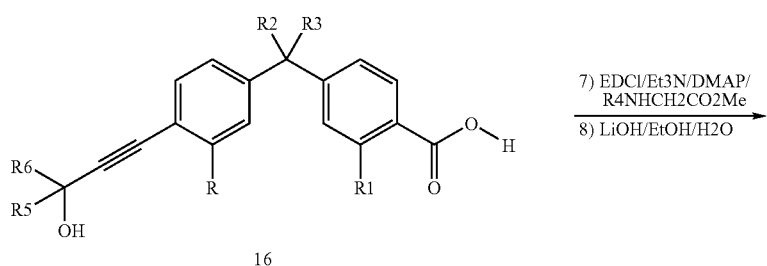

16

7) EDCl/Et3N/DMAP/
R4NHCH2CO2Me
8) LiOH/EtOH/H2O

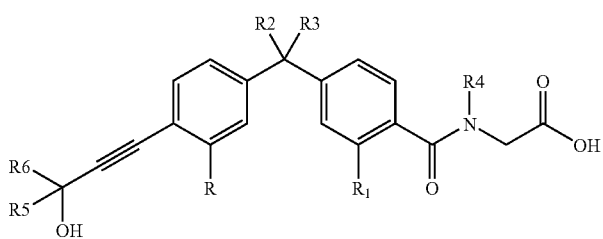

17
R, R1 = H, Me, Cl
R2, R3 = Me, Et, Pr
R4 = H, Me, Et
R5 = H, Me, Et
R6 = Et, iPr, nPr
R5 & R6 (to form ring) = (CH2)n
n = 4,5

Scheme 4: Synthesis of Cis-Pentenol
Phenyl Alkyl Phenyl Amide-Acids

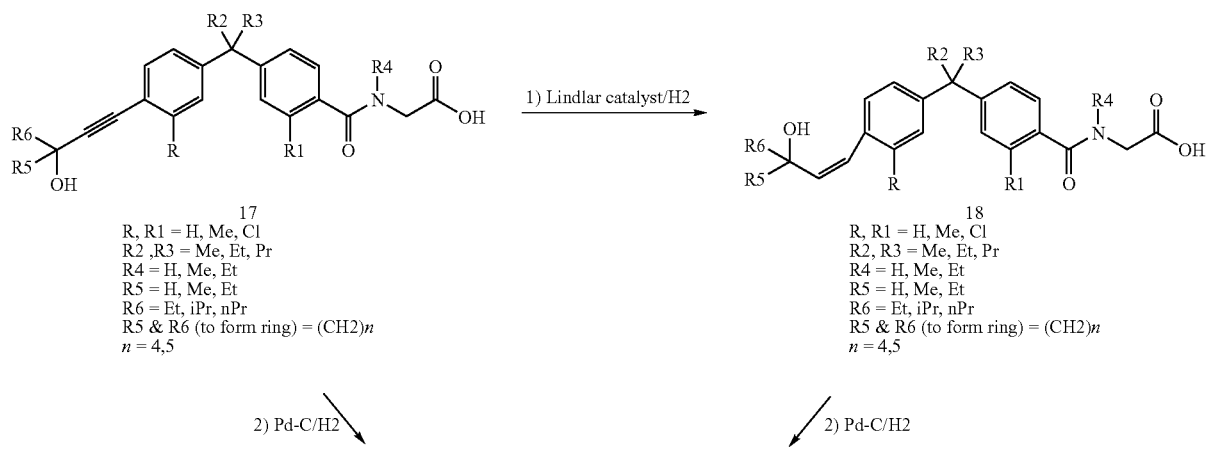

17
R, R1 = H, Me, Cl
R2, R3 = Me, Et, Pr
R4 = H, Me, Et
R5 = H, Me, Et
R6 = Et, iPr, nPr
R5 & R6 (to form ring) = (CH2)n
n = 4,5

1) Lindlar catalyst/H2

18
R, R1 = H, Me, Cl
R2, R3 = Me, Et, Pr
R4 = H, Me, Et
R5 = H, Me, Et
R6 = Et, iPr, nPr
R5 & R6 (to form ring) = (CH2)n
n = 4,5

2) Pd-C/H2

2) Pd-C/H2

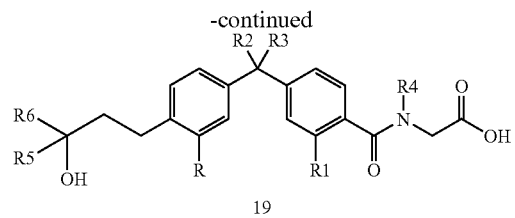

19

Preparation of Unsymmetrical Central Link Diphenyl Scaffold (Scheme 1).

A 3-Substituted-4-hydroxybenzoic acid (1a) is coupled with EDCI/N-methyl-N-methoxyamine/DMAP and alkylated with benzyl bromide to give amide 2. Amide 2 is sequentially reacted with R2MgBr and R3MgBr Grignard reagents to afford tertiary alcohol 3. Alcohol 3 is reacted with 2-substituted phenol 4 and BF3-OEt2 to produce diphenylalkane 5. Diphenylalkane 5 is reacted with triflic anhydride/pyridine to give the triflate 6, which is methoxycarbonylated with Pd(OAc)$_2$, (DPPF or DPPB), carbon monoxide, MeOH, and Et3N to give ester 7.

Synthesis of Trans-Pentenol Phenyl Alkyl Phenyl Acids (Scheme 2).

Triflate 6 is sequentially reacted with 1) TMS-acetylene, PdCl2(PPh3)2, Et3N, and DMF and 2) CsF and water to afford acetylene 8. Acetylene 8 is treated with Zn(OTf)2/t-butyl aldehyde/chiral auxiliary (with or without) to give alcohol 10. Alternatively, acetylene 8 is reacted with LiHMDS/ketone 9 to give alcohol 10. Alcohol 10 is reduced with LAH or DiBAH to afford trans-pentenol 11. Trans-pentenol 11 is sequentially reacted with 1) Pd—C/H2; 2) Tf2O/pyridine; 3) Pd(OAc)$_2$, DPPF, CO, MeOH, Et3N, DMF; 4) KOH/EtOH/H2O; 5) EDCI/Et3N/DMAP/R4NHCH2CO2Me; and 6) LiOH/EtOH/H2O to give trans-pentenol amide-acid 12. For reaction step 3, DPPB and DMSO may be substituted for DPPF and DMF, respectively. Trans-pentenol amide-acid 12 is hydrogenated with Pd—C/H2 afford amide-acid 19.

Synthesis of Pentynol Phenyl Alkyl Phenyl Acids (Scheme 3).

Ester 7 is hydrogenolyzed with Pd—C/H2 and reacted with Tf2O/pyridine to give triflate 13. Triflate 13 is sequentially reacted with 1) TMS-acetylene, PdCl2(PPh3)2, Et3N, and DMF and 2) CsF and water to afford acetylene 14. Acetylene 14 is treated with Zn(OTf)2/t-butyl aldehyde/chiral auxiliary (with or without) to give alcohol 15. Alternatively, acetylene 14 is reacted with LiHMDS/ketone 9 to give alcohol 15. Alcohol is hydrolyzed with KOH/EtOH/H2O to afford acid 16. Acid 16 is sequentially reacted with 1) EDCI/Et3N/DMAP/R4NHCH2CO2Me and 2) LiOH/EtOH/H2O to give amide-acid 17.

Synthesis of Cis-Pentenol Phenyl Alkyl Phenyl Acids (Scheme 4).

Amide-acid 17 is hydrogenated with Lindlar catalyst to afford cis-pentenol amide-acid 18. Cis-pentenol amide-acid 18 is hydrogenated with Pd—C/H2 afford amide-acid 19. Alternatively, amide-acid 17 is hydrogenated with Pd—C/H2 afford amide-acid 19.

EXAMPLES

General Experimental Conditions:

The starting material/intermediate is the compound from the immediate preceding experimental unless otherwise indicated.

All reactions are performed under nitrogen/argon atmosphere, in a stirred reaction vessel, and at room temperature unless indicated otherwise.

Unless otherwise indicated, the organic layer is MgSO$_4$/Na$_2$SO$_4$ dried is defined as stirring the solution with a desiccant for 5-15 m and filtering off the desiccant to give an anhydrous filtrate.

For analogous multi-step reaction procedures, the yield is given either for the ultimate step or overall multi-steps as indicated.

Solutions are "concentrated" at a range of 25-75° C. with reduced pressure. in-vacuo—25-75° C.; 0.05 to 1 mm Unless otherwise indicated, "the residue is chromatographed" is defined as silica gel chromatography of residue with moderate nitrogen pressure (flash chromatography) or a medium pressure chromatography systems using a silica gel to crude product ratio of ~10-100.

For HPLC, the conditions listed are for the analytical trace only. For Preparative HPLC, the eluent is similar to analytical HPLC eluent.

Thin layer chromatography is performed with silica gel plates with UV and/or appropriate staining solution.

NMR spectra are obtained with either 300 or 400 mHz spectrometer.

NMR data is listed to denote spectrum is consistent with assigned structure.

"NMR" notation without data denotes spectrum is consistent with assigned structure.

HRMS—high resolution mass spectrum
ES-MS—electrospray mass spectrum
Abbreviations:
Aq—aqueous
d—day
eq—equivalent
h—hour
m—minute
satd—saturated
disp—dispersion
quant—quantitative
rt for retention time (both small caps to minimize confusion with RT)
RT—room temperature
Chemical Definitions:
BF3-OEt2—boron trifluoride etherate
BnBr—benzyl bromide
CH2Cl2—dichloromethane
CH3CN—acetonitrile
CO—carbon monoxide
CsF—cesium fluoride DMAP—4-(dimethylamino)pyridine
DMF—N,N-dimethylformamide
DMSO—dimethylsulfoxide
DPPB—1,4-bis(diphenylphosphino)butane
DPPF—dichloro[1,1'-bis(diphenylphosphino)ferrocene
EDCI—3-Ethyl-1-[3-(dimethylamino)propyl]carbodiimide hydrochloride
Et3N—triethylamine
EtMgBr—ethyl magnesium bromide
EtOAc—ethyl acetate
EtOH—ethanol
H2—hydrogen pressure
H2NCH2CO2Me—methyl glycinate
Hept—heptane
Hex—hexanes
HN(OMe)Me—N-methyl-O-methyl hydroxylamine
HNMe2—dimethyl anine
HATU—O-(7-azabenzotriazol-1-yl)-N,N,N',N'-tetramethyluronium-hexafluorophosphate
HOAT—7-aza-1-hydroxybenzotriazole
HOBT—1-hydroxybenzotriazole
K2CO3—potassium carbonate
KI—potassium iodine
KOH—potassium hydroxide
LAH—lithium aluminum hydride
LiHMDS—lithium hexamethyldisilazide
Lindlar catalyst—Pd—$CaCO_3$—PbO
LiOH—lithium hydroxide
mCPBA—meta-chloroperbenzoic acid
MeI—methyl iodide
MeOH—methanol
NaBH4—sodium borohydride
MgSO4—magnesium sulfate
NaH—sodium hydride
NaHCO3—sodium bicarbonate
NaI—sodium iodide
Na2SO4—sodium sulfate
NH4Cl—ammonium chloride
NMO—4-methylmorpholine N-oxide
NMP—N-methylpyrrolidin-2-one
Na—S—R3—sodium alkylmercaptide
PBr3—phosphorus tribromide
Pd(DPPF)—palladium dichloro[1,1'-bis(diphenylphosphino)ferrocene
Pd(OAc)2—palladium (II) acetate
Pd(TPP)4—palladium tetrakistriphenylphosphine
Pd—C—palladium on carbon
Pd—C/H2—palladium on carbon with hydrogen pressure
pTSA—para-toluenesulfonic acid
Pyr—pyridine
Red-Al—sodium bis(2-methoxyethoxy)aluminum hydride
R2MgBr—alkyl magnesium bromide
R3MgBr—alkyl magnesium bromide
R5MgBr—alkyl magnesium bromide
R3S(O)2Cl—alkylsulfonyl chloride
R2S(O)2NH2—alkylsulfonamide
TBSCl—tert-butyldimethylsilyl chloride
tBuC(O)CH2Br—1-bromopinacolone
Tf2O—triflic anhydride
TFA—trifluoroacetic acid
THF—tetrahydrofuran
Ti(OiPr)4—titanium tetraisopropoxide
TMS-acetylene—trimethylsilyl acetylene
TPAP—tetrapropylammonium perruthenate
Zn(OTf)2—zinc trifluoromethane sulfonate Example 1

Preparation of 2-(4-{1-Ethyl-1-[4-(1-hydroxy-cyclopentylethynyl)-3-methyl-phenyl]-propyl}-2-methyl-benzoylamino)-2-methyl-propionic acid

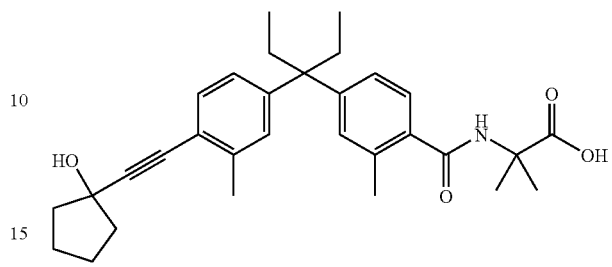

A. [E,Z]-3-(3-Methyl-4-hydroxyphenyl)-3-pentene

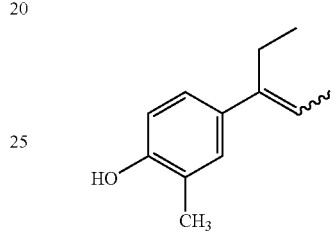

A mixture of 3-(3-methyl-4-hydroxyphenyl)-3-pentanol (20.0 g, 102.9 mmol), pTSA monohydrate (50 mg, 0.26 mmol catalytic amount), cyclohexane (150 mL), and toluene (250 mL) is refluxed on a steam bath for 3 h. During the reflux time, water is separated by means of a Dean-Stark trap. Analysis of the reaction mixture by TLC (SiO2; CHCl3) shows a spot to spot transformation of the starting material into a less polar material. The cyclohexane-toluene solution is cooled to RT, washed with satd sodium carbonate solution (25 mL), MgSO4 dried, and concentrated to give the title compounds as a [E:Z] isomeric mixture of [4:1] (17.36 g, 96%).

H-NMR (300 mHz, DMSO-d6): δ 6.85-7.10 (3H, m), 5.56 (0.8H, q, J=6.8 Hz), 5.39, 0.2H, q, J=6.8 Hz), 2.40 ((1.6H, q, J=7.6 Hz), 2.25 (0.4H, q, J=7.6 Hz), 2.15 (0.6H, s), 2.05 (2.4H, s), 1.70 (2.4H, d, J=7.6 Hz), 1.51 (0.6H, d, J=7.6 Hz), 0.90 (2.4H, t, J=7.6 Hz)), 0.85 (0.4H, t, J=7.6 Hz).

ES GC MS m/z 176.1, [M+]; Calc. C12H16O m/z 176.1.

B. [E,Z]-3-[3-Methyl-4-(trifluoromethylsulfonyloxy)phenyl]-3-pentene

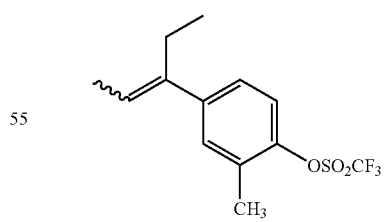

A solution of [E,Z]-3-(3-methyl-4-hydroxyphenyl)-3-pentene (17.0 g, 96.4 mmol) and triethylamine (10.3 g, 101 mmol) in $CH_2Cl_2$ (400 mL) under a N2 atmosphere is cooled to −35° C. in a dry ice bath. Triflic anhydride (28.6 g, 101 mmol) is added slowly by syringe so as to maintain the temperature below −30° C. The resulting pale yellow solution is stirred for 3 h as it is allowed to warm to RT. The reaction mixture is poured over 300 ml pH 7.0 buffer and 300 ml ice. The organic layer is separated and the CH2Cl2 layer is washed with additional (4×150 mL) buffer and dried over anhydrous MgSO4. Removal of the solvent under reduced pressure gives the crude product as a yellow oil (approx 30 g). The product is purified by chromatography over silica using elution with 5% CHCl3 in hexane. The desired product is obtained as a clear, colorless liquid as a mixture of [E:Z] isomers ratio of 4:1, respectively (29.4 g, 99%).

H-NMR (300 mHz, DMSO-d6): δ 7.01-7.28 (3H, m), 5.76 (0.8H, q, J=6.8 Hz), 5.57, 0.2H, q, J=6.8 Hz), 2.52 ((1.6H, q, J=7.6 Hz), 2.25 (0.4H, q, J=7.6 Hz), 2.40 (0.6H, s), 2.39 (2.4H, s), 1.81 (2.4H, d, J=7.6 Hz), 1.55 (0.6H, d, J=7.6 Hz), 0.99 (2.4H, t, J=7.6 Hz)), 0.97 (0.4H, t, J=7.6 Hz).

ES GC MS m/z 308.1, [M+]; Calc. for C13H15F3O3S m/z 308.1.

C. [E,Z]-3-(3-Methyl-4-carbomethoxyphenyl)-3-pentene

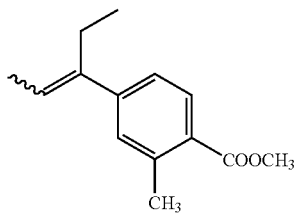

A mixture of [E,Z]-3-[3-methyl-4-(trifluoromethylsulfonyloxy)phenyl)-3-pentene (25.0 g, 81 mmol), MeOH, dppb, DMSO, Et3N, and Pd(OAc)2 is carbonylated by reaction at 80° C. under an atmosphere of CO (100 psi). for a total of 6 h. The cooled reaction mixture is filtered through filter-cell with the aid of additional MeOH. The filtrate is concentrated under reduced pressure to remove most of the DMSO and the residue is distributed between EtOAc and brine. The organic layer is washed 5 times with brine, dried over MgSO4, and concentrated to an oil. The oil is purified by chromatography over silica gel using a 10% to 50% chloroform in hexane gradient. Concentration of appropriate fractions provides the desired product as a clear, nearly colorless liquid as a mixture of [E:Z] isomers ratio of 4:1, respectively (15.2 g, 86%).

TLC (CHCl3): Rf ~0.7

H-NMR (300 mHz, CDCl$_3$): δ 7.03-7.93 (3H, m), 5.83 (0.75H, q, J=6.9 Hz), 5.57 (0.25H, q, J=6.9 Hz), 3.91 (0.6H, s), 3.90 (2.4H, s), 2.54 ((1.5H, q, J=7.6 Hz), 2.35 (0.5H, q, J=7.6 Hz), 1.83 (2.25H, d, J=7.6 Hz), 1.57 (0.75H, d, J=7.6 Hz), 1.00 (2.25H, t, J=7.6 Hz)), 0.97 (0.75H, t, J=7.6 Hz).

D. 3'-[3-Methyl-4-(hydroxy)phenyl]-3'-(3-methyl-4-carbomethoxy-phenyl)pentane

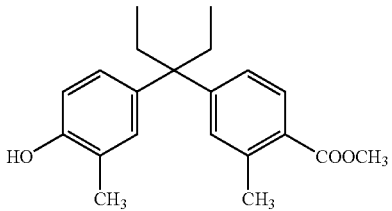

A 25° C. solution of [E,Z]-3-[3-methyl-4-(carbomethoxy) phenyl)-3-pentene (5.00 g, 22.9 mmol) in o-cresol (9.90 g, 91.6 mmol) is treated with BF3-etherate (5.6 g, 39.5 mmol) and the reaction mixture is stirred for 16 h at ambient temperature. Analysis by TLC (SiO2; CHCl3) shows loss of the starting material and formation of a major product spot at slightly lower Rf than o-cresol. The reaction mixture is taken up in 200 mL ice water and 200 mL ether and carefully basified with excess solid NaHCO3. The ether layer is separated, washed with brine, dried over anhydrous MgSO4 and concentrated to an oil. The oil is vacuum distilled with 3×15 mL ethylene glycol to remove the remaining o-cresol and the resulting pot residue is cooled and redistributed-into ether and water and treated with NaHCO3, as above. The ether layer is separated, washed with water, dried over MgSO4 and concentrated to provide the crude product as a yellow oil (7.3 g). The oil is purified by chromatography over silica gel using CHCl3 to provide the title compound as a pale yellow oil (5.42 g, 72%).

H-NMR (300 mHz, CDCl3): 6.66 to 7.83 (6H, m) 4.54 (1H, s), 3.89 (3H, s), 2.61 (3H, s), 2.21 (3H, s), 2.08 (4H, q, J=7.3 Hz), 0.62 (6H, t, J=7.3 Hz).

ES (−) MS m/z 325.2 [M−H]

IR (CHCl3): 1716 cm$^{-1}$.

E. 4-[1-Ethyl-1-(3-methyl-4-trifluoromethanesulfonyloxy-phenyl)-propyl]-2-methyl-benzoic acid methyl ester

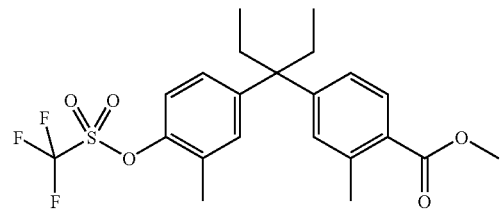

4-[1-Ethyl-1-(4-hydroxy-3-methyl-phenyl)-propyl]-2-methyl-benzoic acid methyl ester (10.0 g, 30.63 mmol) in pyridine (30 ml) is added dropwise trifluoromethane sulfonic anhydride (10.37 g, 36.76 mmol) and warmed to room temperature overnight. The reaction is quenched by pouring into ice/water mix (200 ml) and extracted with Et$_2$O (3×200 ml). The combined organic layers are washed with water (100 ml), 1N HCl (100 ml), water (100 ml), brine (100 ml), dried (MgSO$_4$), concentrated and chromatographed (330 g SiO$_2$, 5% EtOAc/Hexanes) to yield the title compound (12.46 g, 90%) as a pale yellow oil.

[1]NMR (400 MHz, CDCl$_3$) δ ppm: 7.85 (d, 1H, J=8.4 Hz), 7.15 (d, 1H, J=8.4 Hz), 7.10-7.02 (m, 4H), 7.10-7.02 (m, 4H), 3.91 (s, 3H), 2.60 (s, 3H), 2.35 (s, 3H), 2.13 (q, 4H, J=7.3 Hz), 0.64 (t, 6H, J=7.3 Hz).

F. 4-[1-Ethyl-1-(3-methyl-4-trimethylsilanylethynyl-phenyl)-propyl]-2-methyl-benzoic acid methyl ester

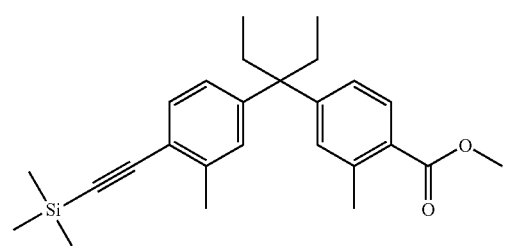

4-[1-Ethyl-1-(3-methyl-4-trifluoromethanesulfonyloxy-phenyl)-propyl]-2-methyl-benzoic acid methyl ester (11.20 g, 24.43 mmol) in DMF (100 ml) is added trimethylsilylacetylene (6.90 ml, 48.85 mmol), dichlorobis(triphenylphosphine) palladium (1.71 g, 2.44 mmol) and triethylamine (23.84 ml, 171 mmol) and heated to 80° C. overnight. The reaction mixture is concentrated and filtered through a pad of silica gel eluted with 10% EtOAc/Hexanes. The eluent is concentrated and chromatographed (330 g SiO$_2$, 2% EtOAc/Hexanes) to yield the title compound (8.07 g, 81%) as an orange oil.

$^1$NMR (400 MHz, CDCl$_3$) δ ppm: 7.82 (d, 1H, J=7.9 Hz), 7.35 (d, 1H, J=8.4 Hz), 7.08-6.97 (m, 3H), 6.94 (d, 1H, J=8.4 Hz), 3.90 (s, 3H), 2.57 (s, 3H), 2.41 (s, 3H), 2.11 (q, 5H, J=7.7 Hz), 0.62 (t, 6H, J=7.3 Hz), 0.28 (s, 9H).

G. 4-[1-Ethyl-1-(4-ethynyl-3-methyl-phenyl)-propyl]-2-methyl-benzoic acid methyl ester

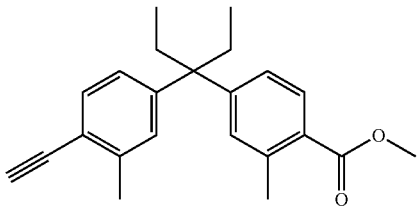

To an ambient temperature suspension of 4-[1-Ethyl-1-(3-methyl-4-trimethylsilanylethynyl-phenyl)-propyl]-2-methyl-benzoic acid methyl ester (6.8 g, 16.72 mmol) in acetonitrile/water (180/30 ml) is added cesium fluoride (25.4 g, 167.2 mmol) and stirred for 3d. The reaction mixture is concentrated and partitioned between EtOAc (500 ml) and 1N HCl (200 ml). The aqueous phase is extracted with a second portion of EtOAc (200 ml) and the combined organic phases are washed with brine (200 ml), dried (MgSO$_4$), concentrated and chromatographed (330 g SiO$_2$, 1% EtOAc/Hexanes) to yield the title compound (5.52 g, 99%).

$^1$NMR (400 MHz, CDCl$_3$) δ ppm: 7.80 (d, 1H, J=8.4 Hz), 7.34 (d, 1H, J=8.4 Hz), 7.04-6.99 (m, 2H), 6.97 (s, 1H), 6.92 (d, 1H, J=7.9 Hz), 3.86 (s, 3H), 3.23 (s, 1H), 2.55 (s, 3H), 2.39 (s, 3H), 2.09 (q, 4H, J=7.2 Hz), 0.60 (t, 6H, J=7.3 Hz).

H. 4-{1-Ethyl-1-[4-(1-hydroxy-cyclopentylethynyl)-3-methyl-phenyl]-propyl}-2-methyl-benzoic acid methyl ester

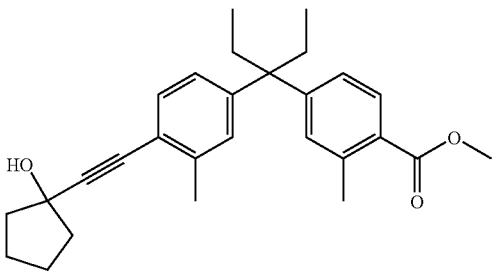

To a −78 C solution of 4-[1-Ethyl-1-(4-ethynyl-3-methyl-phenyl)-propyl]-2-methyl-benzoic acid methyl ester (2.50 g, 7.47 mmol) in THF (80 ml) is added lithium hexamethyldisilazide (8.22 ml, 8.22 mmol, 1.0 M in THF) and stirred at −78 C for 30 min. Cyclopentanone (730 µL, 8.22 mmol) is added and the reaction mixture warmed to room temperature. The reaction is quenched with saturated aqueous NH$_4$Cl (30 ml) and concentrated. The residue is partitioned between EtOAc (300 ml) and 1.0N HCl (50 ml). The aqueous layer is extracted with EtOAc (100 ml). The combined organic layer are washed with water (50 ml), brine (50 ml), dried (MgSO$_4$), concentrated and chromatographed (120 g SiO$_2$, 5% EtOAc/Hexanes) to yield the title compound (2.45 g, 79%).

$^1$NMR (400 MHz, CDCl$_3$) δ ppm: 7.83 (d, 1H, J=8.8 Hz), 7.32 (dd, 1H, J=7.9, 2.2 Hz), 7.08-6.98 (m, 3H), 6.95 (d, 1H, J=8.4 Hz), 3.91 (s, 3H), 2.58 (s, 3H), 2.41 (s, 3H), 2.12 (q, 4H, J=7.2 Hz), 1.87-1.74 (m, 4H), 1.15 (t, 6H, J=7.4 Hz), 0.64 (t, 6H, J=7.3 Hz).

I. 4-{1-Ethyl-1-[4-(1-hydroxy-cyclopentylethynyl)-3-methyl-phenyl]-propyl}-2-methyl-benzoic acid

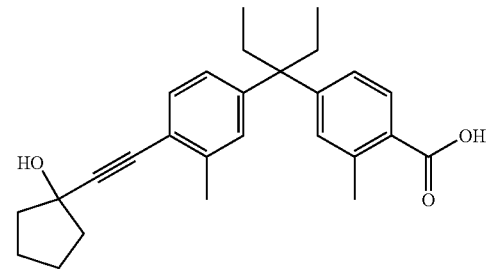

To an ambient temperature solution of 4-{1-Ethyl-1-[4-(1-hydroxy-cyclopentylethynyl)-3-methyl-phenyl]-propyl}-2-methyl-benzoic acid methyl ester (2.40 g, 5.73 mmol) in dioxane/water (30/30 ml) is added lithium hydroxide (412 mg, 17.20 mmol) and heated to 60° C. for 1 h. The reaction is concentrated and partitioned between Et$_2$O/EtOAc (150/150 ml) and 1N HCl (50 ml). The aqueous phase is extracted with a second portion of EtOAc (100 ml) and the combined organic phases are washed with water (50 ml), brine (50 ml), dried (MgSO$_4$) and concentrated to yield the title compound (1.57 g, 68%).

$^1$NMR (400 MHz, CDCl$_3$) δ ppm: 7.93 (d, 1H, J=8.4 Hz), 7.28 (d, 1H, J=8.4 Hz), 7.05 (d, 1H, J=8.4 Hz), 7.03 (s, 1H), 6.96 (s, 1H), 6.92 (dd, 1H, J=8.1, 2.0 Hz), 2.58 (s, 3H), 2.36 (s, 3H), 2.15-1.97 (m, 8H), 1.94-1.72 (m, 4H), 0.60 (t, 6H, J=7.3 Hz).

High Res. EI-MS: 403.2270; calc. for C$_{27}$H$_{32}$O$_3$—H, 403.2273.

J. 2-(4-{1-Ethyl-1-[4-(1-hydroxy-cyclopentylethynyl)-3-methyl-phenyl]-propyl}-2-methyl-benzoylamino)-2-methyl-propionic acid methyl ester

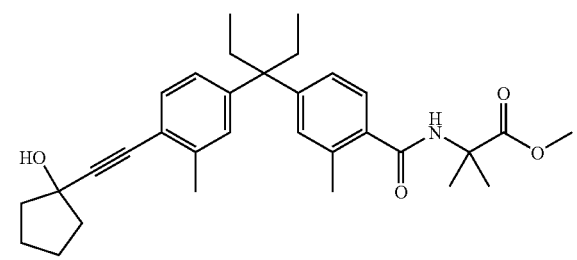

4-{1-Ethyl-1-[4-(1-hydroxy-cyclopentylethynyl)-3-methyl-phenyl]-propyl}-2-methyl-benzoic acid (389 mg, 0.962 mmol), α-aminoisobutyric acid methyl ester hydrochloride (221 mg, 1.44 mmol), 1-(3-dimethyl-aminopropyl)-3-ethylcarbodiimide hydrochloride (276 mg, 1.44 mmol), 1-hydroxybenzotriazole hydrate (195 mg, 1.44 mmol) and triethylamine (536 µL, 3.85 mmol) are stirred overnight. The reaction is concentrated and partitioned between EtOAc (150 ml) and 1N HCl (50 ml). The aqueous layer is extracted with EtOAc (100 ml). The combined organic layers are washed with, water (50 ml), NaHCO$_3$ (50 ml), brine (50 ml), dried (anhydrous MgSO$_4$), concentrated and chromatographed (12 g SiO$_2$, 15% EtOAc/Hexanes) to yield the title compound (398 mg, 82%).

$^1$NMR (400 MHz, CDCl$_3$) δ ppm: 7.29-7.24 (m, 2H), 6.99-6.88 (m, 4H), 6.27 (s, 1H), 3.77 (s, 3H), 2.39 (s, 3H), 2.36 (s, 3H), 2.12-1.98 (m, 8H), 1.93-1.73 (m, 4H), 1.65 (s, 6H), 0.59 (t, 6H, J=7.3 Hz).

High Res. EI-MS: 504.3133; calc. for C$_{32}$H$_{41}$NO$_4$+H, 504.3114.

K. 2-(4-{1-Ethyl-1-[4-(1-hydroxy-cyclopentylethynyl)-3-methyl-phenyl]-propyl}-2-methyl-benzoylamino)-2-methyl-propionic acid

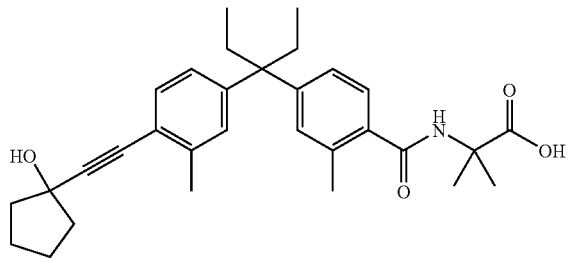

2-(4-{1-Ethyl-1-[4-(1-hydroxy-cyclopentylethynyl)-3-methyl-phenyl]-propyl}-2-methyl-benzoylamino)-2-methyl-propionic acid methyl ester (360 mg, 0.715 mmol) and lithium hydroxide (51 mg, 2.15 mmol) are reacted and purified in a procedure analogous to Example 1I to give the title compound (353 mg, quant.).

$^1$NMR (400 MHz, CDCl$_3$) δ ppm: 7.27 (d, 2H, J=8.4 Hz), 7.01-6.87 (m, 4H), 6.22 (s, 1H), 2.40 (s, 3H), 2.36 (s, 3H), 2.12-1.98 (m, 8H), 1.93-1.73 (m, 4H), 1.68 (s, 6H), 0.59 (t, 6H, J=7.0 Hz).

High Res. EI-MS: 490.2957; calc. for C$_{31}$H$_{39}$NO$_4$+H, 490.2975.

Example 2

Preparation of 2-(4-{1-Ethyl-1-[4-(3-ethyl-3-hydroxy-pent-1-ynyl)-3-methyl-phenyl]-propyl}-2-methyl-benzoylamino)-2-methyl-propionic acid

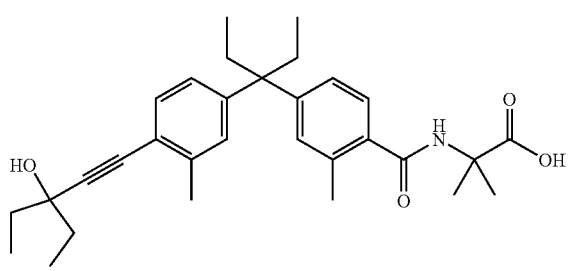

A. 4-{1-Ethyl-1-[4-(3-ethyl-3-hydroxy-pent-1-ynyl)-3-methyl-phenyl]-propyl}-2-methyl-benzoic acid methyl ester

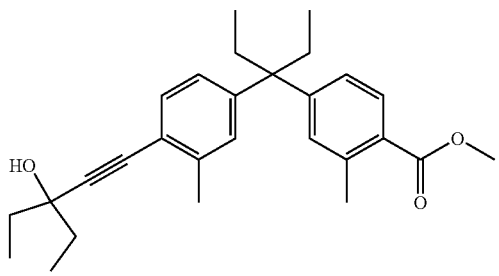

4-[1-Ethyl-1-(4-ethynyl-3-methyl-phenyl)-propyl]-2-methyl-benzoic acid methyl ester (2.50 g, 7.47 mmol), lithium hexamethyldisilazide (8.22 ml, 8.22 mmol, 1.0 M in THF) and 3-pentanone (870 µL, 8.22 mmol) are reacted and purified analogous to Example 1H to give the title compound (2.22 g, 71%).

$^1$NMR (400 MHz, CDCl$_3$) δ ppm: 7.79 (d, 1H, J=7.9 Hz), 7.27 (d, 1H, J=8.6 Hz), 7.04-6.98 (m, 2H), 6.95 (s, 1H), 6.91 (dd, 1H, J=8.0, 1.9 Hz), 3.86 (s, 3H), 2.54 (s, 3H), 2.36 (s, 3H), 2.13-1.98 (m, 8H), 1.94-1.72 (m, 5H), 0.59 (t, 6H, J=7.3 Hz).

B. 4-{1-Ethyl-1-[4-(3-ethyl-3-hydroxy-pent-1-ynyl)-3-methyl-phenyl]-propyl}-2-methyl-benzoic acid

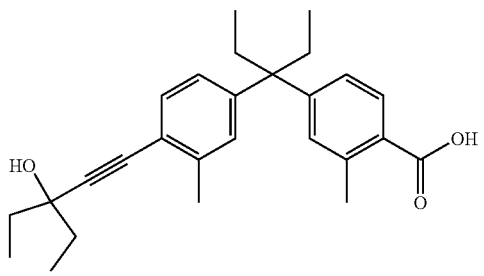

4-{1-Ethyl-1-[4-(3-ethyl-3-hydroxy-pent-1-ynyl)-3-methyl-phenyl]-propyl}-2-methyl-benzoic acid methyl ester (2.20 g, 5.23 mmol) and lithium hydroxide (376 mg, 15.69 mmol) are reacted and purified analogous to Example 1I to give the title compound (1.77 g, 83%).

$^1$NMR (400 MHz, CDCl$_3$) δ ppm: 7.93 (d, 1H, J=7.9 Hz), 7.29 (d, 1H, J=8.4 Hz), 7.08-7.01 (m, 2H), 6.97 (s, 1H), 6.92 (d, 1H, J=7.5 Hz), 2.59 (s, 3H), 2.38 (s, 3H), 2.10 (q, 4H, J=7.3 Hz), 1.84-1.69 (m, 4H), 1.11 (t, 6H, J=7.2 Hz), 0.61 (t, 6H, J=7.3 Hz).

High Res. EI-MS: 405.2444; calc. for C$_{27}$H$_{34}$O$_3$—H, 405.2430.

C. 2-(4-{1-Ethyl-1-[4-(3-ethyl-3-hydroxy-pent-1-ynyl)-3-methyl-phenyl]-propyl}-2-methyl-benzoylamino)-2-methyl-propionic acid methyl ester

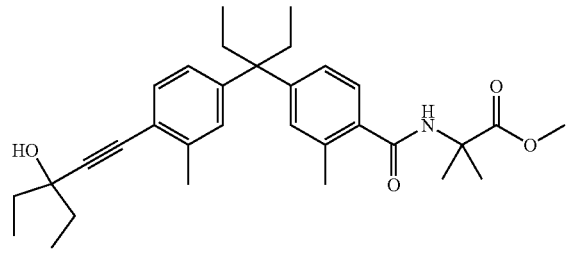

4-{1-Ethyl-1-[4-(3-ethyl-3-hydroxy-pent-1-ynyl)-3-methyl-phenyl]-propyl}-2-methyl-benzoic acid (437 mg, 1.07 mmol), α-aminoisobutyric acid methyl ester hydrochloride (247 mg, 1.61 mmol), 1-(3-dimethyl-aminopropyl)-3-ethyl-carbodiimide hydrochloride (309 mg, 1.61 mmol), 1-hydroxybenzotriazole hydrate (218 mg, 1.61 mmol) and triethylamine (597 µL, 4.28 mmol) are reacted and purified analogous to Example 1J to give the title compound (419 mg, 77%).

$^1$NMR (400 MHz, CDCl$_3$) δ ppm: 7.29-7.25 (m, 2H), 7.00-6.89 (m, 4H), 6.27 (s, 1H), 3.77 (s, 3H), 2.39 (s, 3H), 2.37 (s, 3H), 2.06 (q, 4H, J=7.3 Hz), 1.83-1.70 (m, 4H), 1.65 (s, 6H), 1.11 (t, 6H, J=7.5 Hz), 0.59 (t, 6H, J=7.3 Hz).

High Res. EI-MS: 506.3271; calc. for C$_{32}$H$_{43}$NO$_4$+H, 506.3270.

D. 2-(4-{1-Ethyl-1-[4-(3-ethyl-3-hydroxy-pent-1-ynyl)-3-methyl-phenyl]-propyl}-2-methyl-benzoylamino)-2-methyl-propionic acid

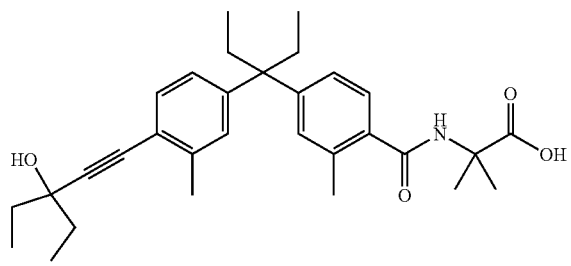

2-(4-{1-Ethyl-1-[4-(3-ethyl-3-hydroxy-pent-1-ynyl)-3-methyl-phenyl]-propyl}-2-methyl-benzoylamino)-2-methyl-propionic acid methyl ester (3.97 mg, 0.785 mmol) and lithium hydroxide (56 mg, 2.36 mmol) are reacted and purified analogous to Example 1I to give the title compound (384 mg, 99%).

$^1$NMR (400 MHz, CDCl$_3$) δ ppm: 7.30-7.26 (m, 2H), 7.02-6.97 (m, 2H), 6.95 (s, 1H), 6.91 (d, 1H, J=8.4 Hz), 6.21 (s, 1H), 2.40 (s, 3H), 2.37 (s, 3H), 2.07 (q, 4H, J=6.6 Hz), 1.83-1.71 (m, 4H), 1.68 (s, 6H), 1.11 (t, 6H, J=7.3 Hz), 0.59 (t, 6H, J=7.3 Hz).

High Res. EI-MS: 492.3116; calc. for C$_{31}$H$_{41}$NO$_4$+H, 492.3114.

Example 3

Preparation of (4-{1-ethyl-1-[4-(2-ethyl-2-hydroxy-butoxy)-3-methyl-phenyl]-propyl}-2-methyl-benzoylamino)-acetic acid

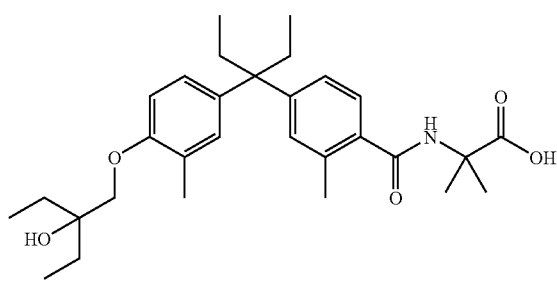

A. 3',3'-Bis[4-hydroxy-3-methylphenyl]pentane

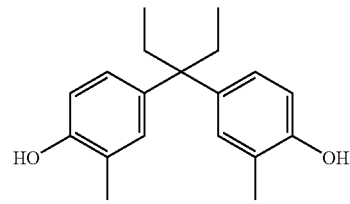

To a mixture of o-cresol (196 g, 1.81 mol) and 3-pentanone (60 ml, 0.57 mol) is added methanesulfonic acid (45 ml, 0.69 mol) and stirred for 3 days. The reaction is basified to pH 8 with satd Na$_2$CO$_3$ and extracted with EtOAc. The organic layer is washed with water (6×500 ml), Na$_2$SO$_4$ dried, concentrated, chromatographed (2 kg SiO2, Hex to 80% EtOAc/Hex), and triturated with Hex to give the title compound as a white solid (100 g, 61%).

NMR 400 mHz(DMSO): δ 0.49 (t, J=7.3 Hz, 6H), 1.91 (q, J=7.3 Hz, 4H), 2.02 (s, 6H), 6.61 (d, J=8.3 Hz, 2H), 6.73 (d, J=8.3 Hz, 2H), 6.76 (s, 2H), 8.94 (s, 2H).

High Res. EI-MS: 284.1794; calc. for C$_{19}$H$_{24}$O$_2$: 284.1776

B. 3'-[4-Benzyloxy-3-methylphenyl]-3'-[4-hydroxy-3-methylphenyl]pentane

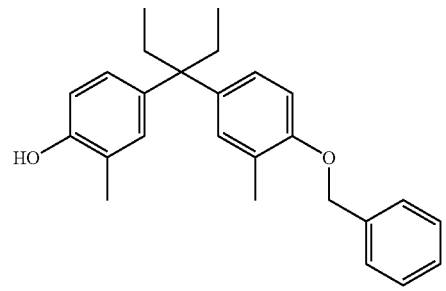

To a solution of 3,3-bis[4-hydroxy-3-methylphenyl]pentane (10 g, 35.2 mmol) and DMF (180 ml) is added 60% NaH disp (1.4 g, 35.2 mmol). After stirring for 30 m, to the reaction is added benzyl bromide (4.2 ml, 35.2 mmol). The mixture is stirred for 14 h and concentrated in vacuo. The residue is partitioned between Et$_2$O/water. The organic layer is washed with 1N HCl, water, brine, Na$_2$SO$_4$ dried, concentrated, and chromatographed (MeCl$_2$) to give the title compound as an oil (6.5 g, 49%)

High Res. FAB-MS: 374.2237; calc. for C$_{26}$H$_{30}$O$_2$: 374.2246

C. {4-[1-(4-Benzyloxy-3-methyl-phenyl)-1-ethyl-propyl]-2-methyl-phenoxy}-acetic acid methyl ester

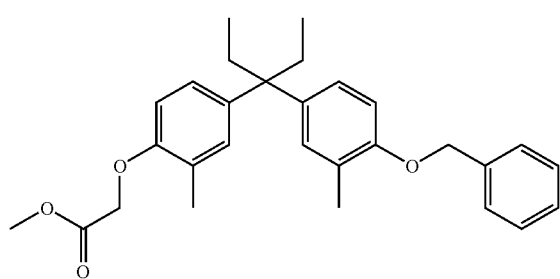

Using a procedure analogous to Example 3B, from 4-[1-(4-benzyloxy-3-methyl-phenyl)-1-ethyl-propyl]-2-methyl-phenol (9.76 g, 25.93 mmol) and methyl bromoacetate (2.7 mL, 28.53 mmol) gives the title compound (10.24 g, 22.96 mmol, 89%).

$^1$H NMR (CDCl$_3$), δ 0.61 (t, J=7.1 Hz, 6H), 2.04 (q, J=7.1 Hz, 4H), 2.23 (s, 3H), 2.24 (s, 3H), 3.80 (s, 3H), 4.62 (s, 2H), 5.05 (s, 2H), 6.58 (d, J=7.8 Hz, 1H), 6.77 (d, J=8.4 Hz, 1H), 6.90-6.97 (m, 4H), 7.29-7.48 (m, 5H).

ES-MS (m/z): calcd for C$_{29}$H$_{38}$NO$_4$ (M+NH$_4$)$^+$: 464.6; found: 464.3.

D. 3-{4-[1-(4-Benzyloxy-3-methyl-phenyl)-1-ethyl-propyl]-2-methyl-phenoxyethyl}-pentan-3-ol

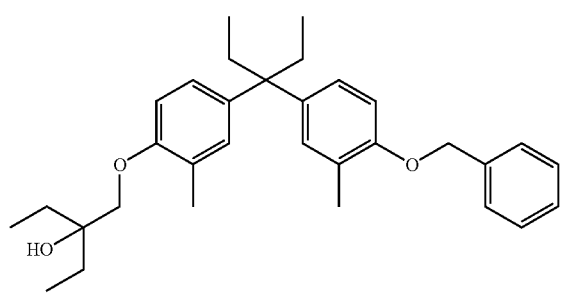

To a solution of {4-[1-(4-benzyloxy-3-methyl-phenyl)-1-ethyl-propyl]-2-methyl-phenoxy}-acetic acid methyl ester (4.78 g, 10.72 mmol) in THF (40 mL) at 0° C. is added 3.0 M EtMgBr (8.9 mL, 26.8 mmol) in a dropwise fashion. After the addition, it is stirred at 0° C. for 10 m, then refluxed for 3 h. The reaction mixture is poured into ice-H$_2$O, acidified with 0.1 M HCl and extracted with EtOAc (100 mL); MgSO$_4$ dried, and concentrated and chromatographed to give the title compound (4.06 g, 8.56 mmol, 80%).

$^1$H NMR (CDCl$_3$), δ 0.62 (t, J=7.4 Hz, 6H), 0.95 (t, J=7.4 Hz, 6H), 1.68 (q, J=7.4 Hz, 2H), 1.69 (q, J=7.4 Hz, 2H), 2.00-2.09 (m, 4H), 2.19 (s, 3H), 2.23 (s, 3H), 3.81 (s, 2H), 5.05 (s, 2H), 6.70 (d, J=8.4 Hz, 1H), 6.77 (d, J=7.8 Hz, 1H), 6.90-6.99 (m, 4H), 7.29-7.48 (m, 5H).

ES-MS (m/z): calcd for C$_{32}$H$_{46}$NO$_3$ (M+NH$_4$)$^+$: 492.7; found: 492.4.

E. Acetic acid 1-{4-[1-(4-benzyloxy-3-methyl-phenyl)-1-ethyl-propyl]-2-methyl-phenoxymethyl}-1-ethyl-propyl ester

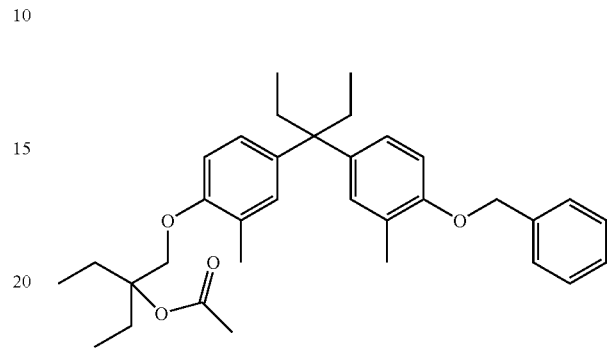

A reaction mixture containing 3-{4-[1-(4-benzyloxy-3-methyl-phenyl)-1-ethyl-propyl]-2-methyl-phenoxymethyl}-pentan-3-ol (3.92 g, 8.27 mmol), Et$_3$N (11.5 mL, 82.7 mmol) and Ac$_2$O (3.9 mL, 41.3 mmol), is stirred at rt for 3 h. It is diluted with EtOAc (100 mL), washed with 0.1 M HCl (2×60 mL) and brine (60 mL); MgSO$_4$ dried and concentrated to give the title compound (2.82 g, 5.47 mmol, 66%).

$^1$H NMR (CDCl$_3$), δ 0.62 (t, J=7.5 Hz, 6H), 0.91 (t, J=7.5 Hz, 6H), 1.98-2.09 (m, 11H), 2.16 (s, 3H), 2.24 (s, 3H), 4.13 (s, 2H), 5.05 (s, 2H), 6.69 (d, J=8.4 Hz, 1H), 6.77 (d, J=9.2 Hz, 1H), 6.90-6.98 (m, 4H), 7.29-7.47 (m, 5H).

ES-MS (m/z): calcd for C$_{34}$H$_{48}$NO$_4$(M+NH$_4$)$^+$: 534.7; found: 534.4.

F. Acetic acid 1-ethyl-1-{4-[1-ethyl-1-(4-hydroxy-3-methyl-phenyl)-propyl]-2-methyl-phenoxymethyl}-propyl ester

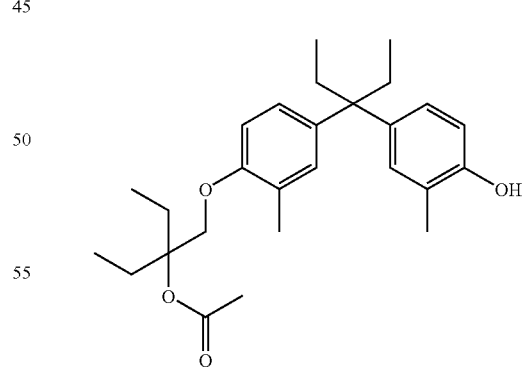

Acetic acid 1-{4-[1-(4-benzyloxy-3-methyl-phenyl)-1-ethyl-propyl]-2-methyl-phenoxymethyl}-1-ethyl-propyl ester (0.14 g g, 0.27 mmol), EtOH (20 ml), and 10% Pd/C (25 mg) is hydrogenated at atmospheric pressure for 18 h. The reaction is filtered through diatomaceous earth with EtOAc wash. The filtrate is concentrated to give the title compound (0.11 g, 0.25 mmol, 94%).

¹H NMR (CDCl₃), δ 0.61 (t, J=7.0 Hz, 6H), 0.91 (t, J=7.5 Hz, 6H), 1.97-2.09 (m, 11H), 2.16 (s, 3H), 2.21 (s, 3H), 4.13 (s, 2H), 6.65 (d, J=8.3 Hz, 1H), 6.69 (d, J=8.3 Hz, 1H), 6.84-6.96 (m, 4H).

ES-MS (m/z): calcd for $C_{27}H_{37}O_4$ (M–H)⁻: 425.6; found: 425.4.

D. Acetic acid 1-ethyl-1-{4-[1-ethyl-1-(3-methyl-4-trifluoromethanesulfonyloxy-phenyl)-propyl]-2-methyl-phenoxymethyl}-propyl ester

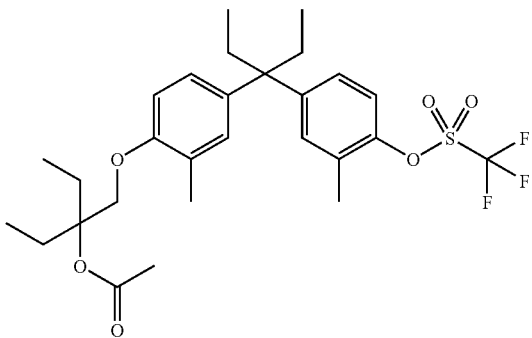

Using a procedure analogous to Example 1B, acetic acid 1-ethyl-1-{4-[1-ethyl-1-(4-hydroxy-3-methyl-phenyl)-propyl]-2-methyl-phenoxymethyl}-propyl ester (2.32 g, 5.43 mmol) gives the title compound (1.94 g, 3.48 mmol, 64%).

¹H NMR (CDCl₃), δ 0.61 (t, J=7.5 Hz, 6H), 0.90 (t, J=7.5 Hz; 6H), 1.97-2.10 (m, 11H), 2.15 (s, 3H), 2.56 (s, 3H), 4.13 (s, 2H), 6.69 (d, J=8.3 Hz, 1H), 6.83 (d, J=1.8 Hz, 1H), 6.92 (dd, J=8.4, 2.2 Hz, 1H), 7.03-7.05 (m, 2H), 7.79 (d, J=7.9 Hz, 1H). ES-MS (m/z): calcd for $C_{28}H_{41}F_3NO_6S$ (M+NH₄)⁺: 576.7; found: 576.3.

E. 4-{1-[4-(2-Acetoxy-2-ethyl-butoxy)-3-methyl-phenyl]-1-ethyl-propyl}-2-methyl-benzoic acid methyl ester

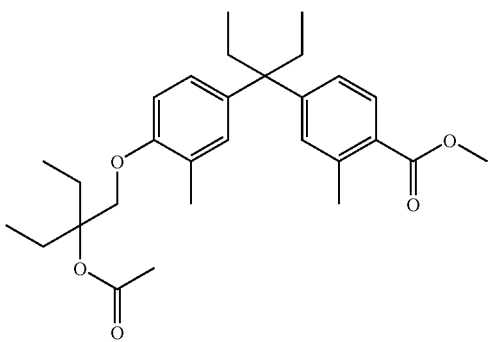

Using a procedure analogous to Example 1C, acetic acid 1-ethyl-1-{4-[1-ethyl-1-(3-methyl-4-trifluoromethanesulfonyloxy-phenyl)-propyl]-2-methyl-phenoxymethyl}-propyl ester (1.94 g, 3.48 mmol) gives the title compound (1.37 g, 2.95 mmol, 85%).

¹H NMR (CDCl₃), δ 0.61 (t, J=7.5 Hz, 6H), 0.90 (t, J=7.5 Hz, 6H), 1.97-2.11 (m, 1H), 2.15 (s, 3H), 2.56 (s, 3H), 3.87 (s, 3H), 4.13 (s, 2H), 6.69 (d, J=8.8 Hz, 1H), 6.83 (d, J=1.7 Hz, 1H), 6.92 (dd, J=8.4, 2.2 Hz, 1H), 7.02-7.07 (m, 2H), 7.79 (d, J=7.9 Hz, 1H).

ES-MS (m/z): calcd for $C_{29}H_{40}O_5$: 468.6; found: 468.0.

F. 4-{1-Ethyl-1-[4-(2-ethyl-2-hydroxy-butoxy)-3-methyl-phenyl]-propyl}-2-methyl-benzoic acid

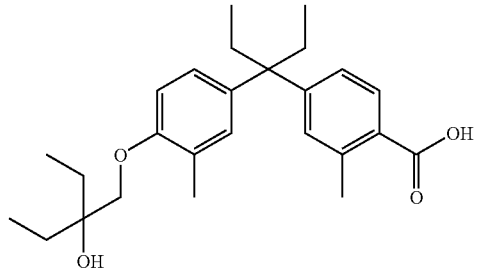

Using a procedure analogous to Example 1I, 4-{1-[4-(2-acetoxy-2-ethyl-butoxy)-3-methyl-phenyl]-1-ethyl-propyl}-2-methyl-benzoic acid methyl ester (1.38 g, 2.95 mmol) gives the title compound (0.96 g, 2.34 mmol, 79%).

¹H NMR (CDCl₃), δ 0.63 (t, J=7.0 Hz, 6H), 0.95 (t, J=7.0 Hz, 6H), 1.68 (q, J=7.0 Hz, 2H), 1.69 (q, J=7.0 Hz, 2H), 2.10 (q, J=7.0 Hz, 4H), 2.19 (s, 3H), 2.61 (s, 3H), 3.81 (s, 2H), 6.71 (d, J=8.4 Hz, 1H), 6.87 (d, J=1.7 Hz, 1H), 6.94 (dd, J=8.4, 2.3 Hz, 1H), 7.06-7.10 (m, 2H), 7.94 (d, J=8.8 Hz, 1H).

ES-MS (m/z): calcd for $C_{26}H_{35}O_4$ (M–H)⁻: 411.6; found: 411.3.

G. (4-{1-Ethyl-1-[4-(2-ethyl-2-hydroxy-butoxy)-3-methyl-phenyl]-propyl}-2-methyl-benzoylamino)-acetic acid methyl ester

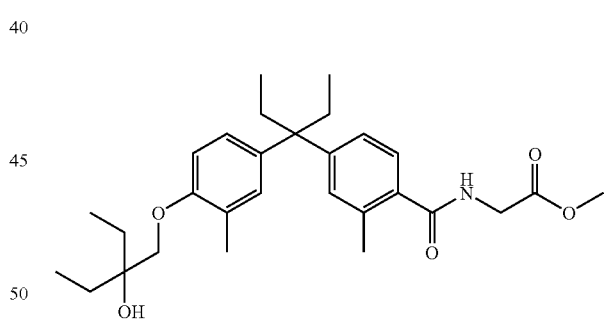

Using a procedure analogous to Example 1J, 4-{1-ethyl-1-[4-(2-ethyl-2-hydroxy-butoxy)-3-methyl-phenyl]-propyl}-2-methyl-benzoic acid (0.64 g, 1.55 mmol) and glycine methyl ester hydrochloride (195 mg, 1.55 mmol) gives the title compound (0.72 g, 1.49 mmol, 96%). %).

¹H NMR (CDCl₃), δ 0.62 (t, J=7.0 Hz, 6H), 0.95 (t, J=7.0 Hz, 6H), 1.68 (q, J=7.0 Hz, 2H), 1.69 (q, J=7.0 Hz, 2H), 2.07 (q, J=7.0 Hz, 4H), 2.19 (s, 3H), 2.44 (s, 3H), 3.80 (s, 3H), 3.81 (s, 2H), 4.24 (d, J=5.4 Hz, 2H), 6.28 (t, J=5.4 Hz, 1H), 6.70 (d, J=8.3 Hz, 1H), 6.85 (d, J=2.2 Hz, 1H), 6.94 (dd, J=8.4, 2.2 Hz, 1H), 6.99-7.05 (m, 2H), 7.31 (d, J=7.9 Hz, 1H).

ES-MS (m/z): calcd for $C_{29}H_{42}NO_5$ (M+H)⁺: 484.6; found: 484.4.

H. (4-{1-Ethyl-1-[4-(2-ethyl-2-hydroxy-butoxy)-3-methyl-phenyl]-propyl}-2-methyl-benzoylamino)-acetic acid

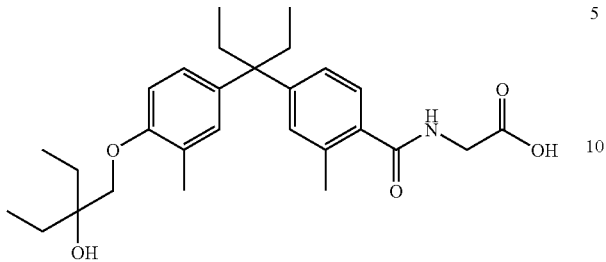

Using a procedure analogous to Example 1I, (4-{1-ethyl-1-[4-(2-ethyl-2-hydroxy-butoxy)-3-methyl-phenyl]-propyl}-2-methyl-benzoylamino)-acetic acid methyl ester (0.72 g, 1.48 mmol) gives the title compound (0.45 g, 0.97 mmol, 657%).

$^1$H NMR (CDCl$_3$), δ 0.62 (t, J=7.4 Hz, 6H), 0.95 (q, J=7.4 Hz, 6H), 1.68 (q, J=7.4 Hz, 2H), 1.69 (q, J=7.4 Hz, 2H), 2.06 (q, J=7.4 Hz, 4H), 2.12 (s, 3H), 2.43 (s, 3H), 3.81 (s, 2H), 4.26 (d, J=5.2 Hz, 2H), 6.35 (t, J=5.2 Hz, 1H), 6.70 (d, J=8.4 Hz, 1H), 6.84 (d, J=1.8 Hz, 1H), 6.93 (dd, J=8.4, 2.2 Hz, 1H), 6.99-7.06 (m, 2H), 7.31 (d, J=8.4 Hz, 1H).

ES-MS (m/z): calcd for C$_{28}$H$_{38}$NO$_5$ (M–H)$^-$: 468.6; found: 468.4.

Example 4

Preparation of (4-{1-Ethyl-1-[4-(2-hydroxy-2-isopropyl-3-methyl-butoxy)-3-methyl-phenyl]-propyl}-2-methyl-benzoylamino)-acetic acid

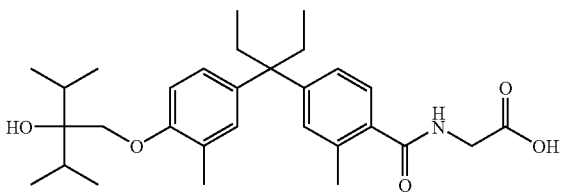

A. {4-[1-(4-Benzyloxy-3-methyl-phenyl)-1-ethyl-propyl]-2-methyl-phenoxy}-acetic acid

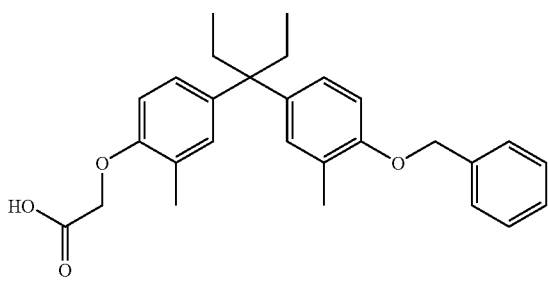

Using a procedure analogous to Example 1I, from {4-[1-(4-benzyloxy-3-methyl-phenyl)-1-ethyl-propyl]-2-methyl-phenoxy}-acetic acid methyl ester (1.58 g, 3.54 mmol) gives the title compound (1.47 g, 3.40 mmol, 96%).

$^1$H NMR (CDCl$_3$), δ 0.61 (t, J=7.5 Hz, 6H), 2.04 (q, J=7.5 Hz, 4H), 2.23 (s, 3H), 2.24 (s, 3H), 4.67 (s, 2H), 5.05 (s, 2H), 6.62 (d, J=8.8 Hz, 1H), 6.77 (d, J=8.3 Hz, 1H), 6.90-6.98 (m, 4H), 7.29-7.47 (m, 5H). ES-MS (m/z): calcd for C$_{28}$H$_{31}$O$_4$ (M–H)$^-$: 431.6; found: 431.3.

B. 2-{4-[1-(4-Benzyloxy-3-methyl-phenyl)-1-ethyl-propyl]-2-methyl-phenoxy}-N-methoxy-N-methyl-acetamide

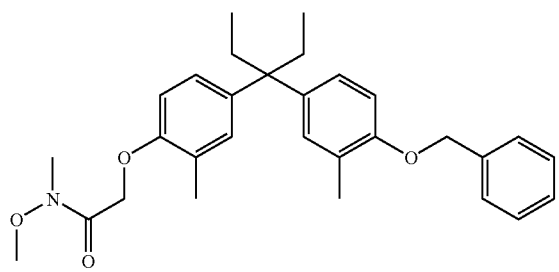

Using an analogous procedure to Example 1J, {4-[1-(4-benzyloxy-3-methyl-phenyl)-1-ethyl-propyl]-2-methyl-phenoxy}-acetic acid (1.46 g, 3.38 mmol) and N,O-dimethylmethylhydroxyamine hydrochloride (363 mg, 3.72 mmol) give the title compound (1.24 g, 2.61 mmol, 77%).

$^1$H NMR (CDCl$_3$), δ 0.61 (t, J=7.5 Hz, 6H), 2.03 (q, J=7.5 Hz, 4H), 2.23 (s, 3H), 2.25 (s, 3H), 3.25 (s, 3H), 3.76 (s, 3H), 4.80 (s, 2H), 5.04 (s, 2H), 6.64 (d, J=9.2 Hz, 1H), 6.77 (d, J=8.4 Hz, 1H), 6.90-6.98 (m, 4H), 7.29-7.47 (m, 5H).

ES-MS (m/z): calcd for C$_{30}$H$_{38}$NO$_4$ (M+H)$^+$: 476.6; found: 476.4.

C. 1-{4-[1-(4-Benzyloxy-3-methyl-phenyl)-1-ethyl-propyl]-2-methyl-phenoxy}-3-methyl-butan-2-one

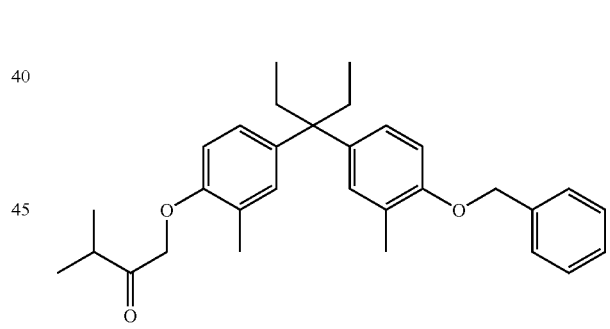

To a 0° C. solution of 2-{4-[1-(4-benzyloxy-3-methyl-phenyl)-1-ethyl-propyl]-2-methyl-phenoxy}-N-methoxy-N-methyl-acetamide (2.36 g, 4.98 mmol) in THF (50 mL) is added 2.0 M iPrMgCl (3.0 mL, 5.98 mmol). The reaction is stirred at 0° C. for 30 m, then at RT for 1 h. It is quenched with satd NH$_4$Cl (20 mL), diluted with H$_2$O (50 mL), extracted with EtOAc (2×100 mL), washed with 0.1 M HCl (50 mL), H$_2$O (50 mL); MgSO$_4$ dried, concentrated and purified to give the title compound (1.01 g, 2.21 mmol, 44%).

$^1$H NMR (CDCl$_3$), δ 0.61 (t, J=7.5 Hz, 6H), 1.17 (d, J=7.0 Hz, 6H), 2.03 (q, J=7.5 Hz, 4H), 2.23 (s, 3H), 2.25 (s, 3H), 3.07 (quintet, J=7.0 Hz, 1H), 4.58 (s, 2H), 5.04 (s, 2H), 6.55 (d, J=8.8 Hz, 1H), 6.77 (d, J=8.4 Hz, 1H), 6.90-6.97 (m, 4H), 7.29-7.47 (m, 5H).

ES-MS (m/z): calcd for C$_{31}$H$_{42}$NO$_3$ (M+NH$_4$)$^+$: 476.7; found: 476.4.

D. 3-{4-[1-(4-Benzyloxy-3-methyl-phenyl)-1-ethyl-propyl]-2-methyl-phenoxymethyl}-2,4-dimethyl-pentan-3-ol

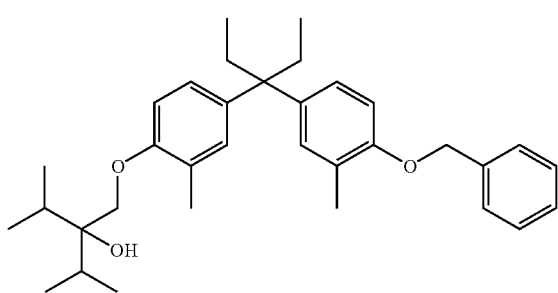

Anhydrous CeCl₃ (0.82 g) is suspended in THF (30 mL) with stirring overnight. It is cooled to 0° C., treated with 2.0 M iPrMgCl (1.3 mL) and stirred at 0° C. for 1 h. A solution of 1-{4-[1-(4-benzyloxy-3-methyl-phenyl)-1-ethyl-propyl]-2-methyl-phenoxy}-3-methyl-butan-2-one (1.01 g, 2.21 mmol) in THF (10 mL) is added. The mixture is stirred at 0° C. for 1 h, before it is quenched with 0.1 M HCl (20 mL). It is extracted with EtOAc (200 mL), washed with 0.1 M HCl (3×50 mL); MgSO₄ dried and concentrated to give the title compound (1.10 g, 2.19 mmol, 99%). $^1$H NMR (CDCl₃), δ 0.62 (t, J=7.0 Hz, 6H), 1.01 (d, J=7.1 Hz, 6H), 1.04 (d, J=7.1 Hz, 6H), 1.57 (b, 2H), 2.04 (q, J=7.0 Hz, 4H), 2.17 (s, 3H), 2.24 (s, 3H), 3.88 (s, 2H), 5.04 (s, 2H), 6.70 (d, J=8.3 Hz, 1H), 6.77 (d, J=9.2 Hz, 1H), 6.90 (d, J=2.2 Hz, 1H), 6.93-6.98 (m, 3H), 7.29-7.47 (m, 5H).

ES-MS (m/z): calcd for $C_{34}H_{50}NO_3$ $(M+NH_4)^+$: 520.7; found: 520.63.

E. 4-{1-Ethyl-1-[4-(2-hydroxy-2-isopropyl-3-methyl-butoxy)-3-methyl-phenyl]-propyl}-2-methyl-phenol

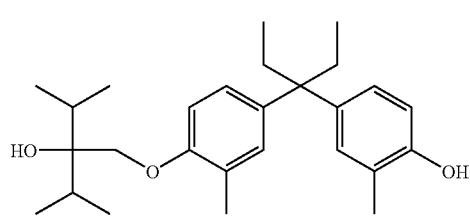

Using a procedure analogous to Example 3F, 3-{4-[1-(4-benzyloxy-3-methyl-phenyl)-1-ethyl-propyl]-2-methyl-phenoxymethyl}-2,4-dimethyl-pentan-3-ol (5.06 g, 10.07 mmol) gives the title compound (3.97 g, 9.64 mmol, 96%). $^1$H NMR (CDCl₃), δ 0.62 (t, J=7.4 Hz, 6H), 1.00-1.06 (m, 12H), 2.03 (q, J=7.2 Hz, 4H), 2.11-2.20 (m, 2H), 2.17 (s, 3H), 2.21 (s, 3H), 3.89 (s, 2H), 6.65 (d, J=8.5 Hz, 1H), 6.70 (d, J=8.3 Hz, 1H), 6.87 (dd, J=8.3, 2.2 Hz, 1H), 6.90 (dd, J=10.0, 2.2 Hz, 1H), 6.89-6.93 (m, 2H), 6.96 (dd, J=8.5, 2.2 Hz, 1H).

F. Trifluoro-methanesulfonic acid 4-{1-ethyl-1-[4-(2-hydroxy-2-isopropyl-3-methyl-butoxy)-3-methyl-phenyl]-propyl}-2-methyl-phenyl ester

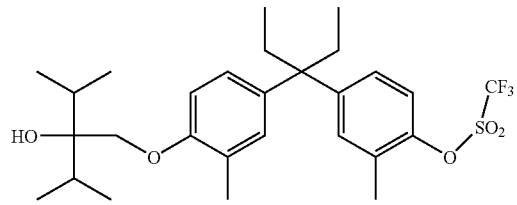

Using a procedure analogous to Example 1B, 4-{1-ethyl-1-[4-(2-hydroxy-2-isopropyl-3-methyl-butoxy)-3-methyl-phenyl]-propyl}-2-methyl-phenol (3.79 g, 9.21 mmol) gives the title compound (1.90 g, 3.49 mmol, 38%).

$^1$H NMR (CDCl₃), δ 0.62 (t, J=7.2 Hz, 6H), 1.00-1.06 (m, 12H), 2.05 (q, J=7.4 Hz, 4H), 2.11-2.20 (m, 2H), 2.18 (s, 3H), 2.33 (s, 3H), 3.89 (s, 2H), 6.62 (d, J=8.4 Hz, 1H), 6.85 (d, J=2.3 Hz, 1H), 6.93 (dd, J=8.6, 2.3 Hz, 1H), 7.04 (dd, J=8.6, 2.1 Hz, 1H), 7.09 (s, 1H), 7.10 (d, J=6.4 Hz, 1H).

G. 4-{1-Ethyl-1-[4-(2-hydroxy-2-isopropyl-3-methyl-butoxy)-3-methyl-phenyl]-propyl}-2-methyl-benzoic acid methyl ester

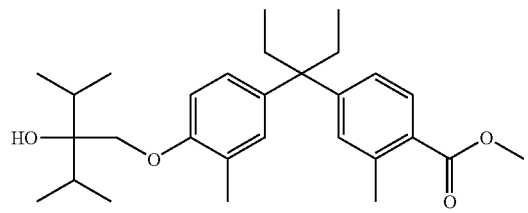

Using a procedure analogous to Example 1C, from trifluoro-methanesulfonic acid 4-{1-ethyl-1-[4-(2-hydroxy-2-isopropyl-3-methyl-butoxy)-3-methyl-phenyl]-propyl}-2-methyl-phenyl ester (3.80 g, 6.98 mmol) to give the title compound (2.75 g, 6.05 mmol, 87%).

$^1$H NMR (CDCl₃), δ 0.61 (t, J=7.2 Hz, 6H), 0.98-1.04 (m, 12H), 2.07 (q, J=7.2 Hz, 4H), 2.10-2.18 (m, 2H), 2.15 (s, 3H), 2.56 (s, 3H), 3.86 (s, 3H), 3.88 (s, 2H), 6.70 (d, J=8.7 Hz, 1H), 6.84 (d, J=1.6 Hz, 1H), 6.93 (dd, J=8.5, 2.5 Hz, 1H), 7.04 (dd, J=8.5, 1.6 Hz, 1H), 7.06 (s, 1H), 7.79 (d, J=7.8 Hz, 1H).

H. 4-{1-Ethyl-1-[4-(2-hydroxy-2-isopropyl-3-methyl-butoxy)-3-methyl-phenyl]-propyl}-2-methyl-benzoic acid

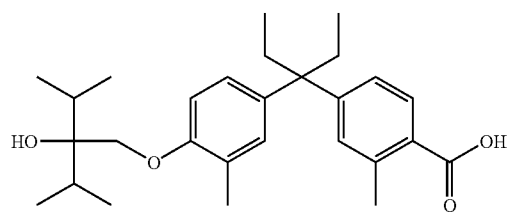

Using a procedure analogous to Example 1I, 4-{1-ethyl-1-[4-(2-hydroxy-2-isopropyl-3-methyl-butoxy)-3-methyl-phenyl]-propyl}-2-methyl-benzoic acid methyl ester (0.30 g, 0.59 mmol) gives the title compound (0.96 g, 2.18 mmol, 56%).

$^1$H NMR (CDCl$_3$), δ 0.63 (t, J=7.3 Hz, 6H), 1.00-1.06 (m, 12H), 2.10 (q, J=7.2 Hz, 4H), 2.12-2.19 (m, 2H), 2.17 (s, 3H), 2.62 (s, 3H), 3.89 (s, 2H), 6.71 (d, J=8.4 Hz, 1H), 6.86 (d, J=1.7 Hz, 1H), 6.94 (dd, J=8.6, 2.5 Hz, 1H), 7.08 (dd, J=8.4, 1.7 Hz, 1H), 7.09 (s, 1H), 7.94 (d, J=8.4 Hz, 1H).

ES-MS (m/z): calcd. for C$_{28}$H$_{39}$NO$_4$ (M−H)$^−$: 439.6; found: 439.2.

I. Preparation of (4-{1-Ethyl-1-[4-(2-hydroxy-2-isopropyl-3-methyl-butoxy)-3-methyl-phenyl]-propyl}-2-methyl-benzoylamino)-acetic acid methyl ester

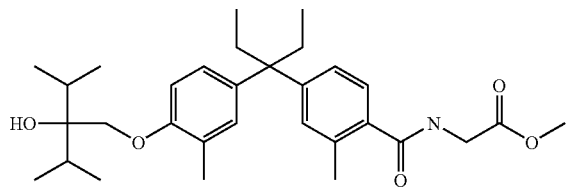

Using a procedure analogous to Example 1J, 4-{1-ethyl-1-[4-(2-hydroxy-2-isopropyl-3-methyl-butoxy)-3-methyl-phenyl]-propyl}-2-methyl-benzoic acid (0.30 g, 0.68 mmol) and glycine methyl ester hydrochloride (0.094 g, 0.75 mmol) gives the titled compound (0.30 g, 0.59 mmol, 86%).

$^1$H NMR (CDCl$_3$), δ 0.62 (t, J=7.5 Hz, 6H), 0.98-1.06 (m, 12H), 2.07 (q, J=7.2 Hz, 4H), 2.10-2.19 (m, 2H), 2.16 (s, 3H), 2.44 (s, 3H), 3.80 (s, 2H), 3.89 (s, 1H), 4.23 (d, J=5.1 Hz), 6.29 (t, J=5.1 Hz), 6.70 (d, J=8.7 Hz), 6.84 (d, J=2.2 Hz, 1H), 6.94 (dd, J=8.7, 2.2 Hz, 1H), 7.01 (d, J=8.2 Hz, 1H), 7.05 (s, 1H), 7.32 (d, J=8.2 Hz, 1H).

J. (4-{1-Ethyl-1-[4-(2-hydroxy-2-isopropyl-3-methyl-butoxy)-3-methyl-phenyl]-propyl}-2-methyl-benzoylamino)-acetic acid Using a procedure analogous to Example 1I, (4-{1-ethyl-1-[4-(2-hydroxy-2-isopropyl-3-methyl-butoxy)-3-methyl-phenyl]-propyl}-2-methyl-benzoylamino)-acetic acid methyl ester (0.30 g, 0.59 mmol) gives the title compound (0.25 g, 0.50 mmol, 86%.

$^1$H NMR (CDCl$_3$), δ 0.61 (t, J=7.4 Hz, 6H), 0.98-1.06 (m, 12H), 2.06 (q, J=7.4 Hz, 4H), 2.10-2.19 (m, 2H), 2.16 (s, 3H), 2.43 (s, 3H), 3.89 (s, 2H), 4.25 (d, J=5.2 Hz, 2H), 6.40 (t, J=5.2 Hz, 1H), 6.70 (d, J=8.6 Hz, 1H), 6.83 (d, J=2.0 Hz, 1H), 6.93 (dd, J=8.3, 2.0 Hz, 1H), 7.01 (d, J=8.0 Hz, 1H), 7.05 (s, 1H), 7.31 (d, J=8.0 Hz, 1H).

ES-MS (m/z): calcd. for C$_{30}$H$_{42}$NO$_5$ (M−H)$^−$: 496.3; found: 496.6.

Compounds of the Invention—Salts, Stereoisomers, & Prodrugs:

Salts of the compounds represented by formulae I are an additional aspect of the invention. The skilled artisan will also appreciate that the family of compounds of formulae I include acidic and basic members and that the present invention includes pharmaceutically acceptable salts thereof.

In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, ammonium, calcium, magnesium, aluminum, zinc, and the like. Sodium and potassium salts are particularly preferred. Salts are conveniently prepared from the free acid by treating the acid in solution with a base or by exposing the acid to an ion exchange resin. For example, a carboxylic acid substituent on the compound of Formula I may be selected as —CO$_2$H and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, choline, clavulanate, citrate, chloride, chloroprocaine, choline, diethanolamine, dihydrochloride, diphosphate, edetate, edisylate, estolate, esylate, ethylenediamine, fluoride, fumarate, gluceptate, gluconate, glutamate, glycolylarsanilate, hexylresorcinate, hydrabamine, bromide, chloride, hydrobromide, hydrochloride, hydroxynaphthoate, iodide, isothionate, lactate, lactobionate, laurate, malate, maleate, malseate, mandelate, meglumine, mesylate, mesviate, methylbromide, methylnitrate, methylsulfate, mucate, napsylate, nitrate, oleate, oxalate, palmitate, pamoate, pantothenate, phosphate, polygalacturonate, procane, salicylate, stearate, subacetate, succinate, sulfate, tannate, tartrate, teoclate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a chiral column may be used such as those sold by Daicel Chemical Industries identified by the trademarks:

CHIRALPAK AD, CHIRALPAK AS, CHIRALPAK OD, CHIRALPAK OJ, CHIRALPAK OA, CHIRALPAK OB, CHIRALPAK OC, CHIRALPAK OF, CHIRALPAK OG, CHIRALPAK OK, and CHIRALPAK CA-1.

By another conventional method, a racemic mixture may be reacted with a single enantiomer of some other compound. This changes the racemic form into a mixture of diastereomers. These diastereomers, because they have different melting points, different boiling points, and different solubilities can be separated by conventional means, such as crystallization.

The present invention is also embodied in mixtures of compounds of formulae I.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters. Particularly preferred esters to use as prodrugs are; methyl, ethyl, propyl, isopropyl, n-butyl, isobutyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula I (in a medium such as dimethylformamide) 4-(2-chloroethyl)morpholine hydrochloride (available from Aldrich Chemical Co., Milwaukee, Wis. USA, Item No. C5,220-3). For example, prodrugs may be prepared by: reaction of the sodium salt for a compound of Formula I with;

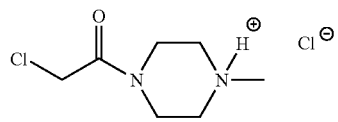

and sodium iodide to provide the ester prodrug pendent group

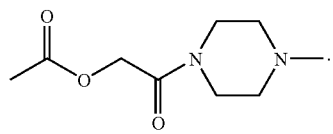

Also, lower alkyl (viz., $C_1$-$C_8$) ester prodrugs may be prepared by conventional means such as reacting the sodium or potassium salt (derived by forming the salt of any acidic compound of the invention; viz., reaction of a base such as KOH with an acidic group such as —$CO_2H$) of a compound of Formula I with an alkyl iodide such as methyl iodide, ethyl iodide, n-propyl iodide, isopropyl iodide. Typical ester prodrug substituents are

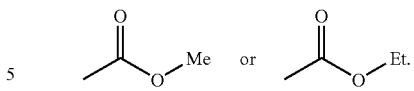

Pharmaceutical Formulations Containing the Novel Compounds of the Invention:

Pharmaceutical formulations of the invention are prepared by combining (e.g., mixing) a therapeutically effective amount of the compound of the invention (compounds of Formula I) together with a pharmaceutically acceptable carrier or diluent. The present pharmaceutical formulations are prepared by known procedures using well-known and readily available ingredients.

In making the compositions of the present invention, the compounds of Formula I will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the compound. The compounds of the present invention are preferably formulated prior to administration.

The compounds of the invention may also be delivered by suitable formulations contained in a transderm patch. Alternatively, the compounds of the invention may be delived to a patient by sublingual administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the compound of Formula I is mixed with a carrier having the necessary binding properties in suitable proportions and compacted in the shape and size desired. The powders and tablets preferably contain from about 1 to about 99 weight percent of the compound which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active Ingredient may be dissolved or suspended in a pharmaceutically acceptable carrier, such as sterile water, sterile organic solvent or a mixture of both. The compounds can often be dissolved in a suitable organic solvent, for instance aqueous propylene glycol. Other compositions can be made by dispersing the finely divided compounds of the invention in aqueous starch or sodium carboxymethyl cellulose solution or in a suitable oil.

Methods of Using the Compounds of the Invention:

Many disease states are benefited by treatment with the compounds of Formula I include, but are not limited to:
- disease states characterized by abnormal calcium regulation
- disease states characterized by abnormal cell proliferation
- disease states characterized by abnormal cell differentiation
- disease states characterized by abnormal immune response
- disease states characterized by abnormal dermatological conditions
- disease states characterized by neurodegenerative condition
- disease states characterized by inflammation
- disease states characterized by vitamin D sensitivity
- disease states characterized by hyperproliferative disorders.

Specific disease states benefited by treatment of the compounds of Formula I and II include, but are not limited to:
- Acne
- Actinic keratosis
- Alopecia
- Alzheimer's disease
- Benign prostatic hyperplasia
- Bladder cancer
- Bone maintenance in zero gravity
- Bone fracture healing
- Breast cancer
- Chemoprovention of Cancer
- Crohn's disease
- Colon cancer
- Type I diabetes
- Host-graft rejection
- Hypercalcemia
- Type II diabetes
- Leukemia
- Multiple sclerosis
- Myelodysplastic syndrome
- Insufficient sebum secretion
- Osteomalacia
- Osteoporosis
- Insufficient dermal firmness
- Insufficient dermal hydration
- Psoriatic arthritis
- Prostate cancer
- Psoriasis
- Renal osteodystrophy
- Rheumatoid arthritis
- Scleroderma
- Skin cancer
- Systemic lupus erythematosus
- Skin cell protection from Mustard vesicants
- Ulcerative colitis
- Vitiligo
- Wrinkles Particularly preferred is the treatment of psoriasis and osteoporosis by administration to a mammal (including a human) of a therapeutically effective amount of compounds of Formulae I. By "pharmaceutically effective amount" it is meant that quantity of pharmaceutical agent corresponding to formulae I which prevents, removes or reduces the deleterious effects of a disease state in mammals, including humans.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a pharmaceutically effective amount typically in the range of from about 0.0001 mg/kg/day to about 50 mg/kg/day of body weight of an active compound of this invention. Preferably the dose of compounds of the invention will be from 0.0001 to 5 mg/kg/day of body weight.

Preferably compounds of the invention (e.g., per Formula I) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.0001 to about 1000 milligrams or more according to the particular treatment involved. It may be appreciated that it is necessary to make routine variations to the dosage depending on the age and condition of the patient. Dosage will also depend on the route of administration. The compounds of the invention may be administered by a variety of routes including oral, aerosol, rectal, transdermal, sublingual, subcutaneous, intravenous, intramuscular, and intranasal. Particularly preferred is the treatment of psoriasis with an ointment type formulation containing the compounds of the invention. The ointment formulation may be applied as needed, typically from one to 6 times daily.

Treatment of psoriasis is preferably done with topical application by a formulation in the form of a cream, oil, emulsion, paste or ointment containing a therapeutically effective amount of a compound of the invention. The formulation for topical treatment contains from 0.5 to 0.00005 weight percent, preferably from 0.05 to 0.0005 weight percent, and most preferably from 0.025 to 0.001 of a Active Ingredient.

For example, two semisolid topical preparations useful as vehicles for VDR modulators in treatment and prevention of psoriasis are as follows:

Polyethylene Glycol Ointment USP (p. 2495)
Prepare Polyethylene Glycol Ointment as follows:

| Polyethylene Glycol 3350 | 400 g. |
| Polyethylene Glycol 400 | 600 g. |
| To make | 1000 g. |

Heat the two ingredients on a water bath to 65 C. Allow to cool, and stir until congealed. If a firmer preparation is desired, replace up to 100 g of the polyethylene glycol 400 with an equal amount of polyethylene glycol 3350.

Hydrophilic Ointment USP (p. 1216)
Prepare Hydrophilic Ointment as follows:

| Methylparaben | 0.25 g. |
| Propylparaben | 0.15 g. |
| Sodium Lauryl Sulfate | 10 g. |
| Propylene Glycol | 120 g. |
| Stearyl Alcohol | 250 g. |
| White Petrolatum | 250 g. |
| Purified Water | 370 g. |
| To make about | 1000 g. |

The Stearyl Alcohol and White Petrolatum are melted on a steam bath, and warmed to about 75 C. The other ingredients, previously dissolved in the water are added, warmed to 75 C, and the mixture stirred until it congeals.

For each of the above formulations the Active Ingredient is added during the heating step in an amount that is from 0.5 to 0.00005 weight percent, preferably from 0.05 to 0.0005 weight percent, and most preferably from 0.025 to 0.001 weight percent of the total ointment weight. (Source:— United States Pharmacopoeia 24, United States Pharmacopeial Convention, 1999)

Conventional therapy for osteoporosis includes; (i) estrogens, (ii) androgens, (iii) calcium supplements, (iv) vitamin D metabolites, (v) thiazide diuretics, (vi) calcitonin, (vii) bisphosphonates, (viii) SERMS, and (ix) fluorides (see, Harrison's Principles of Internal Medicine, 13$^{th}$ edition, 1994, published by McGraw Hill Publ., ISBN 0-07-032370-4, pgs. 2172-77; the disclosure of which is incorporated herein by reference). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be administered separately or simultaneously with a conventional therapy. Alternatively, the vitamin D receptor modulator compounds of the invention may be combined with conventional therapeutic agents in a formulation for treatment of osteoporosis such as set out below:

A formulation for treating osteoporosis comprising:
Ingredient (A1): a vitamin D receptor modulator represented by formula (I), or a pharmaceutically acceptable salt or prodrug derivative thereof;
Ingredient (B1):
   one or more co-agents that are conventional for treatment osteoporosis selected from the group consisting of:
   a. estrogens,
   b. androgens,
   c. calcium supplements,
   d. vitamin D metabolites,
   e. thiazide diuretics,
   f. calcitonin,
   g. bisphosphonates,
   h. SERMS, and
   i. fluorides.
Ingredient (C1): optionally, a carrier or diluent.

Typically useful formulations are those wherein the weight ratio of (A1) to (B1) is from 10:1 to 1:1000 and preferably from 1:1 to 1:100.

Combination Therapy for Psoriasis:

Conventional therapy for psoriasis includes topical glucocorticoids, salicylic acid, crude coal tar, ultraviolet light, and methotrexate (see, Harrison's Principles of Internal Medicine, 13$^{th}$ edition, 1994, published by McGraw Hill Publ., ISBN 0-07-032370-4, pgs. 2172-77). Any one or combination of these conventional therapies may be used in combination with the method of treatment using compounds of Formulae I as taught herein. For example, in a method of treating osteoporosis, the vitamin D receptor modulator compounds of the invention (e.g., as defined by formula I) may be topically administered separately or simultaneously with a conventional therapy. Alternatively, the vitamin D receptor modulator compounds of the invention may be combined with conventional therapeutic agents in a topically applied formulation for treatment of osteoporosis such as set out below:

A formulation for treating osteoporosis comprising:
Ingredient (A2): a vitamin D receptor modulator represented by formula (I), or a pharmaceutically acceptable salt or prodrug derivative thereof;
Ingredient (B2):
   one or more co-agents that are conventional for treatment osteoporosis selected from the group consisting of:
   a. topical glucocorticoids,
   b. salicylic acid, or
   c. crude coal tar.
Ingredient (C2): optionally, a carrier or diluent.

Typically useful formulations are those wherein the weight ratio of (A2) to (B2) is from 1:10 to 1:100000 and preferably from 1:100 to 1:10000.

Experimental Results:

Table 1 of Experimental Results

| Test Cmpd.[1] | RXR-VDR (SaOS-2 cells)[2] EC$_{50}$ (nM) | VDR CTF (Caco-2 cells)[3] EC$_{50}$ (nM) | OCN Promoter[4] EC$_{50}$ (nM) | Mouse Hypercal[5] μg/Kg/d |
|---|---|---|---|---|
| Ex. 1 | 68.6 | 471 | 0.96 | 3000 |
| Ex. 2 | 111.9/9.4 | 397 | 1.2/1.7 | 300 |
| Ex. 3 | 300.7/148.9 | 819 | 16.8/19.7 | 1000 |
| Ex. 4 | 257/127.3 | 974 | 21/27.7 | 73000 |
| AA | 5.02 | 16 | 5 | 0.06 |
| BB | 10.32 | 169.81 | 8.24 | 20 |
| CC | 2427.7 |  | 2680.9 |  |
| DD | 109.44 |  | 31.1 | 1000 |
| EE | 429.99 | 891.16 | 341.25 | 1000 |
| FF | 3/1 | 57 | 0.28 |  |

Table 2 of Experimantal Results

| Test Cmpd.[1] | Kera. Prolif. IC$_{50}$ (nM) | IL-10 IC$_{50}$ (nM) |
|---|---|---|
| Ex. 1 |  |  |
| Ex. 2 | 21 | 24 |
| Ex. 3 | 121 | 718 |
| Ex. 4 |  | 477 |
| AA | 120 | 1.2 |
| BB | 10 | 28 |
| CC |  |  |
| DD | 1060 |  |
| EE |  |  |
| FF | 103 | 0.5 |

Explanation of Table 5 and 6 Column Numerical Superscripts:

1. Test Compound numbers refer to the products of the corresponding Example Nos. that is, compounds within the scope of the invention. For example, the number "Ex. 2" refers to the compound, 3'-[4-(2-hydroxy-3,3-dimethylbutoxy)-3-methylphenyl]-3'-[5-methoxycarbonyl-4-methylthiophen-2-yl]pentane, prepared in Example 2. The control experiments are done with the double letter coded compounds identified as follows:

"AA"=1α,25-dihydroxyvitamin D$_3$

"BB"=3-(4-{1-Ethyl-1-[4-(2-hydroxy-3,3-dimethyl-butoxy)-3-methyl-phenyl]-propyl}-2-methyl-phenoxy)-propane-1,2-diol "CC"=1-(4-{1-[4-(3,3-Dimethyl-2-oxo-butoxy)-3-methyl-phenyl]-cyclohexyl}-2-methyl-phenoxy)-3,3-dimethyl-butan-2-one

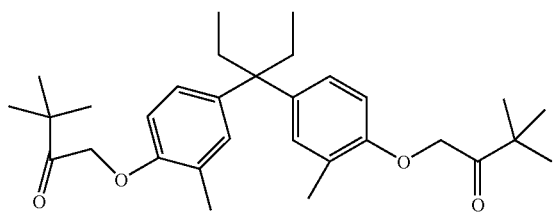

"DD"=compound represented by the formula:
"EE"=compound represented by the formula:

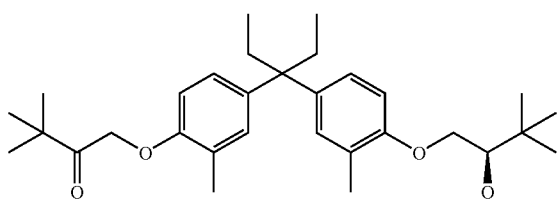

"FF"=calcipotriol (structural formula below):

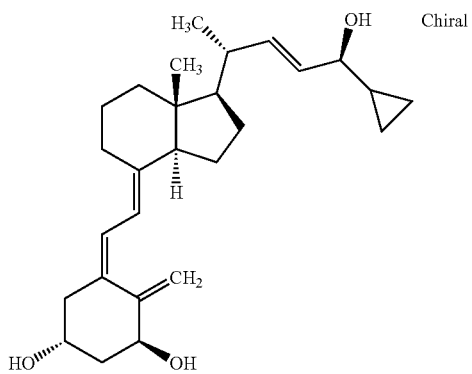

2. The RXR-VDR heterodimerization (SaOS-2 cells) test is described in the "Assay" section of the Description, infra.

3. The VDR CTF (Caco-2 cells) test is described in the "Assay" section of the Description, infra.

4. The OCN Promoter test is described in the "Assay" section of the Description, infra.

5. The Mouse Hypercalcemia test is described in the "Assay" section of the Description, infra.

6. The keratinocyte proliferation assay is described in the "Assay" section of the Description, infra.

7. The IL-10 induction assay is described in the "Assay" section of the Description, infra.

Assay Methods

Use of the Assay Methods:

The evaluation of the novel compounds of the invention for osteoporosis and other related diseases is done using a plurality of test results. The use of multiple assays is necessary since the combined properties of (i) high activity for the vitamin D receptor, and (ii) prevention of hypercalcemia must be achieved to have utility for the methods of treating diseases, which are also, aspects of this invention. Some of the tests described below are believed related to other tests and measure related properties of compounds. Consequently, a compound may be considered to have utility in the practice of the invention if is meets most, if not all, of the acceptance criteria for the above described tests.

The evaluation of the novel compounds of the invention for psoriasis is done using the Keratinocyte Proliferation Assay in combination with other assays that measure inhibition of IL-2 production and stimulation of IL-10 production in peripheral blood mononuclear cells (PBMCs).

Brief Description, Utility and Acceptance Criteria for the Assay Methods:

1. The RXR-VDR Heterodimer Assay:

This assay provides the VDR activity of a test compound. It is desirable to have low EC50 values for a compound in this assay. The lower the EC50 value, the more active the compound will be as a VDR agonist. Desired assay results are EC50 values less than or equal to 600 nM. Preferred assay results are less than 250 nM, and most preferably less than 150 nM.

2. The Caco-2 Cell Co-Transfection Assay:

The Caco-2 cell assay is an indicator for the undesirable condition of hypercalcemia. This co-transfection assay is a surrogate assay for in vivo calcemic activity of VDR ligands. It is desirable to have high EC50 values for a test compound in this assay. The higher the EC50 values for a compound the less calcemic it will be in vivo. Desired assay results are EC50 greater than or equal to 300 nM. Preferred assay results are greater than 1000 nM.

3. The OCN (Osteocalcin) Promoter Assay

The OCN Promoter Assay is an indicator and marker for osteoporosis. Desired assay results are EC50 less than or equal to 325 mM. Preferred assay results are less than 50 mM.

4. The Mouse Hypercalcemia Assay

The Mouse Hypercalcemia Assay is a six day hypercalcemia test for toxicity and selectivity. Acceptable test results are levels greater than 300 μg/kg/day. Preferred assay results are levels greater than 1000 μg/kg/day.

5. The Keratinocyte Proliferation Assay

This Assay is indicative for the treatment of psoriasis. An acceptable test result is IC50 value of less than or equal to 300 nM. Preferred assay results are IC50 values of less than 100 nM.

6. The IL-10 Induction Assay

This is an in vitro efficacy assay for psoriasis, abscess and adhesion. Psoriasis involves both keratinocytes and immune cells. IL-10 is a unique cytokine because it is anti-inflammatory and immunosuppressive. This assay tells us whether a VDRM is able to function as an agonist in PBMCs (primary blood mononuclear cells) or not. A lower EC50 value is desirable in this assay since a compound with a lower EC50 value will be a better agonist in PBMCs. An acceptable test result is an EC50 value of less than 200 nM. Preferred assay results are EC50 values of less than 100 nM.

7. Other Compound Assay Standards

An alternative measure of the efficacy of compounds of the invention for treatment of osteoporosis is a numerical ratio calculated as follows:

Dose Threshold needed to induce hypercalcemia
    divided by
Dose Threshold needed for bone efficacy An alternative measure of the efficacy of compounds of the invention for treatment of psoriasis is a numerical ratio calculated as follows:
Dose Threshold needed to induce hypercalcemia
divided by
Dose Threshold needed to induce keratinocyte proliferation For the above ratios, Dose Thresholds are determined from dose response curve data.

8. The CaT1 (Calcium Transport Protein 1) Assay

The CaT1 Assay is an indicator for the undesirable condition of hypercalcemia. The higher the EC50 values for a compound the less calcemic it will be in vivo. Desired assay results are EC50 greater than or equal to 500 nM. Preferred assay results are greater than 1000 nM.

Details of the Assay Methods:

(1) Materials and Method for RXR-VDR Heterodimerization Assay:

Transfection Method:
FuGENE 6 Transfection Reagent (Roche Cat #1 814 443)

Growth Media:
D-MEM High Glucose (Gibco BRL Cat #11054-020), 10% FBS, 1% antibiotic-antimycotic (Ab-Am)

FBS heat inactivated (Gibco BRL Cat #10092-147)

Ab-Am (Gibco BRL Cat #15240-062)

Cells:
Grow SaOs-2 cells in T-152 $cm^2$ culture flasks in growth media.
Keep the density at $5-6 \times 10^5$ cells/ml
Passage cells 1:3 twice a week
Add Trypsin EDTA (Gibco BRL Cat #25300-020) and incubate
Resuspend cells in plating media and transfer into growth media.

Wash Media:
HBSS Low Glucose Without Phenol Red (Gibco BRL Cat #14175-095), 1% Ab-Am Plating Media:
D-MEM Low Glucose Without Phenol Red (Gibco BRL Cat #11054-020), 1% Ab-Am

D-MEM

Stripped FBS (Hyclone Cat#SH30068.03 Lot #AHM9371)

Ab-Am

Transfection/Treatment Media:
D-MEM Low Glucose Without Phenol Red only

T-152 $cm^2$ culture flask:
Use Corning Coastar T-152 $cm^2$ culture flask (Cat #430825) to grow the cells Flat well Plates:
Use well plate to plate cells
Use Deep well plate sterile to make up treatment media.

Luciferase Assay Reagent:
Use Steady-Glo Luciferase Reagent from Promega (Cat #E2550) Consists of:

a. E2533 Assay Substrate, lyophilized product and b. E2543 Assay Buffer.

Thaw at room temperature
Store

Day 1: Cell Plating:

Cell Harvesting

Aspirate media from culture flask, rinse cells with HBSS and aspirate.

Add trypsin and incubate.

When cells appear detached, resuspend cells in growth media.

Transfer into a new flask with fresh growth media for passaging the cells.

Plate well plates and two extra plates

A. Cell Count

Mix the cell suspension using pipette

Use Hematocytometer to count the cells

Load cell suspension onto the hemocytometer chamber

Count cells.

Plate seeding:

Use plating media 10% Stripped FBS in D-MEM Low Glucose, Without Phenol Red, 1% Ab-Am Plate 14 plates @ 165 μl/well.

In sterile flask add cell suspension
to plating media.

Mix.

Add cells/well.

Place the cells in the incubator.

Cells should be about 75% confluent prior to transfection.

Step 1: DNA and Media

Add plain DMEM media to tubes for mixing the DNA

Add the Reporter gene pFR-LUC

Add the Gal4-RXR-DEF and VP16-VDR-LBD

Step 2: FuGENE and Media

Prepare plain DMEM media in a tubes for mixing FuGENE

Add FuGENE 6 Transfection Reagent

Incubate

Step 3: FuGENE, DNA and Media Complex

Add FuGENE Media complex from step 2 to DNA Media complex from step 1

Incubate

Step 4: FuGENE, DNA and Media Complex to-well plate

Add FuGENE-DNA-Media complex from step 3 to each plate

Incubate.

Day 3: Dosing

Treatment Preparation

Allow for transfection time

Make a stock solution of the compounds in DMSO

Vortex until all the compounds has been dissolved.

Further dilute in D-MEM (Low Glucose—With out Phenol Red)

Add compounds in quadruplicate to give final volume

Incubate.

Day 4: Luciferase Assay

Read the plates after drug treatment

Remove part of media from all the wells and leave remainder

Add Steady-Glo Luciferase Reagent mixture/wells

Incubate

Count each well using a Luminescence counter, Top Count NXT by Packard
  Set a delay between plates to reduce the background.

(2) Materials and Method for the Caco-2 Cell Assay:

Caco-2 cells, grown in phenol red free, DMEM (Invitrogen, Carlsbad, Calif.) containing 10% charcoal-stripped FCS (Hyclone, Logan, Utah), were transfected with Fugene 6 reagent (Roche Diagnostics, Indianapolis, Ind.). Cells (5000/well) were plated 18 h before transfection in a 96 well plate. The Cells were transfected with Gal4-responsive reporter pFRLuc (150 ng, Stratagene, La Jolla Calif.) and the receptor expression vector pGal4-VDR-LBD (10 ng), along with Fugene 6 reagent (0.2 µl/well). The DNA-Fugene complex was formed by incubating the mixture for 30 min at room temperature. The cells were transfected in triplicate for 5 h, and treated with various concentrations of VDR ligands (form 0.01 nM to 10,000 nM concentration range) 18 h post-transfection. The luciferase activity was quantified using Steady-Glo reagent kit (Promega, Madison, Wis.) as per manufacturer's specifications.

(3) Materials and Method for the OCN Promoter Assay:

The activation of osteocalcin by VDR ligands was evaluated in a rat osteoblast-like cell line RG-15 (ROS 17/2.8) stably expressing rat osteocalcin promoter fused with luciferase reporter gene. The stable cell lines were established as reported before (Activation of Osteocalcin Transcription involves interaction of protein kinase A- and Protein kinase C-dependent pathways. Boguslawski, G., Hale, L. V., Yu, X.-P., Miles, R. R., Onyia, J. E., Santerre R. F., Chandrasekhar, S. J. Biol. Chem. 275, 999-1006, 2000). Confluent RG-15 cells maintained in DMEM/F-12 medium (3:1) containing 5% FBS, 300 □g/ml G418 and at 37° C. under 5% $CO_2$/95% air atmosphere were trypsinized (0.25% trypsin) and plated into white opaque 96-well cell culture plates (25000 cells/well). After 24 hr, cells (in DMEM/F-12 medium+2% FBS) were treated with various concentrations of compounds, dissolved in DMSO. The final DMSO concentration remained at 0.01% (v/v). After 48 hr treatment, the medium was removed, cells were lysed with 50 □l of lysis buffer (From Luciferase reporter assay system, Roche Diagnostics, Indianapolis, Ind.) and assayed for luciferase activity using the Luciferase Reporter Gene Assay kit from Boehringer Mannheim as per manufacturer's specifications.

(4) Materials and Method for the Mouse Hypercalcemia Assay:

Weanling, virus-antibody-free, five to six weeks old female DBF mice (Harlan, Indianapolis, Ind.) are used for all the studies. Animals are allowed to acclimate to local vivarium conditions for 2 days. Mice are maintained on a 12 hr light/dark cycle at 22° C. with ad lib access to food (TD 5001 with 1.2% Ca and 0.9% P, Teklad, Madison, Wis.) and water. The animals then are divided into groups with 4-5 mice per group. Different doses of test compounds prepared in 10% Ethanol and 90% sesame oil are administered to mice orally via gavage for 6 days. $1\alpha$-$25(OH)_2D_3$ 0.5 µg/kg/d was also given to one group of mice as the positive control. Serum ionized calcium is evaluated at 6 hours after the last dosing under isoflurane anesthesia by Ciba-Corning Ca++/PH Analyzer, (Model 634, Chiron Diagnostics Corp., East Walpole, Mass.). Raw data of group differences is assessed by analysis of variance (ANOVA) using Fisher's protected least significant difference (PLSD) where the significance level was $P<0.05$.

(5) The Keratinocyte Proliferation Assay:

KERtr cells (Human skin keratinocyte transformed with a retrovirus vector, obtained from ATCC) were plated in 96-well flat-bottomed plates (3000 cells/well) in 100 □l keratinocyte serum free medium supplemented with bovine pituitary extract in the absence of EGF (Life Technologies, Rockville, Md.) and incubated at 37° C. for two days. The cells were treated with various concentrations of VDR ligands (ten-fold serial dilution from 10,000 nM to 0.1 nM in triplicate), dissolved in 100 □l keratinocyte serum free medium supplemented with bovine pituitary extract in the absence of EGF and incubated at 37° C. for 72 hr. BrdU (5-bromo-2'-deoxyuridine) incorporation was analyzed as a measure of DNA replication (Cell proliferation ELISA kit, Roche Diagnostics, Indianapolis, Ind.) and absorbance was measured at 405 nm. Potency values ($IC_{50}$) values were determined as the concentration (nM) of compound that elicited a half-maximal response.

(6) Materials and Method for Human IL-10 Induction Assay:
  Isolation of peripheral blood mononuclear cells (PBMCs):
    A. Collect 50 ml of human blood and dilute with media, RPMI-1640.
    B. Prepare sterile tubes with ficol.
    C. Add diluted blood to tubes.
    D. Centrifuge.
    E. Discard the top layer and collect the cells from middle layer.
    F. Divide all cells into four tubes and add media.
    G. Centrifuge.
    H. Aspirate off media and resuspend.
    I. Collect all cells
    J. Centrifuge. at 1200 rpm for 10 minutes.
    K. Resuspend in RPMI-1640 with 2% FBS and count cells
  Stimulation of PBMC:
    L. Prepare TPA in DMSO.
    M. Dissolve PHA in water.
    N. Plate TPA/PHA treated PBMCs in well plates.
    O. Incubate.
  Treatment:
    P. Prepare all compound dilutions in plain RPMI-1640 media.
    Q. Add diluted compound.
    R. Incubate.
  Sample Collection and Assay:
    S. Remove all the cells by centrifugation and assay the supernatant for IL-10 by immunoassay.
    1) T. Perform IL-10 assay using anti-human IL-10 antibody coated beads, as described by the manufacturer (Linco Research Inc., St. Charles, Mo.).

(8) Materials and Methods for CaT-1 Assay:

Human colon carcinoma, Caco-2 cells, maintained in DMEM (high glucose with 25 mM Hepes buffer; Invitrogen, Carlsbad, Calif.) supplemented with 10% fetal bovine serum (Invitrogen, Carlsbad, Calif.), are plated at 5500 cell per well in a 96-well plate in a total volume of 100 µl/well. The cells are kept in the 96-well plate for 6 days to differentiate them to small intestinal cells that express the calcium transporter, CaT1. On day 3 after plating, old media is removed and replaced with fresh media (150 µl/well). On day 6 the old media is removed and the cells are kept in treatment media (180 µl/well) that contained 10% charcoal stripped fetal bovine serum (Hyclone, Logan, Uta) in DMEM (low glucose, without phenol red; Invitrogen, Carlsbad, Calif.). The cells are treated with various concentrations of VDR ligands (from 0.01 nM to 10,000 nM concentration range) prepared in treatment media (20 µl/well). Twenty hours post-treatment, total RNA is prepared by RNeasy 96 method as described by the manufacturer (Qiagen, Valencia, Calif.). The RNA is reverse transcribed and amplified for human CaT1 and GAPDH (control) messages by quantitative RT-PCR using ABI PRISM 7900HT Sequence Detection System according to manufacturer's instructions (Applied Biosystems, Foster City, Calif.). Optimized primer pairs and probes for human CaT1 and GAPDH genes are obtained commercially (Applied Biosystems, Foster City, Calif.). Each 20 µl quantitative RT-PCR reaction in a 384-well Taqman PCR plate consists of forward and reverse primers (900 nM), Taqman probe (200 nM), total RNA (4 µl form each well of the 96-well culture plate) and 10 µl of Taqman Universal PCR Master Mix (Roche Diagnostics, Indianapolis, Ind.). Reactions are incubated at 48° C. for 30 minutes, followed by 10 minutes at 95° C. and subjected to 40 cycles of PCR (95° C. for 15 seconds followed by 60° C. for 1 minute). GAPDH is used as an internal control and its primer and probe set are obtained commercially (Applied Biosystems, Foster City, Calif.).

We claim:

1. A compound represented by a formula below or a pharmaceutically acceptable salt thereof:

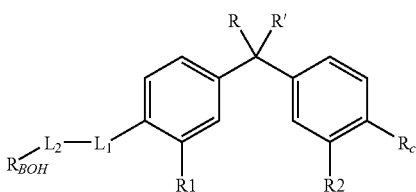

wherein;
R and R' are independently $C_1$-$C_5$ alkyl;
R1 and R2 are independently hydrogen or $C_1$-$C_5$ alkyl;
$L_1$ is a divalent linking group selected from: a bond,

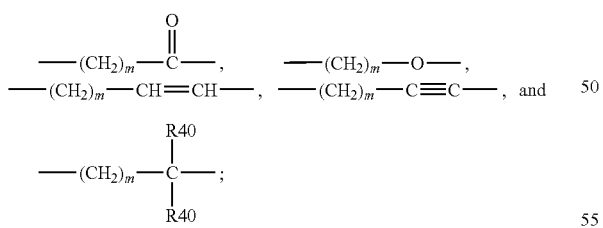

$L_2$ is a divalent linking group selected from: a bond and

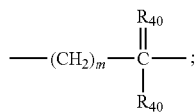

where m is 0, 1 or 2, and each R40 is independently hydrogen, $C_1$-$C_5$ alkyl, or $C_1$-$C_5$ fluoroalkyl;

$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
1-hydroxycyclopropyl,
1-hydroxycyclobutyl,
1-hydroxycyclopentyl, or
1-hydroxycyclohexyl;
provided, however, provided that when
$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl, or
1-hydroxy-2-methyl-1-(methylethyl)propyl;
then $L_1$ and $L_2$ combine as a bond; and
$R_C$ is
—C(O)NH—CH$_2$—C(O)OH,
—C(O)NH—CH(Me)-C(O)OH,
—C(O)NH—C(Me)$_2$-C(O)OH,
—C(O)NMe-CH$_2$—C(O)OH,
—C(O)NMe-CH(Me)-C(O)OH,
—C(O)NMe-C(Me)$_2$-C(O)OH, or
-5-tetrazolyl.

2. A compound represented by formula (II) or a pharmaceutically acceptable salt thereof:

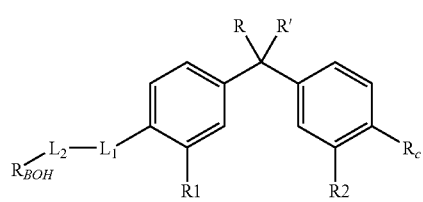

(II)

wherein;
R and R' are independently methyl or ethyl;
R1 and R2 are independently methyl or ethyl;
$L_1$ is a divalent linking group selected from: a bond

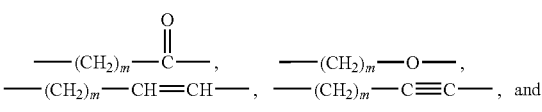

-continued

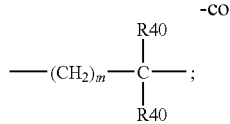

L₂ is a divalent linking group selected from: a bond and

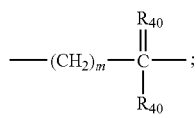

where m is 0 or 1;
R_BOH is selected from
1-hydroxycyclopentyl, and
1-hydroxycyclohexyl, and
R_C is a group selected from
—C(O)NH—CH₂—C(O)OH,
—C(O)NH—CH(Me)-C(O)OH,
—C(O)NH—C(Me)₂-C(O)OH,
—C(O)NMe-CH₂—C(O)OH,
—C(O)NMe-CH(Me)-C(O)OH, and
—C(O)NMe-C(Me)₂-C(O)OH.

3. A compound represented by formula (III) or a pharmaceutically acceptable salt thereof:

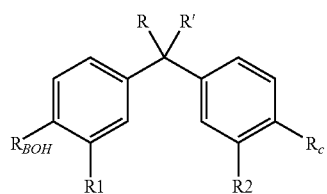

(III)

wherein;
R and R' are independently methyl or ethyl;
R1 and R2 are independently methyl or ethyl;
R_BOH is selected from
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-propyl-3-hydroxypentyl,
3-propyl-3-hydroxypentenyl,
3-propyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl, and
1-hydroxy-2-methyl-1-(methylethyl)propyl; and
R_C is a group selected from
—C(O)NH—CH₂—C(O)OH,
—C(O)NH—CH(Me)-C(O)OH,
—C(O)NH—C(Me)₂-C(O)OH,
—C(O)NH—C(Me)₂-C(O)OH,
—C(O)NMe-CH₂—C(O)OH,
—C(O)NMe-CH(Me)-C(O)OH,
—C(O)NMe-C(Me)₂-C(O)OH, and
C(O)—NH-5-tetrazolyl.

4. A compound represented by formula (AA-1) to (AA-33) or a pharmaceutically acceptable salt thereof:

AA-1)
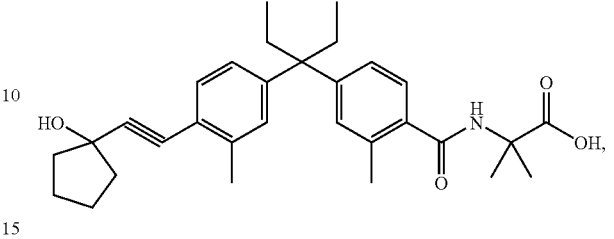

AA-2)
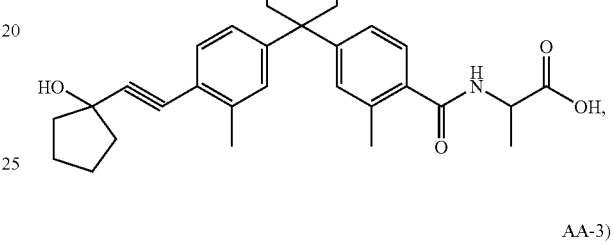

AA-3)
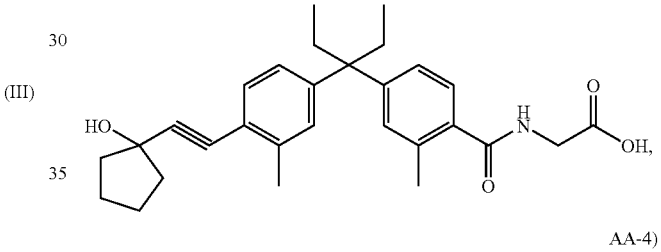

AA-4)
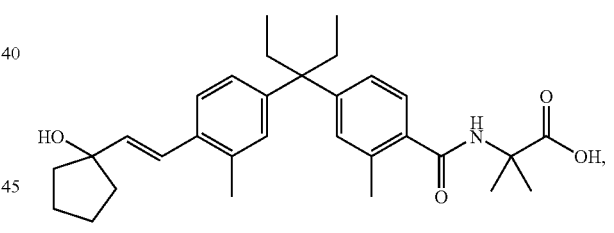

AA-5)
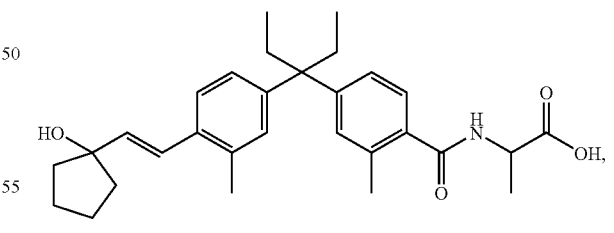

AA-6)
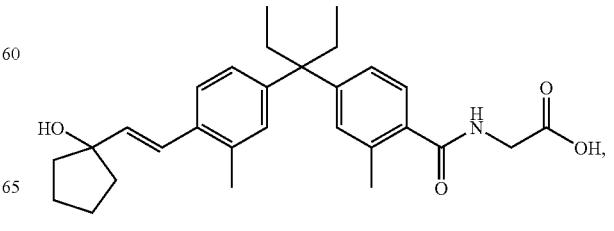

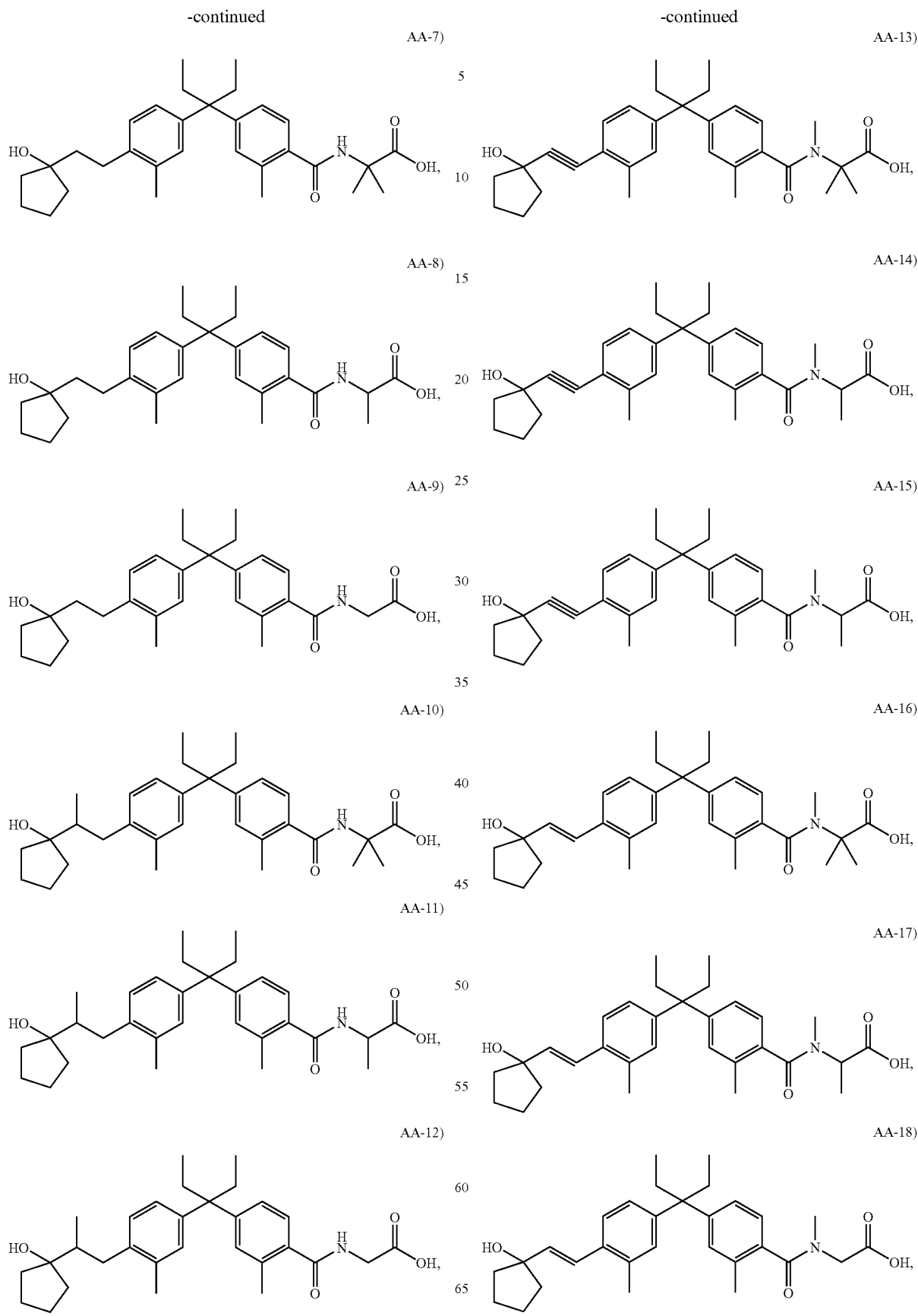

AA-19)
AA-20)
AA-21)
AA-22)
AA-23)
AA-24)
AA-25)
AA-26)
AA-27)
AA-28)
AA-29)
AA-30)

5. A compound represented by formula (BB-1) to (BB-33) or a pharmaceutically acceptable salt thereof:

-continued
BB-11)
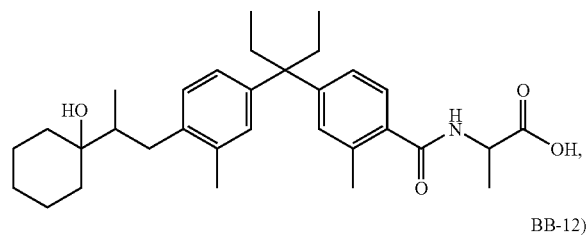
BB-18)
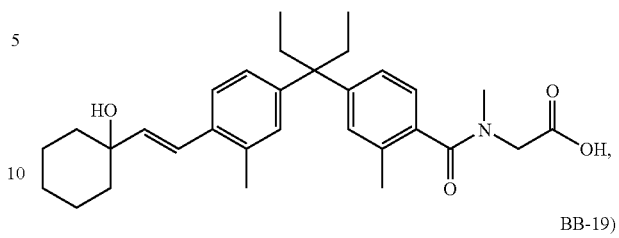
BB-12)
BB-19)
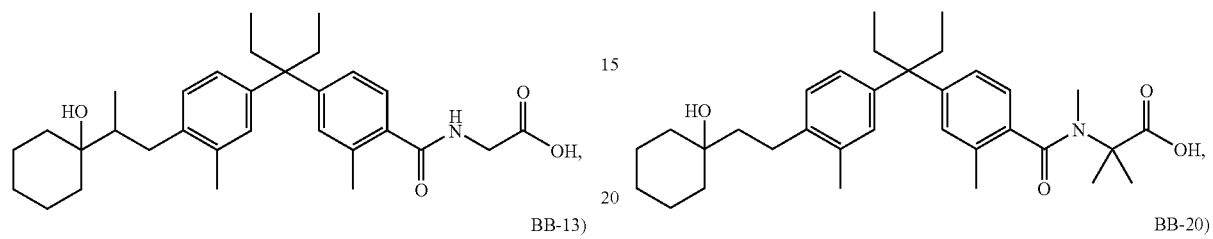
BB-13)
BB-20)
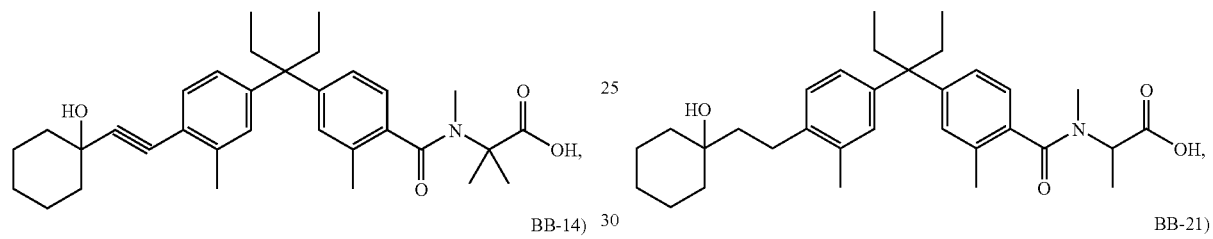
BB-14)
BB-21)
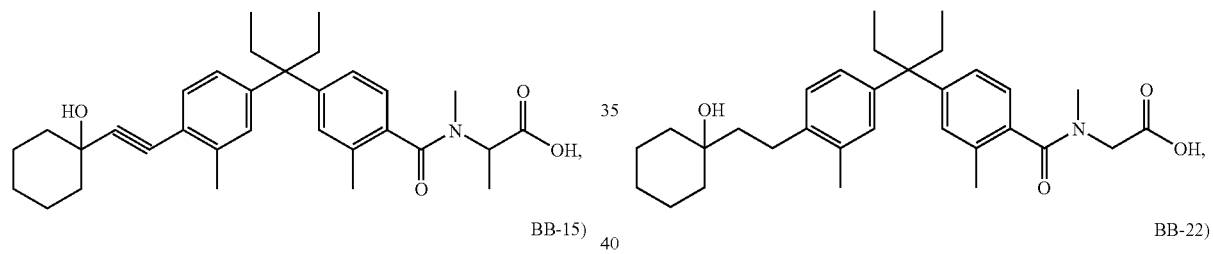
BB-15)
BB-22)
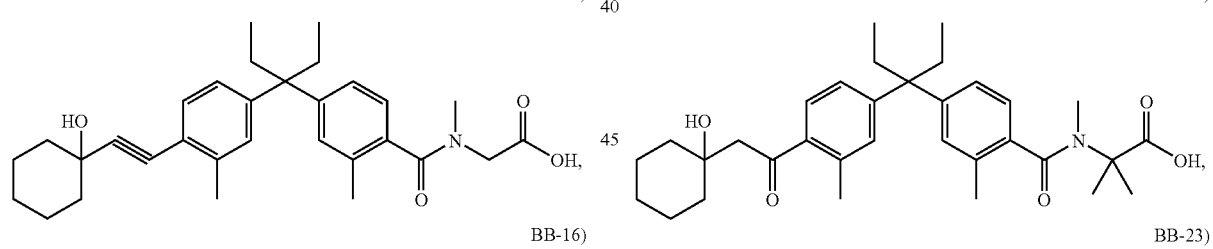
BB-16)
BB-23)
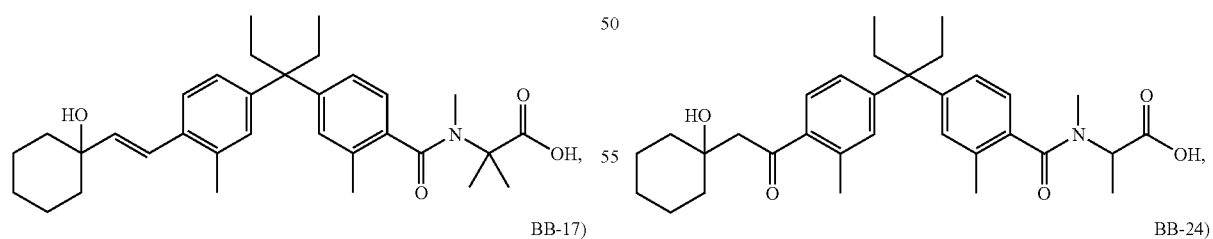
BB-17)
BB-24)
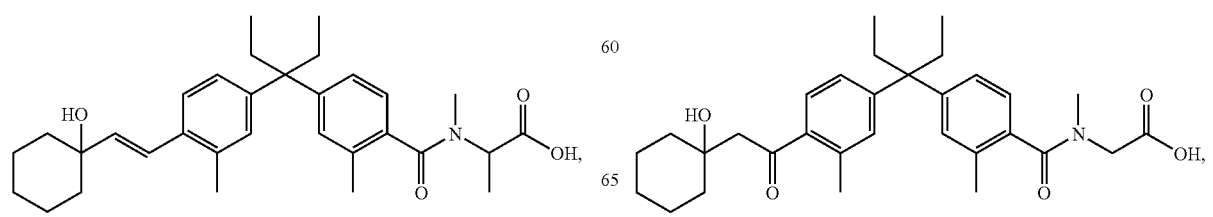

BB-25)
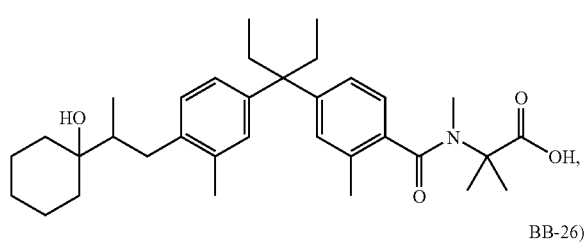
BB-26)
BB-27)
BB-28)
BB-29)
BB-30)
BB-31)
BB-32)
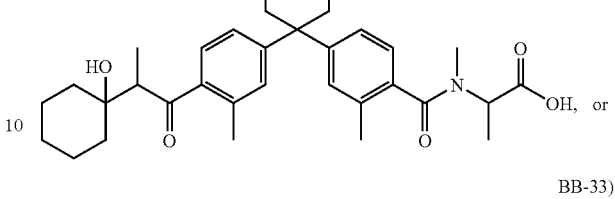
BB-33)
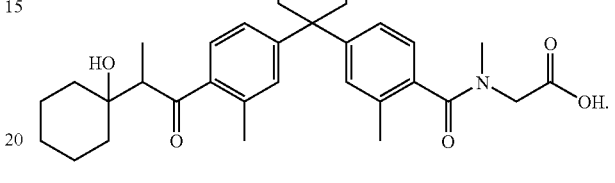
6. A compound represented by formula (CC-1) to (CC-44) or a pharmaceutically acceptable salt thereof:
CC-1)
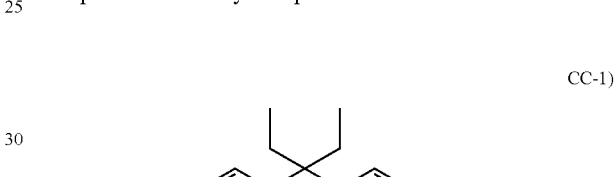
CC-2)
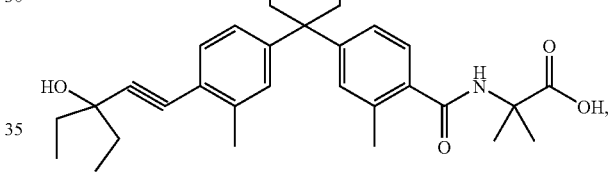
CC-3)
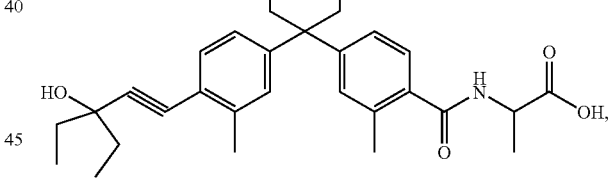
CC-4)
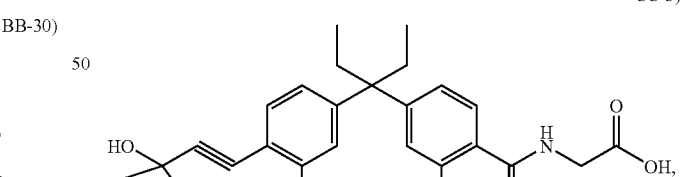

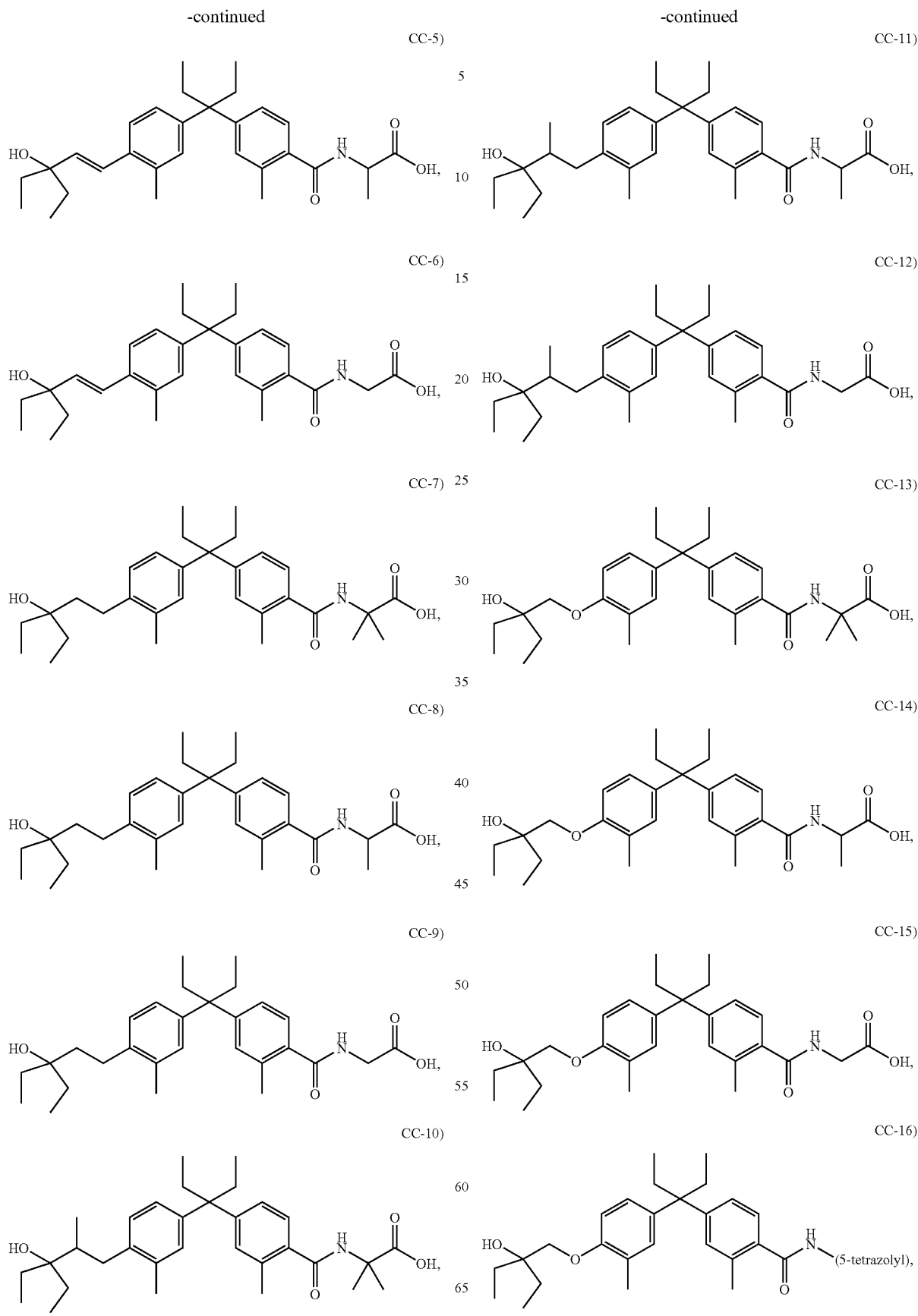

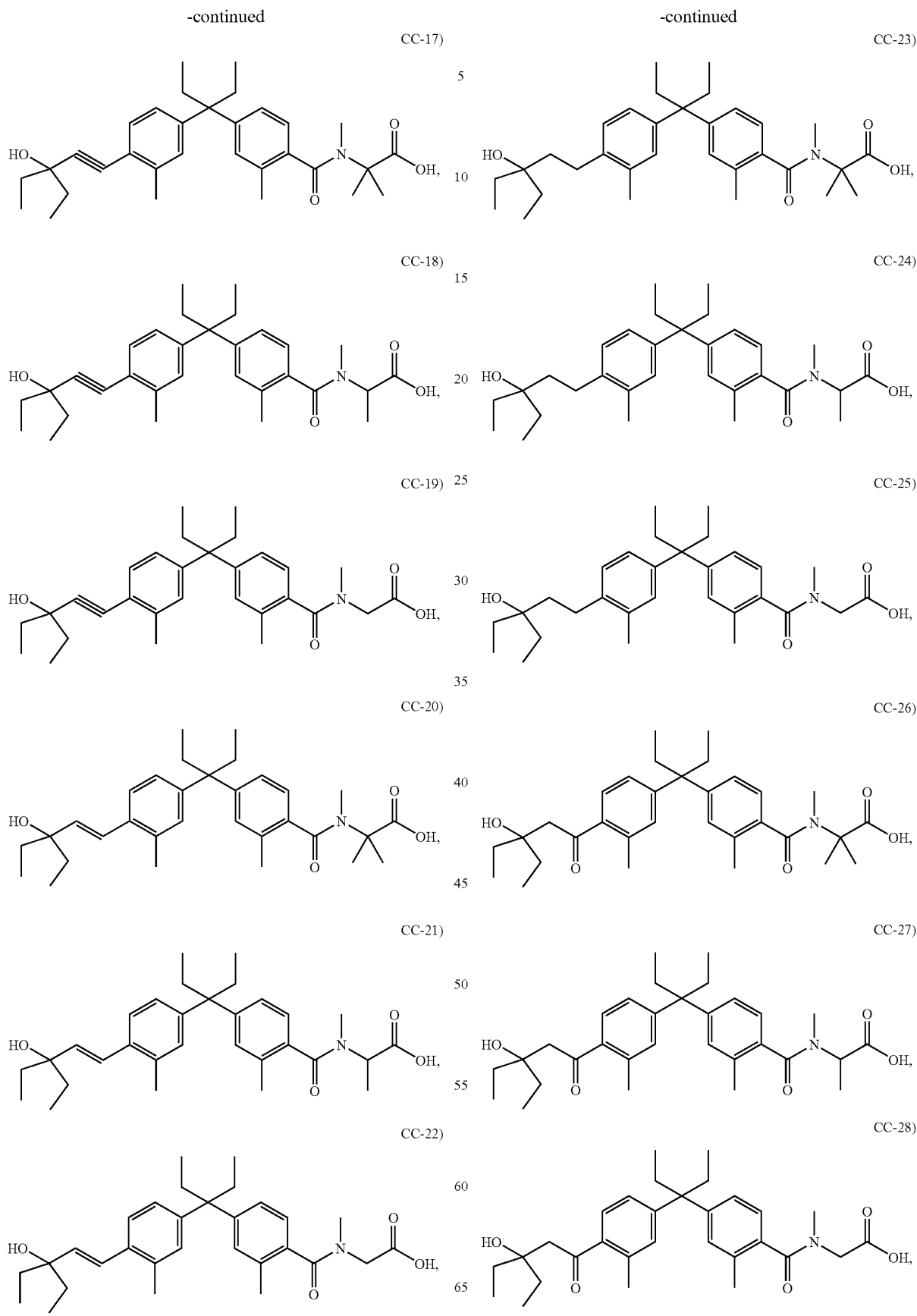

-continued
CC-29)
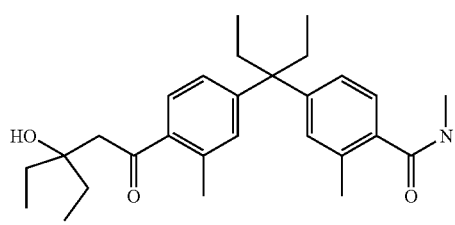
CC-30)
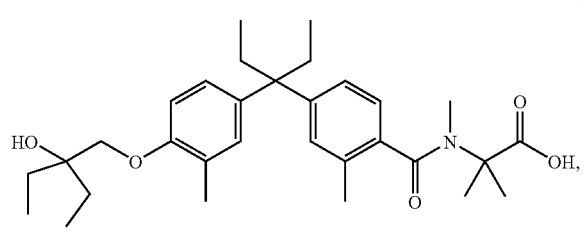
CC-31)
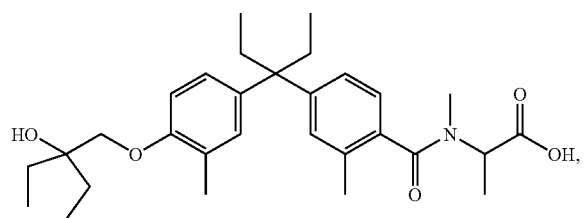
CC-32)
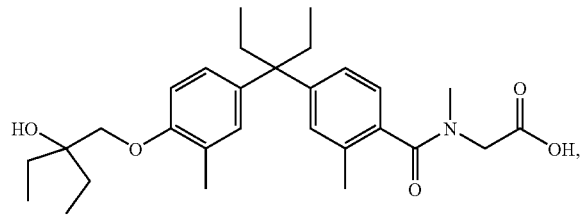
CC-33)
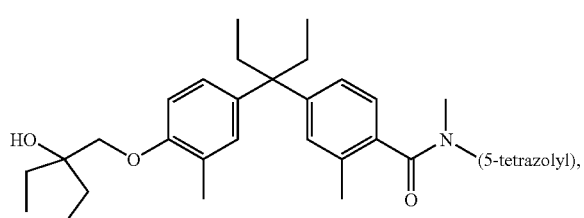
CC-34)
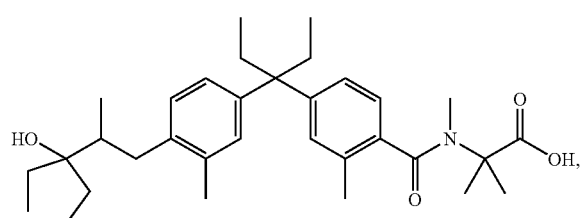
-continued
CC-35)
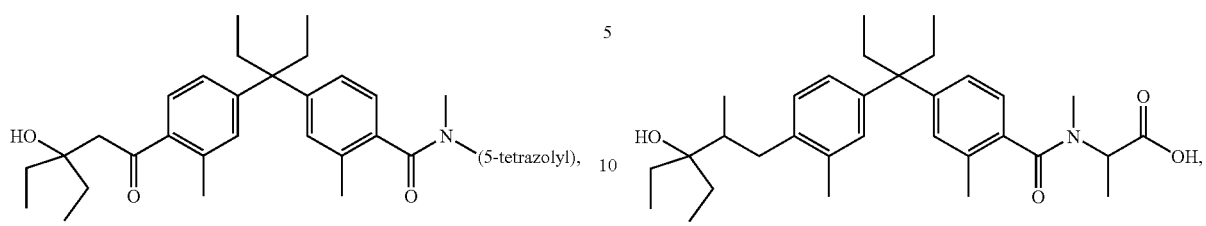
CC-36)
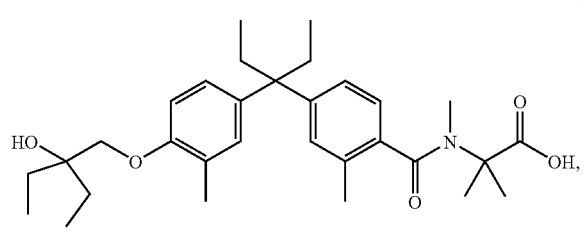
CC-37)
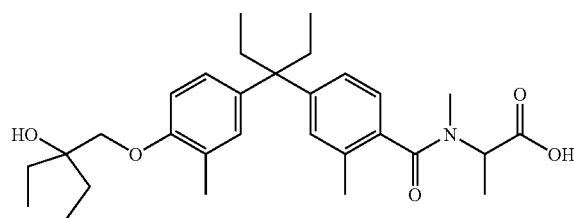
CC-38)
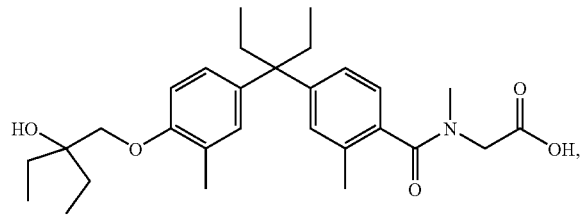
CC-39)
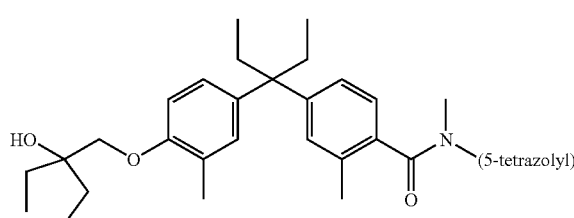
CC-40)
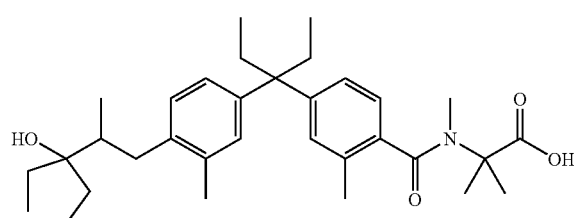

-continued

CC-41)
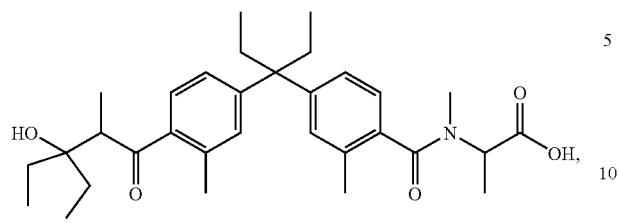

CC-42)
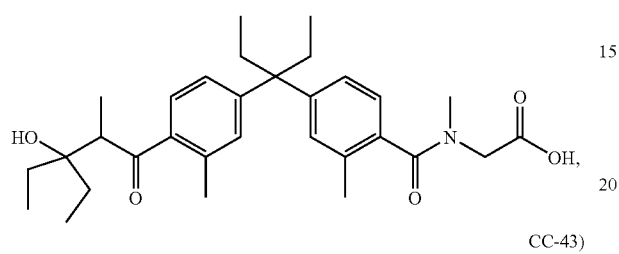

CC-43)
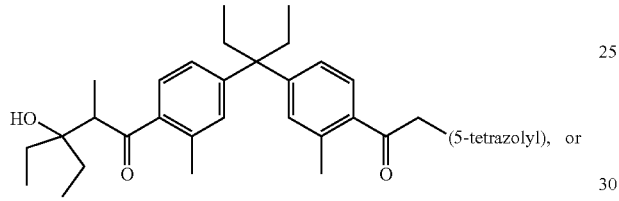

(5-tetrazolyl), or

CC-44)
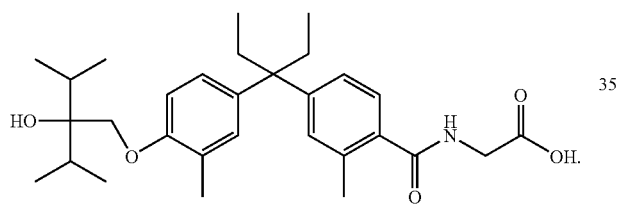

7. The compound according to claim 1 represented by the formula:

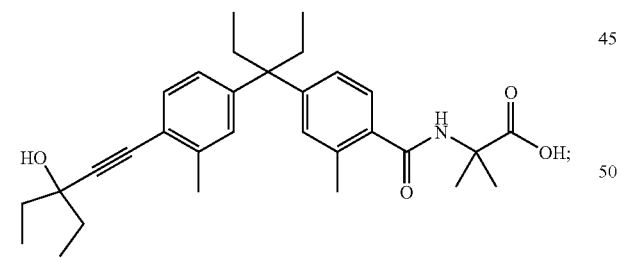

or a pharmaceutically acceptable salt thereof.

8. A compound represented by the formula:

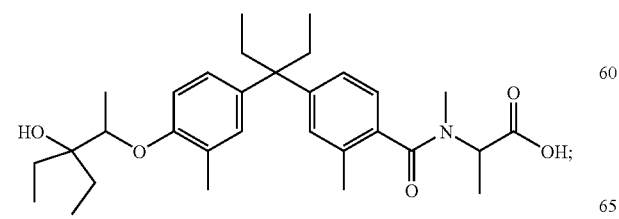

or a pharmaceutically acceptable salt thereof.

9. A compound represented by a formula below or a pharmaceutically acceptable salt thereof:

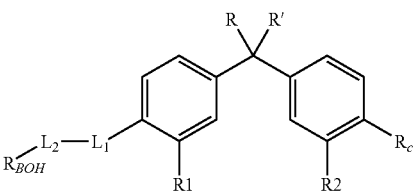

wherein
R and R' are independently $C_1$-$C_5$ alkyl;
R1 and R2 are independently hydrogen or $C_1$-$C_5$ alkyl;
$L_1$ is a divalent linking group selected from: a bond

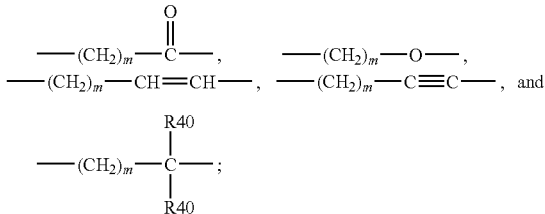, and

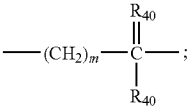

$L_2$ is a divalent linking group selected from: a bond and $$—(CH_2)_m—\overset{R_{40}}{\underset{R_{40}}{C}}—;$$

where m is 0, 1 or 2, and each R40 is independently hydrogen, $C_1$-$C_5$ alkyl, or $C_1$-$C_5$ fluoroalkyl;
$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentenyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl,
3-propyl-3-hydroxypentyl,
3-propyl-3-hydroxypentenyl,
3-propyl-3-hydroxypentynyl,
1-hydroxy-2-methyl-1-(methylethyl)propyl,
1-hydroxycyclopropyl,
1-hydroxycyclobutyl,
1-hydroxycyclopentyl, or
1-hydroxycyclohexyl;
provided, however, provided that when
$R_{BOH}$ is
3-methyl-3-hydroxypentyl,
3-methyl-3-hydroxypentenyl,
3-methyl-3-hydroxypentynyl,
3-ethyl-3-hydroxypentyl,
3-ethyl-3-hydroxypentynyl,
3-ethyl-3-hydroxy-4-methylpentyl,
3-ethyl-3-hydroxy-4-methylpentenyl,
3-ethyl-3-hydroxy-4-methylpentynyl, 3-propyl-3-hydroxypentyl,
3-propyl-3-hydroxypentenyl,
3-propyl-3-hydroxypentynyl, or
1-hydroxy-2-methyl-1-(methylethyl)propyl;
then $L_1$ and $L_2$ combine as a bond; and
$R_C$ is
—C(O)NH—CH$_2$—C(O)OH,
—C(O)NH—CH(Me)-C(O)OH,
—C(O)NH—C(Me)$_2$-C(O)OH,
—C(O)NMe-CH$_2$—C(O)OH,
—C(O)NMe-CH(Me)-C(O)OH,
—C(O)NMe-C(Me)$_2$-C(O)OH, or
-5-tetrazolyl,
wherein a carboxylic acid group of $R_C$ is esterified to a methyl ester; ethyl ester; N,N-diethylglycolamido ester; or morpholinylethyl ester group.

10. The salt derivative of the compound of claim 1 wherein the salt is sodium or potassium.

11. A pharmaceutical formulation comprising the compound of claim 1 together with a pharmaceutically acceptable carrier or diluent.

12. A method of treating a mammal to alleviate the pathological effects of Osteoporosis or Psoriasis wherein the method comprises administering a pharmaceutically effective amount of at least one compound of claim 1.

13. The method of claim 12 for the treatment of psoriasis.

14. The method of claim 12 for the treatment of osteoporosis.

* * * * *